United States Patent
Ling et al.

(10) Patent No.: US 6,613,327 B1
(45) Date of Patent: Sep. 2, 2003

(54) METHODS OF PREVENTING IMMUNE-MEDIATED ABORTION BY INHIBITING A CD28-MEDIATED COSTIMULATORY SIGNAL

(75) Inventors: Vincent Ling, Walpole, MA (US); Gary S. Gray, Brookline, MA (US); James C. Keith, Andover, MA (US); Srinivas Maganti, Portsmouth, NH (US)

(73) Assignee: Genetics Institute, Inc., Cambridge, MA (US)

( * ) Notice: Subject to any disclaimer, the term of this patent is extended or adjusted under 35 U.S.C. 154(b) by 0 days.

(21) Appl. No.: 09/628,129

(22) Filed: Jul. 28, 2000

Related U.S. Application Data

(63) Continuation-in-part of application No. 09/362,812, filed on Jul. 28, 1999, now abandoned.

(51) Int. Cl.$^7$ ............ A61K 38/16; A61K 39/395; C07K 14/705; C07K 16/46
(52) U.S. Cl. ................ 424/134.1; 424/130.1; 424/137.1; 424/141.1; 424/143.1; 424/144.1; 424/152.1; 424/153.1; 424/172.1; 424/173.1; 424/184.1; 424/192.1; 514/885; 530/387.1; 530/387.3; 530/387.5; 530/388.1; 530/388.2; 530/388.22; 530/388.7; 530/388.73; 530/389.1; 530/389.6; 530/350
(58) Field of Search ............ 514/885; 424/130.1, 424/137.1, 141.1, 143.1, 144.1, 152.1, 153.1, 184.1, 172.1, 173.1, 134.1, 192.1; 530/387.1, 387.5, 388.1, 388.2, 388.22, 388.7, 388.73, 389.1, 389.6, 387.3, 350

(56) References Cited

U.S. PATENT DOCUMENTS

| | | | |
|---|---|---|---|
| 5,434,131 A | | 7/1995 | Linsley et al. |
| 5,726,044 A | * | 3/1998 | Lo et al. |
| 6,090,914 A | * | 7/2000 | Linsley et al. |
| 6,338,851 B1 | * | 1/2002 | Gorczynski |

FOREIGN PATENT DOCUMENTS

| | | |
|---|---|---|
| EP | 711829 | 9/1994 |
| EP | 716148 | 9/1994 |
| EP | 814154 | 12/1997 |
| EP | 984023 | 3/2000 |
| WO | WO 98/38216 | 9/1998 |

OTHER PUBLICATIONS

Borriello et al. J. Immunol. 1997; 158:4548–4554.*
Greenfield et al. Crit. Rev. Immunol. 1998; 18:389–418.*
Coyle et al. Nature Immunology 2001 2:203–209.*
Mueller Cur. Biol. 2000 10:R227–R230.*
Ellis et al. J. Immunol. 56:2700–2709 1996.*
Huang Pharmacol. Therapeutics 2000 86:201–215.*
Baldwin et al., 1994, "Platelet endothelial cell adhesion molecule–1 (PECAM–1/CD31): alternatively spliced, functionally distinct isoforms expressed during mammalian cardiovascular development," *Development*, 120:2539–53.
Bermas et al., 1997, "Proliferative response to recall antigens are associated with pregnancy outcome in women with a history of recurrent spontaneous abortion," *J. Clin. Invest.*, 100(6):1330–1334.
Biedermann, K. et al. 1995, "Pregnancy, immunosuppression and reactivation of latent toxoplasmosis," *J. Perinatal Med.*, 23(3):191–203.
Billington, 1992, "The normal fetomaternal immune relationship," *Baillieres Clin. Obstet. Gynaecol.* 6:417–38.
Bonney et al. 1997, "The maternal immune system's interaction with circulating fetal cells," *J. Immunol.* 158:40–47.
Chaouat et al., 1990 "Control of fetal survival in CBA× DBA/2 mice by lymphokine therapy," *J. Reprod. Fertil*, 89:447–58.
Chaouat et al., 1995, "IL–10 prevents naturally occuring fetal loss in the CBA×DBA/2 mating combination, and local defect in IL–10 production in this abortion–prone combination is corrected by in vivo injection of IFN–t," *J. Immunol.*, 154:4261–4268.
Davis et al. 1996 "Primary porcine endothelial cells express membrane–bound B7–2 (CD86) and a soluble factor that co–stimulate cyclosporin A–resistant and CD28–dependent human T cell proliferation," *Int. Immunl.* 8:1099–111.
Djian et al. 1996, "Immunoactive products of placenta. V. Immunoregulatory properties of a low molecular weight compound obtained from human placental cultures," *Am. J. Reprod. Immunol.* 36:11–24.
Duclos et al. 1994 "Relationship between decidual leukocyte infiltration and spontaneous abortion in a murine model of early fetal resorption," *Cell Immunol.* 159:184–93.
Duclos et al. 1995, "Presence of activated macrophages in a murine model of early embryo loss," *Am. J. Reprod. Immunol.*, 33:354–366.
Duclos et al. 1996 "Embryo infiltration by maternal macrophages is associated with selective expression of proto–oncogenes in a murine model of spontaneous abortion," *Biol. Reprod.* 54:1088–95.

(List continued on next page.)

Primary Examiner—Phillip Gambel
Assistant Examiner—Jessica H. Roark
(74) Attorney, Agent, or Firm—Lahive & Cockfield, LLP; Amy E. Mandragouras; Megan E. Williams

(57) ABSTRACT

Methods of inhibiting and diagnosing spontaneous abortion in a subject are provided. The subject methods are based, inter alia, on the administration of an agent that inhibits a CD28-C mediated costimulatory signal in a T cell such that spontaneous abortion in the subject is inhibited. The subject methods are also based on the levels of adhesion molecules, inflammatory cytokines, and immune cell surface molecules which are altered in spontaneous abortion.

26 Claims, 28 Drawing Sheets

OTHER PUBLICATIONS

Ewoldsen et al. 1987 "Killing of mouse blastocyst stage embryos by cytotoxic T lymphocytes directed to major histocompatibility complex antigens," *J. Immunol.* 138(9):2764–70.

Gafter et al., 1997 "Suppressed cell–mediated immunity and monocyte and natural killer cell activity following allogeneic immunization of women with spontaneous recurrent abortion," *J. Clin. Immunol.* 17:408–19.

GenBank Accession No. U90273 for homo sapiens CTLA–4 mRNA, partial cds, Jan. 5, 1999.

GenBank Accession No. U90271 for Rattus Norvegicus CTLA–4 mRNA, complete cds. Jan. 5, 1999.

GenBank Accession No. U90270 for mus musculus CTLA–4 mRNA, partial cds, Jan. 5, 1999.

Hakim, F.T. et al., 1995, "Acute graft–versus–host reaction can be aborted by blockade of costimulatory molecules," *J. Immunol.* 155(4):1757–66.

Herrera–Gonzalez et al., 1993 "Fetal–maternal immune interaction: blocking antibody and survival of the fetus," *Dev. Comp. Immunol.*, 17:1–8.

Hutloff, A. et al., 1999, "ICOS is an inducible T–cell co–stimulator structurally and functionally related to CD28," *Nature*, 397:263–266.

Kaufman, K.A. et al. 1999, "The CTLA–4 gene is expressed in placental fibroblasts," *Mol. Hum. Reprod.*, 5(1):84–87.

Larrick, J.W. "CTLA4–IG–antiCD40 fusion protein for immunotherapy ," (abstract) Federal Research in Progress, National Technical Information Services (NTIS), Springfield, VA; Retrieved from Dialog Information Services, Palo Alto, CA Access No. 285978 1997.

Larsen, C.P. "Activation, apathy, anergy, apoptosis in transplantation," (abstract) Federal research in Progress, National Technical Information Services (NTIS), Springfield, VA; Retrieved from Dialog Information Services, Palo Alto, CA Access No. 285737 1997.

Lee et al. 1997 A comparison of the effects of different degrees of zona pellucida damage followed by cryopreservation on the postthaw development of mouse embryos, *J. Assist. Reprod. Genet.* 14(3):170–3.

Ling et al., 1997 "Structural identification of the hematopoietic progenitor antigen ER–MP12 as the vascular endothelial adhesion molecule PECAM–1 (CD31)," *Eur. J. Immunol.* 27:509–14.

Ling et al., 1998, "Embryonic stem cells and embryoid bodies express lymphocyte costimulatory molecules," *Experimental Cell Research*, 241:55–65.

Liu et al. 1993 "A cloned lymphoid Thy1+tumor line derived from murine yolk sac cells maintained in long–term cell culture in the absence of a thymic microenvironment expresses an unusual cell surface phenotype," *Thymus.* 21(4):221–33.

Lohse et al. 1996 "Antigen–presenting function and B7 expression of murine sinusoidal endothelial cells and Kupffer cells," *Gastroentiology* 110:1175–81.

Marcos et al. 1997 "Antigenic phenotype and gene expression pattern of lymphohemopoietic progenitors during early mouse ontogeny," *J. Immunol.* 158(6):2627–37.

Olivares et al. 1997 "Cultured human decidual stromal cells express B7–1 (CD80) and B7–2 (CD86) and stimulate allogeneic T cells," *Biol. Reprod*, 57:609–15.

Perez, V.L. et al., 1997, "Induction of peripheral T cell tolerance in vivo requires CTLA–4 engagement," *Immunity*, 6(4):411–417.

Riseau et al., 1995 "Vasculogenesis," *Ann. Rev. Cell Dev. Biol.*, 11:73–91.

Romagnani 1996 "Th1 and Th2 in human diseases," *Clin. Immunol. Immunopathol.*, 80(3 part 1):225–235.

Romagnani et al. 1997 "An update on human Th1 and Th2 cells," *International Archives of Allergy and Immunology*, 113(1–3):153–156.

Sargent, I.L. et al. 1988, Maternal immune responses to the fetus in early pregnancy and recurrent miscarriage, *Lancet* 2(8620):1099–104.

Seino et al. 1995 "CD86 (B70/B7–2) on endothelial cells co–stimulates allogeneic CD4+T cells," *Int. Immunol.* 7:1331–7.

Taipale et al 1997 "Growth factors in the extracellular matrix," *FASEB J.* 1997 11(1):51–9.

Tsai, A.F. et al. 1997, "Transmission disequilibrium of maternal CTLA–4 microsatellite alleles in recurrent spontaneous abortion (RSA)," *American J. Human Genetics* 61(4 suppl):A20.

Tsai, A.F. et al. 1998, "Transmission disequilibrium of maternally–inherited CTLA–4 microsatellite alleles in idiopathic recurrent miscarriage," *J. Reprod. Immunol.* 40:147–157.

Van Gool et al., 1996 "CD80, CD86 and CD40 provide accessory signals in a multiple–step T–cell activation model," *Immunol. Reviews* 153:47–83.

Weetman, A.P. 1999, "The immunology of pregnancy," *Thyroid.*, 9(7):643–646.

Wei et al. 1996, "Long term expression of human growth hormone (hGH) in mice containing allogeneic yolk sac cell derived neovascular implants expressing hGH," *Stem Cells*, 14(2):232–238.

Zhang et al. 1993 "The correlation of prolonged survival of maternal skin grafts with the presence of naturally transferred maternal T cells," *Transplantation*, 56:918–21.

Zimmerman, C. et al., 1997 "Antiviral immune responses in CTLA4 transgenic mice," *J. Virology*, 71(3):1802–7.

* cited by examiner

METHODS OF PREVENTING IMMUNE-MEDIATED ABORTION BY INHIBITING A CD28-MEDIATED COSTIMULATORY SIGNAL

RELATED APPLICATION

This application is a continuation-in-part application of U.S. Ser. No. 09/362,812, entitled "Methods of Preventing Immune-Mediated Abortion By Inhibiting Costimulatory Signals", filed Jul. 28, 1999, now abandoned the contents of which are expressly incorporated by reference.

BACKGROUND OF THE INVENTION

In order for T cells to respond to foreign proteins, two signals must be provided by antigen-presenting cells (APCs) to resting T lymphocytes (Jenkins, M. and Schwartz, R. (1987) *J. Exp. Med.* 165, 302–319; Mueller, D. L., et al. (1990) *J. Immunol.* 144, 3701–3709). The first signal, which confers specificity to the immune response, is transduced via the T cell receptor (TCR) following recognition of foreign antigenic peptide presented in the context of the major histocompatibility complex (MHC). The second signal, termed costimulation, induces T cells to proliferate and become functional (Lenschow et al. 1996. *Annu. Rev. Immunol.* 14:233). Costimulation is neither antigen-specific, nor MHC restricted and is thought to be provided by one or more distinct cell surface molecules expressed by APCs (Jenkins, M. K., et al. 1988 *J. Immunol.* 140, 3324–3330; Linsley, P. S., et al. 1991 *J. Exp. Med.* 173, 721–730; Gimmi, C. D., et al., 1991 *Proc. Natl. Acad. Sci.* USA. 88, 6575–6579; Young, J. W., et al. 1992 *J. Clin. Invest.* 90, 229–237; Koulova, L., et al. 1991 *J.Exp. Med.* 173, 759–762; Reiser, H., et al. 1992 *Proc. Natl. Acad. Sci.* USA. 89, 271–275; van-Seventer, G. A., et al. (1990) *J. Immunol.* 144, 4579–4586; LaSalle, J. M., et al., 1991 *J. Immunol.* 147, 774–80; Dustin, M. I., et al., 1989 *J. Exp. Med.* 169, 503; Armitage, R. J., et al. 1992 *Nature* 357, 80–82; Liu, Y., et al. 1992 *J.Exp. Med.* 175, 437–445).

The CD80 (B7-1) and CD86 (B7-2) proteins, expressed on APCs, are critical costimulatory molecules (Freeman et al. 1991. *J. Exp. Med.* 174:625; Freeman et al. 1989 *J. Immunol.* 143:2714; Azuma et al. 1993 *Nature* 366:76; Freeman et al. 1993. *Science* 262:909). B7-2 appears to play a predominant role during primary immune responses, while B7-1, which is upregulated later in the course of an immune response, may be important in prolonging primary T cell responses or costimulating secondary T cell responses (Bluestone. 1995. *Immunity.* 2:555).

One ligand to which B7-1 and B7-2 bind, CD28, is constitutively expressed on resting T cells and increases in expression after activation. After signaling through the T cell receptor, ligation of CD28 and transduction of a costimulatory signal induces T cells to proliferate and secrete IL-2 (Linsley, P. S., et al. 1991 *J. Exp. Med.* 173, 721–730; Gimmi, C. D., et al. 1991 *Proc. Natl. Acad. Sci.* USA. 88, 6575–6579; June, C. H., et al. 1990 *Immunol. Today.* 11, 211–6; Harding, F. A., et al. 1992 *Nature.* 356, 607–609). A second ligand, termed CTLA4 (CD152) is homologous to CD28 but is not expressed on resting T cells and appears following T cell activation (Brunet, J. F., et al., 1987 *Nature* 328, 267–270). CTLA4 appears to be critical in negative regulation of T cell responses (Waterhouse et al. 1995. *Science* 270:985). Blockade of CTLA4 has been found to remove inhibitory signals, while aggregation of CTLA4 has been found to provide inhibitory signals that downregulate T cell responses (Allison and Krummel. 1995. *Science* 270:932). The B7 molecules have a higher affinity for CTLA4 than for CD28 (Linsley, P. S., et al., 1991 *J. Exp. Med.* 174, 561–569) and B7-1 and B7-2 have been found to bind to distinct regions of the CTLA4 molecule and have different kinetics of binding to CTLA4 (Linsley et al. 1994. *Immunity.* 1:793). A new molecule related to CD28 and CTLA4, ICOS, has been identified (Hutloff et al. 1999. *Nature.* 397:263; WO 98/38216), as has its ligand, which is a new B7 family member (Aicher A. et al. (2000) *J. Immunol.* 164:4689–96; Mages H. W. et al. (2000) *Eur. J. Immunol.* 30:1040–7; Brodie D. et al. (2000) *Curr. Biol.* 10:333–6; Ling V. et al. (2000) *J. Immunol.* 164:1653–7; Yoshinaga S. K. et al. (1999) *Nature* 402:827–32). If T cells are only stimulated through the T cell receptor, without receiving an additional costimulatory signal, they become nonresponsive, anergic, or die, resulting in downmodulation of the immune response.

The mechanisms by which the immunoprivileged nature of the embryo is established and maintained during pregnancy are not fully understood; the role of embryonic costimulatory molecules in this process has not been addressed. In a murine model, maternal tolerance of embryonic antigens has been shown to be temporal and resensitization to these antigens are quickly reestablished after pregnancy (Bonney and Matzinger, 1997, *J Immunol* 158, 40–7). Despite this apparent transient tolerance, evidence indicates that dynamic immunological interactions occur at the embryonic/material interface between maternal NK cells and macrophages and embryonic tissues (Duclos et al., 1995; *Am J Reprod Immunol* 33, 354–66; Duclos et al., 1996, *Biol Reprod* 54, 1088–95; Duclos et al., 1994, *Cell Immunol* 159, 184–93).

Macrophages and NK cells are the predominant types of immune cells within the maternal decidua during early embryonic development while T cells accumulate during late development. In a recent report, cultured human decidual cells were found to be capable of antigen presentation (Olivares et al., 1997, *Biol Reprod* 57, 609–15). In an animal model of immune mediated spontaneous abortion, macrophage infiltration of the decidua is an early indication of immunological rejection and embryo resorption (Duclos et al., 1995, *Am J Reprod Immunol* 33, 354–66). It is generally thought that maternal/fetal cellular transfer is rare due to the chorionic cell layers that separate the two systems (Billington, 1992, *Baillieres Clin Obstet Gynaecol* 6, 417–38). However, evidence exists demonstrating that cross trafficking of cells between maternal and fetal systems occurs at very high frequency, albeit at very low levels. In a recent study in which mouse embryos were implanted into transgenic LacZ female mice, the presence of maternal LacZ positive cells in the embryo proper was reported (Piotrowski and Croy, 1996, *Biol Reprod* 54, 1103–10). In a separate transplantation study, it was found that hypoimmunity of recipient mice toward MHC haplotype mismatched maternal skin grafts was correlated with the low level presence of maternal T cells in the neonate, presumably acquired in utero, present in the lymph nodes of the recipient mice (Zhang and Miller, 1993, *Transplantation* 56, 918–21). These observations suggest that low level cellular infiltration of the embryo by maternal lymphocytes is possible during the course of the pregnancy.

Spontaneous early embryo resorption following implantation occurs in many species, but little is known regarding the causes or the prevention of early pregnancy failure. Further insight into the processes that result in spontaneous abortion and the development of improved methods for treating subjects who are at risk for spontaneous abortion would be of great benefit.

SUMMARY OF THE INVENTION

In one aspect, the invention provides a method of inhibiting spontaneous abortion in a subject by administering to the subject an agent that inhibits a costimulatory signal in a T cell such that spontaneous abortion in the subject is inhibited.

In one embodiment, the agent is selected from the group consisting of: an antibody to B7-1, an antibody to B7-2, an antibody to an ICOS ligand, and a combination of an antibody to B7-1 and an antibody to B7-2.

In another embodiment, the agent comprises a soluble form of CD28 or ICOS. In another embodiment, the agent comprises a soluble form of CTLA4. In one embodiment, the soluble form of CTLA4 is CTLA4Ig.

In one embodiment, the CTLA4Ig comprises a constant region domain that has been modified to reduce at least one effector-mediated function.

In one embodiment, the subject is a human.

In another embodiment, the subject is a domesticated animal.

In another embodiment, the subject is an endangered species.

In another embodiment, the subject is a non-human animal which is being used to carry cloned, non-human embryos.

In another aspect, the invention provides a method of down regulating an immune response by a subject to an embryo comprising: administering to a subject a therapeutically effective amount of a soluble CTLA4-Ig fusion protein such that an adverse immune response to the embryo is downregulate. In one embodiment, the subject is a human.

In one embodiment, the subject has had a previous spontaneous abortion.

In one embodiment, the soluble CTLA4-Ig fusion protein is administered to the subject prior to or at the time of implantation of the embryo.

In one embodiment, the method further includes administering to the subject soluble CTLA4-Ig fusion protein after implantation of the embryo.

In one embodiment, the CTLA4Ig comprises a constant region domain that has been modified to reduce at least one effector-mediated function.

In another aspect, the invention provides a method of enhancing the ability of a subject to carry at least one embryo to term comprising: administering to a subject a soluble CTLA4-Ig fusion protein such that the host immune response to the embryo is decreased.

In another embodiment, the invention provides a method of diagnosing a subject at risk for or suffering from immune-mediated spontaneous abortion which includes determining the level of one or more of an adhesion molecule (e.g., VCAM-1, P-selectin, and/or E-selectin), an inflammatory cytokine (e.g., IL-2, IL-10, IL-12, IL-11, TNFα, IL-1β, TGF, RANTES, IL-6, and/or WFN-γ), and/or an immune cell surface molecule (e.g., B7.1, B7.2, CD4, CD8, GL50, and/or ICOS). In another embodiment, the invention provides a method of determining whether treatment of a subject using the methods of the invention is having the desired effect, which includes determining the level of one ore more of an adhesion molecule, an inflammatory cytokine, and/or an immune cell surface molecule.

DETAILED DESCRIPTION

Figure 1A:
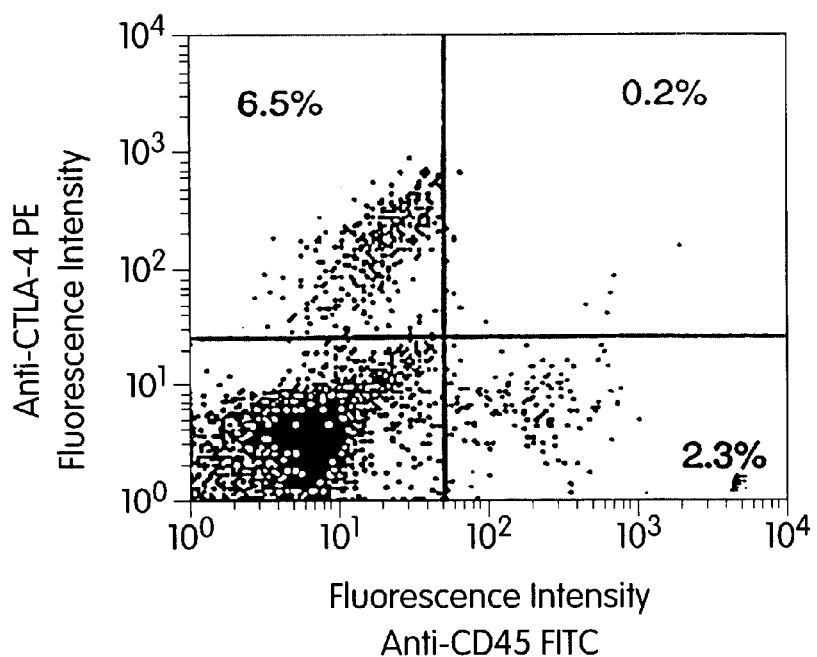
FIG. 1 shows a cytometric plot of antibody stained day 8.5 yolk sac cells. Panel A shows a two dimensional FACS plot of cells stained with anti-CTLA4 PE and anti-CD45 FITC antibodies. Panel B shows a two dimensional FACS plot of cells stained with anti-CTLA4 PE and anti-PECAM-1 FITC antibodies.

The present invention represents an important advance over the prior art by providing for the treatment of immune-mediated abortions. The invention is based, at least in part, on the discovery that an embryonic form of CTLA4 is expressed in mouse yolk sac tissue at times prior to lymphocyte development. In addition, using an animal model, it has been found that the addition of CTLA4 Ig reduces spontaneous abortion in abortion-prone subjects to background levels.

Developing mouse hematopoietic yolk sacs were examined for the presence of costimulatory receptors. Flow cytometric analysis revealed a CTLA4+, PECAM-1+, CD45$^-$ subpopulation of cells within dispersed yolk sac tissues as early as day 8.5 of embryonic development. Whole mount tissue immunohistochemistry localized CTLA4 staining to blood islands and vasculature of yolk sac membranes. In FACS based cross blocking experiments, B7-1-Ig binding to yolk sac cells was inhibited by anti-CTLA4 antibodies, demonstrating that yolk sac CTLA4 recognizes B7-1 as a cognate ligand. RT-PCR of mRNA prepared from yolk sac and maternal spleen yielded specific products when PCR primers specific for the extracellular domain of CTLA4 were used. Collagenase digestion of yolk sac tissues resulted in the elimination of anti-CTLA4 antibody staining, demonstrating yolk sac CTLA4 to be a secreted protein associated with the extracellular matrix. To test whether a soluble/extracellular form of CTLA4 may have a role in maternal tolerance of the embryo, the effects of exogenously applied mCTLA4-Ig fusion protein were examined on an abortion prone mouse model (DBA×CBA). Administration of two 200 ug doses of CTLA4 Ig per mouse delivered intraperitoneally on days 4 and 6 of gestation revealed a reduction of spontaneous abortion from naturally occurring high levels (21%) to background levels (8%). Thus, yolk sac extracellular CTLA4 functions as an immunoprotective agent in tolerizing the maternal immune system against the embryo during development.

Accordingly, the instant invention provides methods which enable subjects, both human and animal subjects, to carry offspring to term.

Before further description of the invention, certain terms employed in the specification, examples and appended claims are, for convenience, collected here.

I. Definitions

As used herein the term "immune mediated abortion" includes spontaneous termination of a preganacy, e.g., a miscarriage. An immune mediated abortion as defined herein includes failure of a fertilized embryo to properly implant in the wall of the uterus of a subject or, once implanted, shedding of the embryo from the uterus of the subject, or reabsorption of an embryo by the subject. An immune-mediated abortion arises from an immune response by a subject to an antigen, e.g., an embryo antigen or paternal antigen expressed by or released from the embryo.

As used herein the term "subject" includes mammalian subjects. A subject of the invention can be or can become naturally pregnant or can be or can become pregnant using assisted reproductive technologies, e.g., in vitro fertilization, insemination, etc. In preferred embodiments the subjects of the present invention are human, although the claimed methods are also for use in other subjects such as domesticated animals, livestock, zoo animals, etc. In one embodiment, a subject of the invention is an endangered species. In another embodiment, a subject is a non-human animal which is used for the purposes of carrying cloned non-human animals. Examples of subjects include humans, cows, cats, dogs, goats, horses, sheep, pigs, and mice.

As used herein the term "agent that inhibits a costimulatory signal in a T cell" includes an agent that prevents a T cell response to an antigen on an embryo by altering the interaction between a costimulatory molecule on a cell, e.g., an antigen presenting cell or a cell in the decidua, and a T cell of a subject. Agents that inhibit a costimulatory signal in a T cell include, e.g., soluble forms of costimulatory molecules or antibodies that block the binding of a costimulatory molecule (e.g., a B7 molecule) and its cognate receptor on a T cell (e.g., CTLA4, CD28, and/or ICOS) without transducing an activating signal to a T cell.

As used herein, the term "implantation" includes attachment of the fertilized egg to the uterine lining following a natural fertilization process or with the aid of assisted reproductive technology. As used herein "assisted reproductive technology" refers to any technically assisted method of reproduction such as, for example ovulation induction, in vitro fertilization, embryo transfer, and the like. In humans implantation usually occurs five to seven days after ovulation in the natural reproductive process.

As used herein, the term "effector function" includes biological responses which require or involve, at least in part, the constant region of an immunoglobulin molecule. Examples of such effector functions include complement activation, Fc receptor interactions, opsonization and phagocytosis, antibody-dependent cellular cytotoxicity (ADCC), release of reactive oxygen intermediates and placental transfer. In one embodiment the CTLA4-immunoglobulin fusion proteins of the invention exhibit reduced IgC region-mediated biological effector functions and thus are efficient agents for downregulating immune responses in a subject. The methods for making such modifications are known in the art, e.g., WO 97/28267.

As used herein the term "therapeutically effective amount" of an agent that inhibits a costimulatory signal in a T cell includes an amount of such an agent that successfully reduces an immune response by a subject to an embryo.

As used herein the term "adverse immune response" includes humoral and/or cellular immune responses e.g., antibody production, NK cell proliferation, and/or activation, T helper cell proliferation and/or activation, cytotoxic T cell proliferation and/or activation which are associated with spontaneous abortion of a fetus. In a preferred embodiment, an immune response which is inhibited by an agent that inhibits a costimulatory signal in a T cell is a cellular immune response. "Immune response" as used herein also includes non-specific immune responses such as macrophage infiltration which may occur in addition to or as a result of specific T and/or B cell activation. Immune responses can be measured using techniques that are known in the art.

As used herein the term "embryo" includes a stage in the development of a multicelled organism between the time that the zygote is fertilized and the point at which the organism developing from that zygote becomes free-living.

II. Agents Which Inhibit A Costimulatory Signal

In one embodiment, an agent which inhibits a costimulatory signal in a T cell is a naturally occurring form of a costimulatory molecule. Naturally occurring forms of costimulatory molecules can be purified from cells or can be recombinantly produced using techniques known in the art. For example, costimulatory proteins can be made by expressing a nucleic acid molecule encoding a costimulatory molecule in a cell such that a costimulatory molecule is produced.

The cell can be, for example, an antigen presenting cell, or a T cell, or a cell transfected with a nucleic acid encoding a costimulatory molecule such that the costimulatory molecule is expressed on the cell surface. Host cells transfected to express peptides can be any procaryotic or eucaryotic cell. For example, a peptide having costimulatory molecule activity can be expressed in bacterial cells such as *E. coli*, insect cells (baculovirus), yeast, or mammalian cells such as Chinese hamster ovary cells (CHO) and NS0 cells. Other suitable host cells and expression vectors may be found in Goeddel, (1990) supra or are known to those skilled in the art. Examples of vectors for expression in yeast *S. cerivisae* include pYepSec1 (Baldari. et al., (1987) *Embo J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.). Baculovirus vectors available for expression of proteins in cultured insect cells (SF 9 cells) include the pAc series (Smith et al., (1983) *Mol. Cell Biol.* 3:2156–2165) and the pVL series (Lucklow, V. A., and Summers, M. D., (1989) *Virology* 170:31–39). Generally, COS cells (Gluzman, Y., (1981) *Cell* 23:175–182) are used in conjunction with such vectors as pCDM8 (Seed, B., (1987) Nature 329:840) for transient amplification/ expression in mammalian cells, while CHO (dhfr⁻ Chinese Hamster Ovary) cells are used with vectors such as pMT2PC (Kaufman et al. (1987), EMBO J. 6:187–195) for stable amplification/expression in mammalian cells. A preferred cell line for production of recombinant protein is the NSO myeloma cell line available from the ECACC (catalog #85110503) and described in Galfre, G. and Milstein, C. ((1981) *Methods in Enzymology* 73(13):3–46; and *Preparation of Monoclonal Antibodies: Strategies and Procedures*, Academic Press, N.Y., N.Y). Vector DNA can be introduced into mammalian cells via conventional techniques such as calcium phosphate or calcium chloride co-precipitation, DEAE-dextran-mediated transfection, lipofectin, or electroporation. Suitable methods for transforming host cells can be found in Sambrook et al. (*Molecular Cloning: A Laboratory Manual*, 2nd Edition, Cold Spring Harbor Laboratory press (1989)), and other laboratory textbooks. When used in mammalian cells, the expression vector's control functions are often provided by viral material. For example, commonly used promoters are derived from polyoma, Adenovirus 2, cytomegalovirus and most frequently, Simian Virus 40.

Peptides having an activity of a costimulatory molecule expressed in mammalian cells or otherwise can be purified according to standard procedures of the art, including ammonium sulfate precipitation, fractionation column chromatography (e.g. ion exchange, gel filtration, electrophoresis, affinity chromatography, etc.) and ultimately, crystallization (see generally, "Enzyme Purification and Related Techniques", *Methods in Enzymology*, 22:233–577 (1971)).

Nucleotide sequences of costimulatory molecules are known in the art and can be found in the literature or on a database such as GenBank. See, for example, B7-2 (Freeman et al. 1993 *Science*. 262:909 or GenBank Accession numbers P42081 or A48754); B7-1 (Freeman et al. *J. Exp. Med.* 1991. 174:625 or GenBank Accession numbers P33681 or A45803; CTLA4 (See e.g., Ginsberg et al. 1985. *Science*. 228:1401; or GenBank Accession numbers P16410 or 291929); and CD28 (Aruffo and Seed. *Proc Natl. Acad. Sci.* 84:8573 or GenBank Accession number 180091) ICOS (WO 98/38216; Hutloff et al. 1999. *Nature* 397:263) and related sequences.

In addition to naturally occurring forms of costimulatory molecules, the term "costimulatory molecule" also includes non-naturally occurring, e.g., mutant forms of costimulatory molecules which retain the function of a costimulatory molecule, e.g., the ability to bind to cognate counter receptor. For example, DNA sequences capable of hybridizing to DNA encoding a B7 molecule, a CTLA4 molecule, a CD28 molecule, or an ICOS molecule under conditions that avoid hybridization to non-costimulatory molecule genes, (e.g., under conditions equivalent to 65° C. in 5×SSC (1×SSC= 150 mM NaCl/0.15 M Na citrate)) are costimulatory molecules within the scope of the invention. Alternatively, DNA sequences which retain amino acid sequence identity over regions of the nucleic acid molecule which encode protein domains which are important in costimulatory molecule function, e.g., binding to other costimulatory molecules, can be used to produce costimulatory proteins which can be used as agents which inhibit a costimulatory signal in a T cell. Preferably, non naturally occurring costimulatory molecules have significant (e.g., greater than 70%, preferably greater than 80%, and more preferably greater than 90–95%) amino acid identity with a naturally occurring amino acid sequence of a costimulatory molecule extracellular domain.

The term "percent (%) identity" as used in the context of nucleotide and amino acid sequences (e.g., when one amino acid sequence is said to be X% identical to another amino acid sequence) refers to the percentage of identical residues shared between the two sequences, when optimally aligned. To determine the percent identity of two nucleotide or amino acid sequences, the sequences are aligned for optimal comparison purposes (e.g., gaps may be introduced in one sequence for optimal alignment with the other sequence). The residues at corresponding positions are then compared and when a position in one sequence is occupied by the same residue as the corresponding position in the other sequence, then the molecules are identical at that position. The percent identity between two sequences, therefore, is a function of the number of identical positions shared by two sequences (i.e., % identity=# of identical positions/total # of positions× 100).

Computer algorithms known in the art can be used to optimally align and compare two nucleotide or amino acid sequences to define the percent identity between the two sequences. A preferred, non-limiting example of a mathematical algorithm utilized for the comparison of two sequences is the algorithm of Karlin and Altschul (1990) *Proc. Natl. Acad. Sci. USA* 87:2264–68, modified as in Karlin and Altschul (1993) *Proc. Natl. Acad. Sci. USA* 90:5873–77. Such an algorithm is incorporated into the NBLAST and XBLAST programs of Altschul, et al. (1990) *J. Mol. Biol.* 215:403–10. To obtain gapped alignments for comparison purposes, Gapped BLAST can be utilized as described in Altschul et al., (1997) *Nucleic Acids Research* 25(17):3389–3402. When utilizing BLAST and Gapped BLAST programs, the default parameters of the respective programs (e.g., XBLAST and NBLAST) can be used.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. If multiple programs are used to compare sequences, the program that provides optimal alignment (i.e., the highest percent identity between the two sequences) is used for comparison purposes.

To determine amino acid residues of a costimulatory molecule which are likely to be important in the binding of a costimulatory molecule to its counter receptor, amino acid sequences comprising the extracellular domains of costimulatory molecules of different species, e.g., mouse and human, can be aligned and conserved residues (e.g., identical) noted. This can be done, for example e.g., using any standard alignment program, such as MegAlign (DNA STAR). Such conserved or identical residues are likely to be necessary for proper binding of costimulatory molecules to their receptors and are, thus, not likely to be amenable to alteration.

Specific residues of costimulatory molecules which are important in binding have also been determined. For example, the portion of CD28 which is critical for interaction with B7-1 and B7-2 has been determined using site directed mutagenesis, CD28 monoclonal antibody epitope mapping, receptor based adhesion assays, and direct binding of Ig-fusion proteins to cell surface receptors. A stretch of proline rich sequence in CD28, MYPPPY (SEQ ID NO: 1), has been found to be critical to the function of that protein (Truneh et al. 1996. *Mol. Immunol.* 33:321). Likewise, the regions of the B7-1 molecule which are important in mediating the functional interaction with CD28 and CTLA4 have been identified by mutation. Two hydrophobic residues in the V-like domain of B7-1, including the Y87 residue, which is conserved in all B7-1 and B7-2 molecules cloned from various species, were found to be critical (Fargeas et al. 1995. *J. Exp. Med.* 182:667). Using these, or similar, techniques, amino acid residues of the extracellular domains of costimulatory molecules which are critical and, therefore, not amenable to alteration can be determined.

For use in the claimed methods, costimulatory molecules can be expressed in soluble form to block the interaction of costimulatory molecules and their counter receptors on T cells to thereby inhibit a costimulatory signal in a T cell. Costimulatory molecules can also be used as immunogens to make antibodies that block a costimulatory signal. Such soluble costimulatory molecules or antibodies are useful as agents which inhibit a costimulatory signal in a T cell as described in further detail herein. The agents which inhibit a costimulatory signal in a T cell can be administered in the form of proteins or can be administered in the form of nucleic acid molecules and can be translated into proteins in a subject.

A. Agents Which Act Extracellularly to Inhibit a Costiniulatory Signal in a T Cell 1. Soluble Forms of Costimulatory Molecules In one embodiment, the agent which blocks a costimulatory signal in a T cell is a soluble form of a costimulatory molecule. Such soluble forms of these cell surface molecules have been found to block the transduction of a costimulatory signal in a T cell. In one embodiment, a soluble form of a CD28 or ICOS molecule can be used to block the transduction of a costimulatory signal in a T cell (see e.g., U.S. Pat. No. 5,521,288).

In one embodiment, the agent which blocks a costimulatory signal in a T cell is a soluble form of CTLA4. DNA sequences encoding the human and murine CTLA4 protein are known in the art, see e.g., Dariavich, et al. (1988) *Eur. J. Immunol.* 18(12), 1901–1905; Brunet, J. F., et al. (1987) supra; Brunet, J. F. et al. (1988) *Immunol. Rev.* 103:21–36; and Freeman, G. J., et al. (1992) *J. Immunol.* 149, 3795–3801. In certain embodiments, the soluble CTLA4 protein comprises the entire CTLA4 protein. In preferred embodiments, a soluble CTLA4 protein comprises the extracellular domain of a CTLA4 protein. For example, a soluble, recombinant form of the extracellular domain of CTLA4 has been expressed in yeast (Gerstmayer et al. 1997. *FEBS Lett.* 407:63). In other embodiments, the soluble CTLA4 proteins comprise at least a portion of the extracellular domain of CTLA4 protein which retains the ability to bind to B7-1 and/or B7-2.

In one embodiment the soluble CTLA4 protein or portion thereof is a fusion protein comprising at least a portion of CTLA4 which binds to B7-1 and/or B7-2 and at least a portion of a second non-CTLA4 protein. For example, a soluble, recombinant form of the extracellular domain of CTLA4 has been expressed in yeast (Gerstmayer et al. 1997. *FEBS Lett.* 407:63). In preferred embodiments, the CTLA4 fusion protein comprises a CTLA4 extracellular domain which is fused at the amino terminus to a signal peptide, e.g., from oncostatin M (see e.g., WO93/00431).

In a particularly preferred embodiment, a soluble form of CTLA4 is a fusion protein comprising the extracellular domain of CTLA4 fused to a portion of an immunoglobulin molecule. Such a fusion protein, CTLA4Ig, can be made using methods known in the art (see e.g., Linsley 1994. *Perspectives in Drug Discovery and Design* 2:221; Linsley WO 93/00431 and U.S. Pat. Nos. 5,770,197, and 5,844,095).

In one embodiment, the agent which blocks a costimulatory signal in a T cell is at least one of a soluble form of B7-1, a soluble form of B7-2, or a soluble form of an ICOS ligand. In another embodiment, a combination of two reagents selected from the group consisting of a soluble form of B7-1, a soluble form of B7-2, or a soluble form of ICOS ligand. DNA sequences encoding B7 proteins are known in the art, see e.g., B7-2 (Freeman et al. 1993 *Science.* 262:909 or GenBank Accession numbers P42081 or A48754); B7-1 (Freeman et al. *J. Exp. Med.* 1991. 174:625 or GenBank Accession numbers P33681 or A45803. In certain embodiments, the soluble B7 protein comprises an entire B7 protein. In preferred embodiments, a soluble B7 protein comprises the extracellular domain of a B7 protein. In other embodiments, the soluble B7 proteins comprise at least a portion of the extracellular domain of B7 protein which retains the ability to bind to CTLA4, CD28, and/or ICOS.

In one embodiment the soluble B7 protein or portion thereof is a fusion protein comprising at least a portion of B7 which binds to CD28, CTLA4, and/or ICOS and at least a portion of a second non-B7 protein. In preferred embodiments, the B7 fusion protein comprises a B7 extracellular domain which is fused at the amino terminus to a signal peptide, e.g., from oncostatin M (see e.g., WO93/00431).

In a particularly preferred embodiment, a soluble form of B7 is a fusion protein comprising the extracellular domain of B7 fused to a portion of an immunoglobulin molecule. Such a fusion protein, a B7Ig, can be made using methods known in the art (see e.g., Linsley 1994. *Perspectives in Drug Discovery and Design* 2:221; Linsley WO 93/00431, U.S. Pat. Nos. 5,770,197, 5,580,756, or 5,521,288).

2. Antibodies Which Bind to Costimulatory Molecules

In certain embodiments, the agent which blocks a costimulatory signal in a T cell is an antibody which binds to a costimulatory molecule. In making antibodies which bind to costimulatory molecules, a costimulatory protein, a portion of a costimulatory protein, (e.g., a peptide derived from a costimulatory protein), or fusion protein which includes all or a portion of an amino acid sequence of a costimulatory molecule can be used to generate anti-protein and/or anti-peptide polyclonal antisera or monoclonal antibodies using standard methods. The term antibody as used herein is meant to include whole antibodies as well as fragments thereof. Fragments of antibodies (e.g., Fab' fragments, F(ab')$_2$ fragments, or single chain antibodies) can be made using methods well known in the art.

It will be appreciated by those skilled in the art that it is routine to generate antibodies to human costimulatory molecules by following standard techniques. Antibodies may either be polyclonal or monoclonal antibodies, or antigen binding fragments of such antibodies. Of particular significance for use in therapeutic applications are antibodies that inhibit binding of a costimulatory molecule with its natural ligand(s) on the surface of immune cells, thereby inhibiting costimulation of the immune cell. Preferred costimulatory molecule antibodies are those capable of inhibiting or down-regulating T cell mediated immune responses by binding B7-2, B7-1, or an ICOS ligand on the surface of a cell, e.g., a B lymphocyte, and preventing interaction with CTLA4, CD28, and/or ICOS. Other preferred anti-costimulatory molecule antibodies are those which, in combination with a second antibody which binds to another costimulatory molecule, result in increased inhibition of costimulation of a T cell when compared to the first antibody alone, e.g., a combination of anti-B7-1 and anti-B7-2 antibodies.

A. The Immunogen. The term "immunogen" is used herein to describe a composition containing a costimulatory molecule peptide as an active ingredient used for the preparation of antibodies against a costimulatory molecule to develop an agent that inhibits a costimulatory signal in a T cell. When a costimulatory molecule peptide is used to induce antibodies it is to be understood that the peptide can be used alone, or linked to a carrier as a conjugate, or as a peptide polymer.

For example, a mammal, (e.g., a mouse, hamster, or rabbit) can be immunized with an immunogenic form of the costimulatory protein or peptide which elicits an antibody response in the mammal. The immunogen can be, for example, a recombinant costimulatory molecule protein, or fragment thereof, a synthetic peptide fragment or a cell that expresses a costimulatory molecule on its surface. Recombinant costimulatory proteins or peptides can be produced as described supra.

To generate suitable anti-costimulatory molecule antibodies, the immunogen should contain an effective, immunogenic amount of a peptide having a costimulatory molecule activity, typically as a conjugate linked to a carrier. The effective amount of peptide per unit dose depends, among other things, on the species of animal inoculated, the body weight of the animal and the chosen immunization regimen. The immunogen preparation will typically contain peptide concentrations of about 10 micrograms to about 500 milligrams per immunization dose, preferably about 50 micrograms to about 50 milligrams per dose. An immunization preparation can also include an adjuvant as part of the diluent. Adjuvants such as complete Freund's adjuvant (CFA), incomplete Freund's adjuvant (WFA) and alum are materials well known in the art, and are available commercially from several sources.

Those skilled in the art will appreciate that, instead of using naturally occurring forms of a costimulatory molecule for immunization, synthetic peptides can be employed to raise antibodies for use this invention. Both soluble and membrane bound a costimulatory molecule protein or peptide fragments are suitable for use as immunogens and can be isolated, e.g., by immunoaffinity purification as well. A purified form of a costimulatory molecule protein, such as may be isolated as described above or as known in the art, can be used directly as an immunogen, or alternatively, can be linked to a suitable carrier protein by conventional techniques, e.g., by chemical coupling as well as by genetic engineering using a cloned gene of a costimulatory molecule protein.

The peptide or protein chosen for immunization can be modified to increase its immunogenicity. For example, techniques for conferring immunogenicity on a peptide include conjugation to carriers or other techniques well known in the art. Any peptide chosen for immunization can also be synthesized. In certain embodiments, such peptides can be synthesized as branched polypeptides, to enhance immune responses, as is known in the art (see, e.g., Peptides. Edited by Bernd Gutte Academic Press 1995. pp. 456–493).

The purified costimulatory molecule protein can also be covalently or noncovalently modified with non-proteinaceous materials such as lipids or carbohydrates to enhance immunogenecity or solubility. Alternatively, a purified costimulatory molecule protein can be coupled with or incorporated into a viral particle, a replicating virus, or other microorganism in order to enhance immunogenicity. The costimulatory molecule protein may, for example, be chemically attached to the viral particle or microorganism or an immunogenic portion thereof.

In an illustrative embodiment, a purified costimulatory molecule protein, or a peptide fragment having a costimulatory molecule activity (e.g., produced by limited proteolysis or recombinant DNA techniques) is conjugated to a carrier which is immunogenic in animals. Preferred carriers include proteins such as albumin, serum proteins (e.g., globulins and lipoproteins), and polyamino acids. Examples of useful proteins include bovine serum albumin, rabbit serum albumin, thyroglobulin, keyhole limpet hemocyanin, egg ovalbumin and bovine gamma-globulin. Synthetic polyamino acids such as polylysine or polyarginime are also useful carriers. With respect to the covalent attachment of a costimulatory molecule protein or peptide fragments to a suitable immunogenic carrier, there are a number of chemical cross-linking agents that are known to those skilled in the art. Preferred cross-linking agents are heterobifunctional cross-linkers, which can be used to link proteins in a stepwise manner. A wide variety of heterobifunctional cross-linkers are known in the art, including succinimidyl 4-(N-maleimidomethyl) cyclohexane-1-carboxylate (SMCC), m-Maleimidobenzoyl-N-hydroxysuccinimide ester (MBS); N-succinimidyl (4-iodoacetyl) aminobenzoate (SIAB), succinimidyl 4-(p-maleimidophenyl) butyrate (SMPB), 1-ethyl-3-(3-dimethylaminopropyl) carbodiimide hydrochloride (EDC); 4-succinimidyloxycarbonyl-a-methyl-a-(2-pyridyldithio)-tolune (SMPT), N-succinimidyl 3-(2-pyridyldithio) propionate (SPDP), succinimidyl 6-[3-(2-pyridyldithio)propionate]hexanoate (LC-SPDP).

In may also be desirable to simply immunize with whole cells which express a costimulatory molecule protein on their surface. Various cell lines can be used as immunogens to generate monoclonal antibodies to a costimulatory molecule antigen, including, but not limited to activated B cells. For example, splenic B cells can be obtained from a subject and activated with anti-immunoglobulin. Alternatively, a B cell line can be used, provided that a costimulatory molecule is expressed on the cell surface, such as the Raji cell line (B cell Burkett's lymphoma, see e.g., Freeman, G. J. et al. (1993) *Science* 262:909–911) or the JY B lymphoblastoid cell line (see e.g., Azuma, M. et al. (1993) *Nature* 366:76–79). Whole cells that can be used as immunogens to produce costimulatory molecule specific antibodies also include recombinant transfectants. For example, COS and CHO cells can be reconstituted by transfection with a costimulatory molecule cDNA, such as described by Knudson et al. (1993, *PNAS* 90:4003–4007); Travernor et al. (1993, *Immunogenitics* 37:474–477); Dougherty et al. (1991, *J Exp Med* 174:1–5); and Aruffo et al. (1990, *Cell* 61:1303–1313), to produce intact costimulatory molecule on the cell surface. These transfectant cells can then be used as immunogen to produce anti-costimulatory molecule antibodies of preselected specificity. Other examples of transfectant cells are known, particularly eukaryotic cells able to glycosylate the a costimulatory molecule protein, but any procedure that works to express transfected costimulatory molecule genes on the cell surface could be used to produce the whole cell immunogen.

In yet another embodiment, as an alternative to administering the immunogen, the immunogen can be synthesized by the subject. This can be done using a plasmid DNA construct which is similar to those used for delivery of reporter or therapeutic genes. Such a construct preferably comprises a bacterial origin of replication that allows amplification of large quantities of the plasmid DNA; a prokaryotic selectable marker gene; a nucleic acid sequence encoding a immunogen; eukaryotic transcription regulatory elements to direct gene expression in the host cell; and a polyadenylation sequence to ensure appropriate termination of the expressed mRNA (Davis. 1997. *Curr. Opin. Biotechnol.* 8:635). Vectors used for DNA immunization may optionally comprise a signal sequence (Michel et al. 1995. *Proc. Natl. Acad. Sci* USA. 92:5307; Donnelly et al. 1996. *J. Infect Dis.* 173:314). DNA vaccines can be administered by a variety of means, for example, by injection (e.g., intramuscular, intradermal, or the biolistic injection of DNA-coated gold particles into the epidermis with a gene gun that uses a particle accelerator or a compressed gas to inject the particles into the skin (Haynes et al. 1996. *J. Biotechnol.* 44:37)). Alternatively, DNA vaccines can be administered by non-invasive means. For example, pure or lipid-formulated DNA can be delivered to the respiratory system or targeted elsewhere, e.g., Peyers patches by oral delivery of DNA (Schubbert. 1997. *Proc. Natl. Acad. Sci. USA* 94:961). Attenuated microorganisms can be used for delivery to mucosal surfaces. (Sizemore et al. 1995. Science. 270:29)

B. Polyclonal Anti-Costimulatory Molecule Antibodies. Polycolonal antibodies to a purified costimulatory molecule protein or peptide having a costimulatory molecule activity can generally be raised in animals by multiple subcutaneous (sc) or intraperitoneal (ip) injections of a costimulatory molecule immunogen, such as the extracellular domain of the costimulatory molecule protein, and an adjuvant. For example, as described above, it may be useful to conjugate a costimulatory molecule (including fragments containing particular eptitope(s) of interest) to a protein that is immunogenic in the species to be immunized, e.g., keyhole limpet hemocyanin, serum albumin.

The route and schedule of the host animal or cultured antibody-producing cells therefrom can generally make use of established and conventional techniques for antibody stimulation and production. In an illustrative embodiment, animals are typically immunized against the immunogenic costimulatory molecule conjugates or derivatives by combining about 1 µg to 1 mg of conjugate with Freund's complete adjuvant and injecting the solution intradermally at multiple sites. One month later the animals are boosted with ⅕ to ¹⁄₁₀ the original amount of conjugate in Freund's complete adjuvant (or other suitable adjuvant) by subcutaneous injection at multiple sites. Seven to 14 days later, the animals are bled and the serum is assayed for anti-costimulatory molecule titer. Animals are boosted until the titer plateaus. Preferably, the animal is boosted with the conjugate of the same costimulatory molecule protein, but conjugated to a different protein and/or through a different cross-linking agent. Conjugates also can be made in recombinant cell culture as protein fusions. Also, aggregating agents such as alum can be used to enhance the immune response.

Such mammal-produced populations of antibody molecules are referred to as "polyclonal" because the population comprises antibodies with differing immunospecificities and affinities for a costimulatory molecule. The antibody molecules are then collected from the mammal and isolated by well known techniques such as, for example, by using DEAE Sephadex to obtain the IgG fraction. To enhance the specificity of the antibody, the antibodies may be purified by immunoaffinity chromatography using solid phase-affixed immunogen. The antibody is contacted with the solid phase-affixed immunogen for a period of time sufficient for the immunogen to immunoreact with the antibody molecules to form a solid phase-affixed immunocomplex. The bound antibodies are separated from the complex by standard techniques.

C. Monoclonal Anti-Costimulatory Molecule Antibodies. The term "monoclonal antibody" or "monoclonal antibody composition", as used herein, refers to a population of antibody molecules that contain only one species of an antigen binding site capable of immunoreacting with a particular epitope of a costimulatory molecule. A monoclonal antibody composition thus typically displays a single binding affinity for a particular costimulatory molecule protein with which it immunoreacts. Preferably, the monoclonal antibody used in the subject method is further characterized as immunoreacting with a costimulatory molecule derived from humans.

Monoclonal antibodies useful in the compositions and methods of the invention are directed to an epitope of a costimulatory molecule antigen, such that complex formation between the antibody and the costimulatory molecule antigen inhibits interaction of the costimulatory molecule with its natural ligand(s) on the surface of immune cells, thereby inhibiting costimulation of a T cell through the costimulatory molecule-ligand interaction. A monoclonal antibody to an epitope of a costimulatory molecule can be prepared by using a technique which provides for the production of antibody molecules by continuous cell lines in culture. These include but are not limited to the hybridoma technique originally described by Kohler and Milstein (1975, *Nature* 256:495–497), and the more recent human B cell hybridoma technique (Kozbor et al. (1983) *Immunol Today* 4:72), EBV-hybridoma technique (Cole et al. (1985), *Monoclonal Antibodies and Cancer Therapy*, Alan R. Liss, Inc., pp. 77–96), and trioma techniques. Other methods which can effectively yield monoclonal antibodies useful in the present invention include phage display techniques (Marks et al. (1992) *J Biol Chem* 16007–16010).

In one embodiment, the antibody preparation applied in the subject method is a monoclonal antibody produced by a hybridoma cell line. Hybridoma fusion techniques were first introduced by Kohler and Milstein (Kohler et al. *Nature* (1975) 256:495–97; Brown et al. (1981) *J. Immunol* 127:539–46; Brown et al. (1980) *J Biol Chem* 255:4980–83; Yeh et al. (1976) *PNAS* 76:2927–31; and Yeh et al. (1982) *Int. J. Cancer* 29:269–75). Thus, the monoclonal antibody compositions of the present invention can be produced by the following method, which comprises the steps of:

(a) Immunizing an animal with a costimulatory molecule. The immunization is typically accomplished by administering a costimulatory molecule immunogen to an immunologically competent mammal in an immunologically effective amount, i.e., an amount sufficient to produce an immune response. Preferably, the mammal is a rodent such as a rabbit, rat or mouse. The mammal is then maintained for a time period sufficient for the mammal to produce cells secreting antibody molecules that immunoreact with the costimulatory molecule immunogen. Such immunoreaction is detected by screening the antibody molecules so produced for immunoreactivity with a preparation of the immunogen protein. Optionally, it may be desired to screen the antibody molecules with a preparation of the protein in the form in which it is to be detected by the antibody molecules in an assay, e.g., a membrane-associated form of a costimulatory molecule. These screening methods are well known to those of skill in the art.

(b) A suspension of antibody-producing cells removed from each immunized mammal secreting the desired antibody is then prepared. After a sufficient time, the mouse is sacrificed and somatic antibody-producing lymphocytes are obtained. Antibody-producing cells may be derived from the lymph nodes, spleens and peripheral blood of primed animals. Spleen cells are preferred, and can be mechanically separated into individual cells in a physiologically tolerable medium using methods well known in the art. Mouse lymphocytes give a higher percentage of stable fusions with the mouse myelomas described below. Rat, rabbit and frog somatic cells can also be used. The spleen cell chromosomes encoding desired immunoglobulins are immortalized by fusing the spleen cells with myeloma cells, generally in the presence of a fusing agent such as polyethylene glycol (PEG). Any of a number of myeloma cell lines may be used as a fusion partner according to standard techniques; for example, the P3-NS1/1-Ag4-1, P3-x63-Ag8.653 or Sp2/O-Ag14 myeloma lines. These myeloma lines are available from the American Type Culture Collection (ATCC), Rockville, Md.

The resulting cells, which include the desired hybridomas, are then grown in a selective medium, such as HAT medium, in which unfused parental myeloma or lymphocyte cells eventually die. Only the hybridoma cells survive and can be grown under limiting dilution conditions to obtain isolated clones. The supernatants of the hybridomas are screened for the presence of antibody of the desired specificity, e.g., by immunoassay techniques using the antigen that has been used for immunization. Positive clones can then be subcloned under limiting dilution conditions and the monoclonal antibody produced can be isolated. Various conventional methods exist for isolation and purification of the monoclonal antibodies so as to free them from other proteins and other contaminants. Commonly used methods for purifying monoclonal antibodies include ammonium sulfate precipitation, ion exchange chromatography, and affinity chromatography (see, e.g., Zola et al. in *Monoclonal Hybridoma Antibodies: Techniques And Applications*, Hurell (ed.) pp. 51–52 (CRC Press 1982)). Hybridomas produced according to these methods can be propagated in vitro or in vivo (in ascites fluid) using techniques known in the art.

Generally, the individual cell line may be propagated in vitro, for example in laboratory culture vessels, and the culture medium containing high concentrations of a single specific monoclonal antibody can be harvested by decantation, filtration or centrifugation. Alternatively, the yield of monoclonal antibody can be enhanced by injecting a sample of the hybridoma into a histocompatible animal of the type used to provide the somatic and myeloma cells for the original fusion. Tumors secreting the specific monoclonal antibody produced by the fused cell hybrid develop in the injected animal. The body fluids of the animal, such as ascites fluid or serum, provide monoclonal antibodies in high concentrations. When human hybridomas or EBV-hybridomas are used, it is necessary to avoid rejection of the xenograft injected into animals such as mice. Immunodeficient or nude mice may be used or the hybridoma may be passaged first into irradiated nude mice as a solid subcutaneous tumor, cultured in vitro and then injected intraperitoneally into pristane primed, irradiated nude mice which develop ascites tumors secreting large amounts of specific human monoclonal antibodies.

Media and animals useful for the preparation of these compositions are both well known in the art and commercially available and include synthetic culture media, inbred mice and the like. An exemplary synthetic medium is Dulbecco's minimal essential medium (DMEM; Dulbecco et al. (1959) *Virol* 8:396) supplemented with 4.5 gm/l glucose, 20 mM glutamine, and 20% fetal calf serum. An exemplary inbred mouse strain is the BALB/c.

D. Humanized Anti-Costimulatory Molecule Antibodies. When antibodies produced in non-human subjects are used therapeutically in humans, they are recognized to varying degrees as foreign and an immune response may be generated in the patient. One approach for minimizing or eliminating this problem, which is preferable to general immunosuppression, is to produce chimeric antibody derivatives, i.e., antibody molecules that combine a non-human animal variable region and a human constant region. Such antibodies are the equivalents of the monoclonal and polyclonal antibodies described above, but may be less immunogenic when administered to humans, and therefore more likely to be tolerated by the patient.

Chimeric mouse-human monoclonal antibodies (i.e., chimeric antibodies) reactive with a costimulatory molecule can be produced, for example, by techniques recently developed for the production of chimeric antibodies. Humanized antibodies may be produced, for instance, by replacing an immunogenic portion of an antibody with a corresponding, but non-immunogenic portion. Accordingly, genes encoding the constant regions of the murine (or other species) anti-costimulatory molecule antibody molecule are substituted with genes encoding human constant regions. (Robinson et al., International Patent Publication PCT/US86/02269; Akira, et al., European Patent Application 184,187; Taniguchi, M., European Patent Application 171,496; Morrison et al., European Patent Application 173,494; Neuberger et al., PCT Application WO 86/01533; Cabilly et al., European Patent Application 125,023; Better et al. (1988 *Science* 240:1041–1043); Liu et al. (1987) *PNAS* 84:3439–3443; Liu et al. (1987) *J. Immunol.* 139:3521–3526; Sun et al. (1987 *PNAS* 84:214–218; Nishimura et al. (1987) *Canc. Res.* 47:999–1005; Wood et al. (1985) *Nature* 314:446–449; and Shaw et al. (1988) *J. Natl Cancer Inst.* 80:1553–1559). General reviews of "humanized" chimeric antibodies are provided by Morrison, S. L. (1985) *Science* 229:1202–1207 and by Oi et al. (1986) *BioTechniques* 4:214. Those methods include isolating, manipulating, and expressing the nucleic acid sequences that encode all or part of an immunoglobulin variable region from at least one of a heavy or light chain. Sources of such nucleic acid are well known to those skilled in the art and, for example, may be obtained from an anti-costimulatory molecule antibody producing hybridoma. The chimeric cDNA can then be cloned into an appropriate expression vector.

Suitable "humanized" antibodies can be alternatively produced by CDR or CEA substitution (The Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060).

E. Combinatorial Anti-Costimulatory Molecule Antibodies. Both monoclonal and polyclonal antibody compositions of the invention can also be produced by other methods well known to those skilled in the art of recombinant DNA technology. An alternative method, referred to as the "combinatorial antibody display" method, has been developed to identify and isolate antibody fragments having a particular antigen specificity, and can be utilized to produce monoclonal anti-costimulatory molecule antibodies, as well as a polyclonal anti-costimulatory molecule population (Sastry et al. (1989) *PNAS* 86:5728; Huse et al. (1989) *Science* 246:1275; and Orlandi et al. (1989) *PNAS* 86:3833). After immunizing an animal with a costimulatory molecule immunogen as described above, the antibody repertoire of the resulting B-cell pool is cloned. Methods are generally known for directly obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable regions from a number of murine antibodies (Larrick et al. (1991) Biotechniques 11: 152–156). A similar strategy can also been used to amplify human heavy and light chain variable regions from human antibodies (Larrick et al. (1991) *Methods: Companion to Methods in Enzymology* 2:106–110). The ability to clone human immunoglobulin V-genes takes on special significance in light of advancements in creating human antibody repertoires in transgenic animals (see, for example, Bruggeman et al. (1993) *Year Immunol* 7:33–40; Tuaillon et al. (1993) *PNAS* 90:3720–3724; Bruggeman et al. (1991) *Eur J Immunol* 21:1323–1326; and Wood et al. PCT publication WO 91/00906).

In an illustrative embodiment, RNA is isolated from activated B cells of, for example, peripheral blood cells, bone marrow, or spleen preparations, using standard protocols (e.g., U.S. Pat. No. 4,683,202; Orlandi, et al. *PNAS* (1989) 86:3833–3837; Sastry et al., *PNAS* (1989) 86:5728–5732; and Huse et al. (1989) *Science* 246:1275–1281.) First-strand cDNA is synthesized using primers specific for the constant region of the heavy chain(s) and each of the κ and λ light chains, as well as primers for the signal sequence. Using variable region PCR primers, the variable regions of both heavy and light chains are amplified, each alone or in combination, and ligated into appropriate vectors for further manipulation in generating the display packages. Oligonucleotide primers useful in amplification protocols may be unique or degenerate or incorporate inosine at degenerate positions. Restriction endonuclease recognition sequences may also be incorporated into the primers to allow for the cloning of the amplified fragment into a vector in a predetermined reading frame for expression.

The V-gene library cloned from the immunization-derived antibody repertoire can be expressed by a population of display packages, preferably derived from filamentous phage, to form an antibody display library. Ideally, the display package comprises a system that allows the sampling of very large variegated antibody display libraries, rapid sorting after each affinity separation round, and easy isolation of the antibody gene from purified display packages. In addition to commercially available kits for generating phage display libraries (e.g., the Pharmacia *Recombinant Phage Antibody System*, catalog no. 27-9400-01; and the Stratagene SurfZAP™ phage display kit, catalog no. 240612), examples of methods and reagents particularly amenable for use in generating a variegated anti-costimulatory molecule antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay et al. (1992) *Hum Antibody Hybridomas* 3:81–85; Huse et al. (1989) *Science* 246:1275–1281; Griffths et al. (1993) *EMBO J* 12:725–734; Hawkins et al. (1992) *J Mol Biol* 226:889–896; Clackson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; and Barbas et al. (1991) *PNAS* 88:7978–7982.

In certain embodiments, the V region domains of heavy and light chains can be expressed on the same polypeptide, joined by a flexible linker to form a single-chain Fv fragment, and the scFV gene subsequently cloned into the desired expression vector or phage genome. As generally described in McCafferty et al., *Nature* (1990) 348:552–554, complete $V_H$ and $V_L$ domains of an antibody, joined by a flexible $(Gly_4\text{-Ser})_3$ linker can be used to produce a single chain antibody which can render the display package separable based on antigen affinity. Isolated scFV antibodies immunoreactive with a costimulatory molecule can subsequently be formulated into a pharmaceutical preparation for use in the subject method.

F. Hybridomas and Methods of Preparation. Hybridomas useful in the present invention are those characterized as having the capacity to produce a monoclonal antibody which will specifically immunoreact with a costimulatory molecule. As described below, the hybridoma cell producing anti-costimulatory molecule antibody can be directly implanted into the recipient animal in order to provide a constant source of antibody. The use of immuno-isolatory devices to encapsulate the hybridoma culture can prevent immunogenic response against the implanted cells, as well as prevent unchecked proliferation of the hybridoma cell in an immunocompromised host. A preferred hybridoma of the present invention is characterized as producing antibody molecules that specifically immunoreact with a costimulatory molecule expressed on the cell surfaces of activated human B cells.

Methods for generating hybridomas that produce, e.g., secrete, antibody molecules having a desired immunospecificity, i.e., having the ability to bind to a particular costimulatory molecule, and/or an identifiable epitope of a costimulatory molecule, are well known in the art. Particularly applicable is the hybridoma technology described by Niman et al. (1983) *PNAS* 80:4949–4953; and by Galfre et al. (1981) *Meth. Enzymol.* 73:3–46.

In another exemplary method, transgenic mice carrying human antibody repertoires can be immunized with a human costimulatory molecule. Splenocytes from these immunized transgenic mice can then be used to create hybridomas that secrete human monoclonal antibodies specifically reactive with a human costimulatory molecule (see, e.g., Wood et al. PCT publication WO 91/00906, Kucherlapati et al. PCT publication WO 91/10741; Lonberg et al. PCT publication WO 92/03918; Kay et al. PCT publication 92/03917; Lonberg, N. et al. (1994) *Nature* 368:856–859; Green, L. L. et al. (1994) *Nature Genet.* 7:13–21; Morrison, S. L. et al. (1994) *Proc. Natl. Acad. Sci.* USA 81:6851–6855; Bruggeman et al. (1993) *Year Immunol* 7:33–40; Tuaillon et al. (1993) *PNAS* 90:3720–3724; and Bruggeman et al. (1991) *Eur J Immunol* 21:1323–1326).

The term antibody as used herein is intended to include fragments thereof which are also specifically reactive with a costimulatory molecule as described herein.

Antibodies can be fragmented using conventional techniques and the fragments screened for utility in the same manner as described above for whole antibodies. For example, F(ab')$_2$ fragments can be generated by treating antibody with pepsin. The resulting F(ab)$_2$ fragment can be treated to reduce disulfide bridges to produce Fab' fragments.

Antibodies made using these or other methods can be tested to determine whether they inhibit a costimulatory signal in a T cell using the methods described below.

In one embodiment the agent that inhibits a costimulatory signal in a T cell is an antibody which binds to at least two of B7-1, B7-2, and an ICOS ligand. In making such an antibody, for example, portions of the extracellular domain which are conserved between the two costimulatory molecules can be used as the immunogen. (See, e.g., Metzler et al. 1997 *Nat Struct. Biol.* 4:527; Hutloff et al. 1999. *Nature* 397:263; WO 98/38216).

In one embodiment, the agent which inhibits a costimulatory signal in a T cell is an antibody which binds to B7-1. Such antibodies are known in the art or can be made as set forth above using a B7-1 molecule or a portion thereof as an immunogen and screened using the methods set forth above or other standard methods. Examples of B7-1 antibodies include those taught in U.S. Pat. No. 5,747,034 and in McHugh et al. 1998. *Clin. Immunol. Immunopathol.* 87:50 or Rugtveit et al. 1997. *Clin Exp. Immunol.* 110:104.

In another embodiment, the agent which inhibits a costimulatory signal in a T cell is an antibody which binds to B7-2. Such antibodies are known in the art or can be made as set forth above using a B7-2 molecule or a portion thereof as an immunogen and screened using the methods set forth above or other standard methods. Examples of B7-2 antibodies include those taught in Rugtveit et al. 1997. *Clin Exp. Immunol.* 110:104; Y, Nozawa et al. 1993. *Journal of Pathology.* 169:309–315; and WO 96/40915.

In one embodiment, the agent which inhibits a costimulatory signed in a T cell is a combination of an antibody which binds to B7-1 and an antibody which binds to B7-2.

In yet other embodiments, the agent which inhibits a costimulatory signal in a T cell is an antibody which binds to CD28 or ICOS, but does not transduce a costimulatory signal to a T cell (e.g., an Fab fragment of an anti CD28 or anti ICOS antibody). Such antibodies are known in the art or can be made as set forth above using a CD28 or ICOS molecule or a portion thereof as an immunogen and screened using the methods set forth above or other standard methods. Examples of known anti-CD28 antibodies include those taught by Darling et al. 1997. *Gene Ther.* 4:1350.

In preferred embodiments, Fab fragments of an antibody which binds to CD28 or ICOS can be used. Such antibody fragments, which are unable to crosslink CD28 or ICOS on the surface of a T cell, have been found to block T cell costimulation (Walunas et al. 1994. *Immunity* 1:405).

In yet other embodiments, the agent which inhibits a costimulatory signal in a T cell is an antibody which binds to CTLA4, which blocks a costimulatory signal in a T cell by delivering a negative signal to the T cell (i.e., which is a CTLA4 agonist). For example, crosslinking CTLA4 on the surface of a T cell has been shown to inhibit proliferation and IL-2 production (Krummel and Allison. 1996. *J. Exp. Med.* 183:2533). Such antibodies can be made as set forth above using a CTLA4 molecule or a portion thereof as an immunogen and screened using the methods set forth above or other standard methods. Exemplary antibodies are also taught e.g., in Vandenborre et al. 1998. *Am. J. Pathol.* 152:963.

III. Agents That Regulate the Expression of Costimulatory Molecules

In another embodiment, an agent that inhibits a costimulatory signal in a T cell is an agent that interferes with the expression of a costimulatory molecule. For example, interactions between CD40 on antigen presenting cells and CD40 ligand (CD40L) on T cells have been found to be important in sustaining, enhancing, or prolonging the expression of B7-1 or B7-2 on antigen presenting cells, resulting in enhanced costimulation (Van Gool, et al. 1996. *Immunol. Rev.* 153:47; Klaus et al. 1994. *J. Immunol.* 152:5643).

In one embodiment, the agent which blocks the expression of a costimulatory molecule, thus blocking a costimulatory signal in a T cell is a soluble form of CD40 or CD40L. DNA sequences encoding these CD40 and CD40L are known in the art, see e.g., GenBank Accession Nos. Y10507 or Stamenlovic et al. 1988. *EMBO J.* 7:1053–1059 for CD40 or Gauchat et al. 1993. *FEBS* 315(3):259–266; Graf et al. 1992. *Eur. J. Immunol.* 22:3191–3194; Seyama 1996. *Hum. Genet.* 97:180–185 or GenBank Accession Nos. L07414, X67878, X96710 for CD40L.

A soluble CD40 or CD40L molecule comprises at least a portion of CD40 or CD40L such that the interaction between CD40 on an APC and CD40L on a T cell is interrupted and the delivery of a costimulatory signal to a T cell is inhibited, e.g., by inhibiting the expression of a costimulatory molecule. In preferred embodiments, a soluble CD40 or CD40L protein comprises the extracellular domain of CD40 or CD40L. In one embodiment, a soluble, recombinant form of the extracellular domain of CD40 or CD40L protein can be made recombinantly or can be expressed as a fusion protein which comprises an extracellular portion of CD40 or CD40L and a second peptide. For example, the CD40 or CD40L fusion protein can comprise a CD40 or CD40 extracellular domain which is fused at the amino terminus to a signal peptide, e.g., from oncostatin M (see e.g., WO93/00431). In a particularly preferred embodiment, a soluble form of CD40 or CD40L is a fusion protein comprising the extracellular domain of CD40 or CD40L fused to a portion of an immunoglobulin molecule (e.g., Chen et al. 1995. *J. Immunol.* 155:2833). Such a fusion protein, a CD40Ig or a CD40Ig, can be made using methods known in the art (see e.g., Linsley 1994. *Perspectives in Drug Discovery and Design* 2:22 1; Linsley WO 93/00431, U.S. Pat. No. 5,770,197, U.S. Pat. No. 5,580,756, and U.S. Pat. No. 5,916,560).

In addition, antibodies to CD40 ligand have been found to synergize with agents which inhibit a costimulatory signal in a T cell to promote graft tolerance (Kirk et al. 1997. *Proc. Natl. Acad. Sci. USA* 94:8789; Larsen et al. 1996. *Nature* 381:434). Therefore, in one embodiment, antibodies to CD40 or CD40L which bind to these molecules, but which do not induce the expression of costimulatory molecules, can be used as an agent which inhibits a costimulatory signal in a T cell or can be used in conjunction with a second agent that inhibits a costimulatory signal in a T cell.

IV. Agents That Act Intracellularly to Inhibit a Costimulatory Signal

In one embodiment, the agent which inhibits a costimulatory signal in a T cell is an agent which acts intracellularly to inhibit such a signal. Stimulation of a T cell through the CD28 surface receptor (i.e., a costimulatory signal) leads to the production of D-3 phosphoinositides in a T cell. Therefore, in one embodiment, the production of D-3 phosphoinositides can be inhibited in a T cell to inhibit a costimulatory signal to thereby inhibit a T cell response, as measured, for example, by T cell proliferation and/or cytokine production. The term "D-3 phosphoinositides" is intended to include derivatives of phosphatidylinositol that are phosphorylated at the D-3 position of the inositol ring and encompasses the compounds phosphatidylinositol(3)-monophosphate (PtdIns(3)P), phosphatidylinositol(3,4)-bisphosphate (PtdIns(3,4)$P_2$), and phosphatidylinositol(3,4,5)-trisphosphate (PtdIns(3,4,5)$P_3$).

D-3 phosphoinositides are generated intracellularly by the activity of a phosphatidyl-inositol 3-kinase (PI3K). PI3K is a heterodimer composed of an 85 kDa subunit that binds tyrosyl-phosphorylated proteins via its SH2 domains and a 110 kDa catalytic subunit. PI3K was first identified as a lipid kinase that phosphorylates the D-3 position of the inositol ring of phosphatidylinositol, PtdIns (4)P, and PtdIns(4,5)P2. Two recent studies have demonstrated that PI3K is in fact a dual-specificity kinase that possesses both lipid and serine kinase activities (Dhand, R. et al. (1994) *EMBO J*. 13:522 and Carpenter, C. L. et al. (1993) *Mol. Cell Biol*. 13:1657).

Accordingly, in one embodiment, the agent which inhibits a costimulatory signal in a T cell is an agent which inhibits the activity of a PI3K. A preferred agent which inhibits PI3K activity in a T cell is the fungal metabolite wortmannin, or derivatives or analogues thereof. Wortmannin is a potent PI3K inhibitor derived from *T. Wortmannin* (Kyowa Hakko Kohyo Co. Ltd.) or from *P. fumiculosum* (Sigma). Wortmannin derivatives or analogues include compounds structurally related to wortmannin which retain the ability to inhibit PI3K and T cell responses. Examples of wortmannin derivatives and analogues are disclosed in Wiesinger, D. et al. (1974) *Experientia* 30:135–136; Closse, A. et al. (1981) *J. Med. Chem*. 24:1465–1471; and Baggiolini, M. et al. (1987) *Exp. Cell Res*. 169:408–418. Another inhibitor of PI3K activity that can be used is the bioflavenoid quercetin, or derivatives or analogues thereof. Quercetin derivatives or analogues include compounds structurally related to quercetin that retain the ability to inhibit PI3K and inhibit T cell responses. Examples of quercetin derivatives and analogues are disclosed in Vlahos, C. J. et al. (1994) *J. Biol. Chem*. 269:5241–5284. A preferred quercetin derivative which inhibits PI3K activity is LY294002 (2-(4-morpholinyl)-8-phenyl-4H-1-benzopyran-4-one, Lilly Indianapolis, Ind.) (described in Vlahos et al. cited supra).

CD28 stimulation has also been shown to result in protein tyrosine phosphorylation in a T cell (see e.g., Vandenberghe, P. et al. (1992) *J. Exp. Med*. 175:951–960; Lu, Y. et al. (1992) *J. Immunol*. 149:24–29). Accordingly, in one embodiment, an agent which inhibits a costimulatory signal in a T cell inhibits tyrosine phosphorylation in the T cell. A preferred protein tyrosine kinase inhibitor is one which inhibits src protein tyrosine kinases. In one embodiment, the src protein tyrosine kinase inhibitor is herbimycin A, or a derivative or analogue thereof. Derivatives and analogues of herbimycin A include compounds which are structurally related to herbimycin A and retain the ability to inhibit the activity of protein tyrosine kinases. In another embodiment, the agent which inhibits protein tyrosine phosphorylation is a protein tyrosine phosphatase or an activator of a protein tyrosine phosphatase. By increasing the tyrosine phosphatase activity in a T cell, the net amount of protein tyrosine phosphorylation is decreased. The protein tyrosine phosphatase can be a cellular protein tyrosine phosphatase within the T cell, such CD45 or Hcph. A cell surface tyrosine phosphatase on a T cell can be activated by contacting the T cell with a molecule which binds to the phosphatase and stimulates its activity. For example, an antibody directed against CD45 can be used to stimulate tyrosine phosphatase activity in a T cell expressing CD45 on its surface. Accordingly, in one embodiment, the agent which inhibits protein tyrosine phosphorylation within the T cell is an anti-CD45 antibody, or a fragment thereof which retains the ability to stimulate the activity of CD45. Examples of antibody fragments include Fab and F(ab')2 fragments. Antibodies, or fragments thereof, can be provided in a stimulatory form, for example multimerized or immobilized etc.

In addition, CD28 ligation has been associated with increased phospholipase C activity (see e.g., Nunes, J. et al. (1993) *Biochem. J*. 293:835–842) and increased intracellular calcium levels (see e.g. Ledbetter, J. A. et al. (1990) *Blood* 75:1531–1539 and the Examples). Accordingly, an agent which acts intracellularly to inhibit a costimulatory signal in a T cell can act by inhibiting phospholipase C activity and/or inhibiting an increase in intracellular calcium levels. For example, the tyrosine kinase inhibitor herbimycin A also inhibits CD28-induced calcium flux in T cells.

Protein serine and serine-threonine kinases have also been shown to be involved in signal transduction pathways associated with CD28 (Siegel, J. N. et al. (1993) *J. Immunol*. 151:4116–4127; Pai, S. V. et al. (1994) *J. Immunol*. 24:2364; Parry et al. 1997. *Eur. J. Immunol*. 27:2495). Thus, in another embodiment of the invention, an agent which acts intracellularly to inhibit a costimulatory signal in a T cell inhibits serine or serine-threonine kinase activity.

V. Other Agents That Block Costimulation of T Cells

Other agents which block a costimulatory signal in a T cell can be identified using standard techniques. For example, such agents can be identified by their ability to inhibit T cell proliferation and/or cytokine production, for instance, using a costimulation assay system can be used. In such a system, human $CLTA4^+$, $CD28^+$ and/or $ICOS^+$ T cells are isolated for example, by immunomagnetic bead depletion using monoclonal antibodies directed against B cells, natural killer cells and macrophages as previously described (Gimmi, C. D., et al. (1993) *Proc. Natl. Acad. Sci*. USA 90, 6586–6590). Antigen presenting cells, e.g., whole spleen cells, or purified B cells, or B7-1, B7-2, or ICOS ligand transfected cells can be irradiated or treated with mitomycin-C (e.g., at 25 $\mu$g/ml) for an appropriate period of time, and then extensively washed to inhibit proliferation. $10^5$ $CLTA4^+$, $CD28^+$ and/or $ICOS^+$ T cells can be incubated with, e.g., $10^5$–$10^4$ APCs, (e.g., cells transfected with a B7 molecule). In this exemplary assay, one population of the T cells receive a primary activation signal (e.g., a T cell receptor signal) alone; another population of T cells receive a costimulatory signal alone; yet another population of T cells receive both a primary activation signal and a costimulatory signal and yet another population of T cells both a primary activation signal and a costimulatory signal in the presence of the agent to be tested for its ability to block a costimulatory signal in a T cell. A primary activation signal can be delivered, e.g., by a submitogenic dose of PMA (e.g., Ing/ml), a submitogenic dose of mitogen, a suboptimal dose of antigen, or a submitogenic dose of anti-T cell receptor antibody or anti-CD3. Signal 2 is delivered by antigen presenting cells bearing a B7 molecule. Potential blocking agents can be tested at a range of concentrations. For example, potential blocking antibodies can be used as hybridoma supernatants or as purified antibody (e.g., at about 10 $\mu$g/ml). Proliferation of T cells can be measured by $^3$H-thymidine (1 $\mu$Ci) incorporation for the last 12–18 hours of a 72 hour incubation. The delivery of a primary activation signal should result in some proliferation, but T cells receiving both the primary activation signal and costimulatory signal 2, signals should proliferate maximally. Blocking agents are identified by their ability to reduce the maximal, costimulatory signal induced proliferation.

In addition to, or as an alternative to measuring T cell proliferation, T cell cytokine production can be measured using techniques which are well known in the art. For example, IL-2 and IL-4 produced in the T cell cultures can be assayed in culture supernatants collected at 24–72 hours after initiation of the culture using a commercially available ELISA (R&D Systems, Minneapolis, Minn. and BioSource, Camarillo, Calif.). As set forth above, blocking agents can be identified by their ability to reduce the maximal, costimulatory signal induced cytokine production.

VI. Administration of Agents

Administration of the compositions and/or agents described herein can be in any pharmacological form that includes a therapeutically active amount of an agent and optionally a pharmaceutically acceptable carrier. Administration of a therapeutically active amount of the subject agents and/or compositions is defined as an amount effective, at dosages and for periods of time necessary to reduce an immune response by a subject to an embryo, preferably an amount which enables a subject to carry one or more embryos to term. A therapeutically active amount of an agent or composition may vary according to factors such as the age, and weight of the individual, and whether or not the individual has had a previous exposure to fetal or paternal antigen or has had a previous spontaneous abortion. Such an amount can be readily determined by one of ordinary skill in the art.

The optimal course of administration of the agents and/or compositions may also vary depending upon the subject to be treated.

For example in one embodiment, an agent which blocks a costimulatory signal in a T cell is administered prior to fertilization. In another embodiment, the agent can be administered at the time of implantation (e.g., natural or unassisted implantation or at the time of embryo transfer). In another embodiment, the agent can be administered after implantation of the embryo into the uterine wall. In one embodiment, an agent which blocks a costimulatory signal is administered throughout the course of the pregnancy, e.g., beginning prior to fertilization, prior to implantation, or at about the time of implantation, and, e.g., ending when an immune response to the embryo is reduced or at the time of delivery. In one embodiment an agent that inhibits a costimulatory signal is administered prior to, during, and/or after a procedure employed to promote fertility or pregnancy. For example, in one embodiment, an egg or a fertilized embryo is suspended in a composition comprising an agent that inhibits a costimulatory signal in a T cell and is transferred into the uterus of a subject. In another embodiment, an agent that inhibits a costimulatory signal in a T cell is applied topically in the uterus prior to and/or after embryo transfer. In one embodiment, an agent that inhibits a costimulatory signal in a T cell is administered systemically instead of or in addition to being administered directly to the uterus or vaginally.

A dosage regime may be adjusted to provide the optimum therapeutic response for each subject without undue experimentation. For example, an immune response by a subject to an embryo antigen or a paternal antigen can be measured using standard techniques. Either humoral or cellular maternal immune responses can be assayed. For example, antibody titer to such antigens can be tested. Additionally or alternatively, cellular responses, e.g., T helper cell proliferation and/or cytokine production or cellular cytotoxicity can be tested. Immune cells can be removed from the female, e.g., peripheral blood lymphocytes, and tested for responsiveness to fetal or paternal antigen. For example, if an immune response to fetal or paternal antigens (when compared with immune responses of control cells, preferably cells that were removed from the same individual and stored prior to the pregnancy) are the same as or higher than control responses, more doses of an agent which blocks a costimulatory signal in a T cell may be administered. If an immune response to an embryo or a paternal antigen is reduced when compared to control immune responses, the dose of agent which blocks a costimulatory signal in a T cell can be reduced.

Downregulation of an immune response in a subject includes inhibiting or blocking an immune response already in progress or may involve preventing the induction of an immune response. The functions of activated T cells may be inhibited by suppressing T cell responses or by inducing specific tolerance in T cells, or both. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent. In a preferred embodiment, tolerance to embryo and/or paternal antigens is induced using the instant methods.

Downmodulation of immune responses can be demonstrated, e.g., by a showing of a reduction in antibody titers in a subject to an embryo or paternal antigen, by a reduction in cellular reactivity against an embryo, e.g., macrophage and/or NK cell infiltrate in the decidua. Additionally or alternatively a reduction in the numbers and/or activity of T cells specific for embryo and/or paternal antigens can be measured. Numbers of T cells specific for a given antigen can be determined, e.g., using a standard limiting dilution assay. T cell activity can be determined, e.g., by stimulating T cells from a subject in vitro with a embryo or paternal antigen (e.g., using whole cells originating from the embryo or the father, using a preparation comprising a mixture of antigens or using a purified antigen preparation) in association with an MHC class II molecule, and a costimulatory signal, e.g., provided by a stimulatory form of a B7 antigen, for instance a B7 antigen on a cell or by a soluble, stimulatory form of the peptide. Known cytokines released into the media can be identified, for example by measuring an increase in transcription of a cytokine gene, measuring proliferation and/or differentiation of cells that are responsive to a particular cytokine, or by a number of other methods using techniques that are well known in the art.

An agent that inhibits a costimulatory signal in a T cell can be administered in the form of a pharmaceutical composition suitable for administration. Such compositions typically comprise the agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, they may be used in the instant composition. Supplementary active compounds can also be incorporated into the compositions.

A pharmaceutical composition of the invention is formulated to be compatible with its intended route of administration. For example, solutions or suspensions used for parenteral, intradermal, topical, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

In one embodiment an agent which blocks a costimulatory signal is formulated into a suppository for vaginal use. These can be prepared by mixing the agent with a suitable non-irritating carrier which is solid at room temperature but liquid at rectal temperature and therefore will melt in the vagina to release the drug. Such materials include cocoa butter, beeswax, polyethylene glycols, a suppository wax or a salicylate, and which is solid at room temperature, but liquid at body temperature and, therefore, will melt in the vaginal cavity and release the active agent.

Compositions which are suitable for vaginal administration also include pessaries, tampons, creams, gels, pastes, foams, films, or spray compositions containing such carriers as are known in the art to be appropriate. The carrier employed should be compatible with vaginal administration. Combinations can be, e.g., in solid, semi-solid and liquid dosage forms, such as douches, foams, films, ointments, creams, balms, gels, salves, pastes, slurries, vaginal suppositories, or sexual lubricants.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition will be sterile and should be fluid to the extent that easy syringability exists. Preferably, it will be stable under the conditions of manufacture and storage and will be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the agent in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially, e.g., from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active agent or composition for the treatment of individuals. Appropriate dosages can readily be determined by one of ordinary skill in the art.

VII. Methods of the Invention

As described in Examples 10 and 11 (and shown in FIGS. 5 and 6), the expression levels of many genes (e.g., adhesion molecules, inflammatory cytokines, and immune cell surface antigens) are altered during pathologic pregnancy.

Accordingly, the methods of the present invention include prognostic and diagnostic methods and methods which determine whether treatment of a subject is having the desired effect (hereinafter "treatment monitoring methods"). Prognostic methods include methods which determine whether subjects are at risk for developing a spontaneous abortion. Diagnostic methods include methods which determine whether a subject is suffering from a spontaneous abortion.

The methods of the present invention can be used alone or can be used with other techniques or methods. For example, the terms "diagnostic method" and "prognostic method" are intended to include methods which facilitate the diagnosis or prognosis of a subject.

The treatment monitoring methods can be used alone or in conjunction with other methods. The "desired effect" includes at least one effect capable of providing an indication of the ability of the treatment methods of the invention to treat a subject. For example, the desired effect may be prevention of spontaneous abortion. The desired effect may also be a determination that the level of one or more of an adhesion molecule, an inflammatory cytokine, and/or an immune cell surface molecule determined from a biological sample from the subject is normal.

One embodiment of the present invention provides a method of diagnosing a subject who is at increased risk for or is suffering from immune-mediated spontaneous abortion, which includes determining the expression levels of one or more of the following genes in a tissue, cell, or biological fluid sample from a subject (e.g., a pregnant subject): an adhesion molecule (e.g., VCAM-1, P-selectin, or E-selectin), an inflammatory cytokine (e.g., IL-2, IL-10, IL-12, IL-11, TNFα, EL-1β, TGF, RANTES, IL-6, or IFN-γ), and/or an immune cell surface antigen (e.g., B7.1 (CD80), B7.2 (CD86), CD4, CD8, GL50, or ICOS). In a preferred embodiment, the level of one or more of said genes in maternal serum or blood is determined. In a further preferred embodiment, the level of one or more said genes is determined in a placental sample. The level of one or more of said genes may also be determined from an amniotic fluid sample or from a tissue sample such as a chorionic villous sample.

In one embodiment, the invention provides a method for detecting the presence of one or more of said genes in a biological sample. The method involves contacting the biological sample with an agent capable of detecting protein or nucleic acid molecules (e.g., mRNA) such that the presence of one or more of said genes is detected in the biological sample. One agent for detecting mRNA is a labeled or labelable nucleic acid probe capable of hybridizing specifically to the mRNA of a particular gene. The nucleic acid probe can be, for example, the full-length cDNA, or a portion thereof, such as an oligonucleotide of at least 15, 30, 50, 100, 250 or 500 nucleotides in length and is sufficiently complimentary to specifically hybridize under stringent conditions to the particular mRNA. Probes can be designed using the publicly available sequences, determined by searching using the Genbank Accession Numbers: X53051 (human VCAM-1); NM_003005 (human P-selectin); NM_000450 (human E-selectin); HSIL05 (human IL-2 gene); X78437 (human IL-10); AF180562 and AF180563 (human IL-12); NM_000881 (human IL-11); U42625 (human TNFα); M 15840 (human IL-1β) NM_003236 (human TGFα); M60315 (human TGFβ); L10918 (human RANTES); M54894 (human IL-6); J00219 (human IFN-γ); NM_005191 (human B7.1/CD80); U04343 (human B7.2/CD86); M35160 (human CD4); M36712 (human CD8); AF 199028 (human GL50); or AF218312 (human ICOS). Sequences for any of the aforementioned genes from species other than humans may be obtained by searching GenBank using the desired gene name and the name of the desired organism.

In a preferred embodiment, mRNA in a sample is determined using the Perkin Elmer Taqman EZ RT-PCR kit (Perkin Elmer), as described in Example 11. Gene specific primers and probes can be designed using Primer Express software (Perkin Elmer) and the gene sequences described above by Accession number.

A preferred agent for detecting a particular protein (e.g., an adhesion molecule, an inflammatory cytokine, or an immune cell surface antigen) is a labeled or labelable antibody capable of binding to that specific protein. Antibodies can be polyclonal, or more preferably, monoclonal. An intact antibody, or a fragment thereof (e.g., Fab or F(ab')$_2$) can be used. The term "labeled or labelable", with regard to the probe or antibody, is intended to encompass direct labeling of the probe or antibody by coupling (i.e., physically linking) a detectable substance (e.g., $^{125}$I) to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

As used herein, the term "biological sample" refers to a sample of biological material isolated from a subject, preferably a human subject, or present within a subject, preferably a human subject. The "biological material" can include, for example, tissues, tissue samples, tumors, tumor samples, cells, biological fluids, and purified and/or partially-purified biological molecules. As used herein, the term "isolated", when used in the context of a biological sample, is intended to indicate that the biological sample has been removed from the subject. In one embodiment, a biological sample comprises a sample which has been isolated from a subject and is subjected to a method of the present invention without further processing or manipulation subsequent to its isolation. In another embodiment, the biological sample can be processed or manipulated subsequent to being isolated and prior to being subjected to a method of the invention. For example, a sample can be refrigerated (e.g., stored at 4° C.), frozen (e.g., stored at −20° C., stored at −135° C., frozen in liquid nitrogen, or cryopreserved using any one of many standard cryopreservation techniques known in the art). Furthermore, a sample can be purified subsequent to isolation from a subject and prior to subjecting it to a method of the present invention. As used herein, the term "purified" when used in the context of a biological sample, is intended to indicate that at least one component of the isolated biological sample has been removed from the biological sample such that fewer components, and consequently, purer components, remain following purification. For example, a serum sample can be separated into one or more components using centrifugation techniques known in the art to obtain partially-purified sample preparation. Furthermore, it is possible to purify a biological sample such that substantially only one component remains. For example, a tissue or tumor sample can be purified such that substantially only the protein or mRNA component of the biological sample remains.

Furthermore, it may be desirable to amplify a component of a biological sample such that detection of the component is facilitated. For example, the mRNA component of a biological sample can be amplified (e.g., by RT-PCR) such that detection of mRNA is facilitated. As used herein, the term "RT-PCR" ("reverse transcriptase-polymerase chain reaction") includes subjecting mRNA to the reverse transcriptase enzyme resulting in the production of DNA which is complementary to the base sequences of the mRNA. Large amounts of selected cDNA can then be produced via the polymerase chain reaction which relies on the action of heat-stable DNA polymerase for its amplification action. Alternative amplification methods include, but are not limited to, self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et all, 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

The detection methods of the present invention can be used to detect protein or nucleic acid molecules in a biological sample in vitro as well as in vivo. For example, in vitro techniques for detection of mRNA include Northern hybridizations and in situ hybridizations. In vitro techniques for detection of protein include enzyme linked immunosorbent assays (ELISAs), Western blots, immunoprecipitations and immunofluorescence.

In order to determine if the level of one or more of an adhesion molecule, an inflammatory cytokine, and/or an immune cell surface antigen in a biological sample from a test subject is abnormal, the level of one or more of an adhesion molecule, an inflammatory cytokine, and/or an immune cell surface antigen from the test subject is compared, for example, to the average level of those molecules determined from women who have had normal pregnancies. If the level of those molecules determined in the test subject is higher (i.e., statistically significantly higher) than the levels for normal pregnancies, the test subject is diagnosed as being at risk for developing immune-mediated spontaneous abortion.

In one embodiment, a subject having a 1–10% increase in the level of one or more of an adhesion molecule, an inflammatory cytokine, and/or an immune cell surface antigen is diagnosed as being at risk for preeclampsia. In another embodiment, a subject having a 10–20% increase in the level of one or more of an adhesion molecule, an inflammatory cytokine, and/or an immune cell surface antigen is diagnosed as being at risk. In yet another embodiment, a subject having a 20–30%, 30–40%, 40–50%, 50–100%, 100–200%, 200–400% (e.g., 2-fold to 4-fold), to 10-fold, 10-fold to 100-fold, 100-fold or greater increased levels, for example, when compared to a suitable or appropriate control, is diagnosed as being at risk for immune-mediated spontaneous abortion.

The present invention also comprises kits for detecting the presence of one or more of an adhesion molecule, an inflammatory cytokine, and/or an immune cell surface antigen in a biological sample. For example, the kit can comprise a labeled or labelable agent capable of detecting mRNA or polypeptide of one or more of an adhesion molecule, an inflammatory cytokine, and/or an immune cell surface antigen in a biological sample and a means for determining the amount of mRNA or polypeptide of one or more of an adhesion molecule, an inflammatory cytokine, and/or an immune cell surface antigen in a biological sample. The agent can be packaged in a suitable container. The kit can further comprise a means for comparing the amount of one or more of an adhesion molecule, an inflammatory cytokine, and/or an immune cell surface antigen in the sample with a standard (e.g., a chart showing normal and abnormal ranges for levels one or more of an adhesion molecule, an inflammatory cytokine, and/or an immune cell surface antigen, or a sample of a suitable or appropriate control) and/or can further comprise instructions for using the kit to detect mRNA or polypeptide of one or more of an adhesion molecule, an inflammatory cytokine, and/or an immune cell surface antigen.

It may also be desirable to use the methods of the present invention, as described above, to monitor the progress of treatment of a subject. For example, a subject (e.g., a human) may be undergoing treatment for immune-mediated spontaneous abortion using any one of the methods of treatment described herein. The methods described above for diagnosis may be used to determine if the level of one or more of an adhesion molecule, an inflammatory cytokine, and/or an immune cell surface antigen has returned to a normal level. Treatment of the subject can then be modified (e.g., increased or decreased) depending on the results.

The practice of the present invention will employ, unless otherwise indicated, conventional techniques of cell biology, cell culture, molecular biology, microbiology, recombinant DNA, and immunology, which are within the skill of the art. Such techniques are explained fully in the literature. See, for example, *Genetics; Molecular Cloning A Laboratory Manual*, 2nd Ed., ed. by Sambrook, J. et al. (Cold Spring Harbor Laboratory Press (1989)); *Short Protocols in Molecular Biology*, 3rd Ed., ed. by Ausubel, F. et al. (Wiley, N.Y. (1995)); *DNA Cloning*, Volumes I and H (D. N. Glover ed., 1985); *Oligonucleotide Synthesis* (M. J. Gait ed. (1984)); Mullis et al. U.S. Pat. No: 4,683,195; *Nucleic Acid Hybridization* (B. D. Hames & S. J. Higgins eds. (1984)); the treatise, *Methods In Enzymology* (Academic Press, Inc., N.Y.); *Immunochemical Methods In Cell And Molecular Biology* (Mayer and Walker, eds., Academic Press, London (1987)); *Handbook Of Experimental Immunology*, Volumes I–IV (D. M. Weir and C. C. Blackwell, eds. (1986)); and Miller, *J. Experiments in Molecular Genetics* (Cold Spring Harbor Press, Cold Spring Harbor, N.Y. (1972)).

The contents of all references, pending patent applications and published patents, cited throughout this application are hereby expressly incorporated by reference.

The invention is further illustrated by the following examples, which should not be construed as further limiting.

EXAMPLES

Developing mouse hematopoietic yolk sacs were examined for the presence of costimulatory receptors. Flow cytometric analysis revealed a $CTLA4^+$, $PECAM-1^+$, CD45- subpopulation of cells within dispersed yolk sac tissues as early as day 8.5 of embryonic development. Whole mount tissue immunohistochemistry localized CTLA4 staining to blood islands and vasculature of yolk sac cells, soluble B7-1 binding to yolk sac cells was inhibited by anti-CTLA4 antibodies, demonstrating the potential of yolk sac CTLA4 to recognize B7-1 as a cognate ligand. RT-PCR of mRNA prepared from yolk sac and maternal spleen yielded specific products when PCR primers specific for the extracellular domain of CTLA4 were used. Collagenase digestion of yolk sac tissues resulted in the elimination of anti-CTLA4 antibody staining, demonstrating yolk sac CTLA4 to be secreted protein associated with the extracellular matrix.

To test whether a soluble/extracellular form of CTLA4 may have a role in maternal tolerance of the embryo, the effects of exogenously applied mCTLA4-Ig fusion protein were examined on an abortion prone mouse model (DBA× CBA). Administration of two 200 ug doses of CTLA4 Ig per mouse delivered intraperitoneally on days 4 and 6 of gestation revealed a reduction of spontaneous abortion from naturally occurring mean high levels (21%) to mean background levels (8%). These results indicate that yolk sac extracellular CTLA4 functions as an immunoprotective agent in tolerizing the maternal immune system against embryo during development, and suggests the possible use of soluble CTLA4 to ameliorate spontaneous abortions in humans.

Additionally, evidence suggests elevated placental and plasma cytokines (such as TNF-α, IFN-γ, and IL-2), in conjunction with NK cell and macrophage infiltration into the placental bed, may lead to endothelial cell activation and dysfunction in the placental bed, contributing to placental resorption/fetal loss and/or intrauterine growth retardation. Using the model of CBA (female) X DBA/2 (male) mating combination for murine pathologic pregnancy, treatment of mice with mCTLA4-IgG2am decreased fetal resorption and intrauterine growth retardation. Use of an in vivo dual radioisotope perfusion regimen that $^{125}I$ labeled VCAM antibody bound to resorbing placental tissue at a level two-fold higher than non-resorbing placental tissue. RT-PCR (Taqman™) analysis confirmed reduced VCAM mRNA in non-resorbing while increased message was seen in resorbing tissue. Furthermore, gestational treatment of mice with mCTLA4-IgG2am decreased VCAM mRNA found in resorbing tissue compared to untreated animals. These findings suggest a role for VCAM expression as an indicator of pathology in murine fetal loss and by blocking the proinflammatory pathway for T-cell activation, the invention providse a potential mechanism for decreasing subsequent endothelial cell activation and dysfunction which contributes to fetal loss in pathologic pregnancies. Other genes, including cell-surface antigens and inflammatory cytokines, whose expression levels were altered in resorbing tissues were also modulated by treatment with CTLA4-Ig.

Materials and Methods Used in Examples 1–6
The Following Methods were used in Examples 1–6:

Tissue source/Mouse strains used. Mouse embryonic tissues used in this study were taken from timed pregnant strains CBA and Swiss Webster. No significant differences in CTLA4 surface phenotype profile were detected between yolk sacs of different mouse strains. Yolk sacs and embryos were removed from the uterus of sacrificed female mice between day 8.5 and day 14.5 post coitum. In spontaneous abortion mouse models, CBA female mice were allowed to copulate with either BALB/c (control matings) or DBA (abortion prone) males overnight. The following morning, female mice with vaginal plugs (day 0.5 of gestation) were removed and housed apart from male mice. Two hundred μg of purified CTLA4 Ig were injected into each mouse interperioneally on days 4 and 6 of gestation corresponding to the time of implantation and the time when primary maternal immune responses initiate. On day 12 of gestation, mice were sacrificed and uterine horns removed for analysis. Percentage of resorbed embryos were quantified and recorded for each mouse examined.

Flow cytometry. Yolk sacs were dispersed mechanically by successive passage through 16, 18 and 20 gauge needles in the presence of 10% rabbit serum, used as an antibody blocking reagent. Dispersed yolk sac cells were filtered through nylon mesh to remove debris prior to cell staining. Directly conjugated antibodies (Pharmingen) used-in this study are listed in Table 1. FITC-conjugated mouse B7-1-Ig fusion proteins were prepared at Genetics Institute. Propidium iodide was added prior to data acquisition for the fluorescent exclusion of dead cells. Data were collected on a Becton Dickenson FACScan flow cytometer using CellQuest software. For stringent analysis of collected data, the first 70 percentile peak of PI negative cells was gated for all plots presented in this study. In crossblocking experiments, yolk sac cells were preincubated with either 100 ug/ml unlabeled anti-CTLA4 antibody (Clone UC-4F10-11) or 100 μg/ml of control hamster Ig for 10 min. prior to the addition of 2 μg/ml B7-1-Ig FITC and incubation for 20 min. at 4° C. Cells were washed in 2% fetal calf serum in PBS and stained with propidium iodide prior to FACS.

TABLE 1

Antibodies Used In These Examples

| Antibody (Tag) | Clone | Epitope/Function |
| --- | --- | --- |
| Anti-CD152 (PE) | UC-4F10-11 Lot M019369 | CTLA4, surface receptor for B7 proteins |
| Anti-CD31 (FITC) | Mec 13.3 | PECAM-1, endothelial adhesion molecule |
| Anti-CD45 (FITC) | 30-11 | CD45, leukocyte common antigen-phosphatase |
| Anti-CD44 (FITC) | IM7 | CD44, hyaluronic acid binding protein |

RNA analysis. Total RNA was prepared from isolated tissues and cells using RNAStat-60 (Teltest B, Friendswood, Tex.). Poly-A RNA enrichment was performed using Promega PolyAttract System (Promega, Madison, WI) according to manufacture's protocol. To lessen the possibility of contaminating genomic DNA, RNA was treated with RQ-1 DNAse (Promega) prior to RT-PCR reactions. First strand synthesis and thermocycling conditions used were as suggested by the manufacturer (Gibco-BRL, Bethesda, Md.). Reverse transcription was performed using oligo $dT_{(12)}$ primers for first strand extension and SuperScript reverse transcriptase in 40 ul reactions according to manufacturer's protocol. Completed first strand cDNA products were heat inactivated at 70° C. for 10 min and then stored at −20° C. One microliter of first strand cDNA was used as amplification template for 100 pl PCR reactions of 50 pm each DNA primer (Table 2), in 50 mM KCl, 10 mM Tris HC1, pH 9.0, 0.1% Triton X-100, 1.5 mM MgC12, 1 mM dNTPs and 2–5 units of Taq polymerase (Promega). Thermocycling reactions were performed with 42 cycles of 94° C., I min., 55° C. 1 min, and 72° C. 1 min in a Robobcycler thermocycling device (Stratagene). Five microliters of completed PCR reactions were loaded onto 1.5% agarose minigels and electrophoresed. Amplification products were visualized by ethidium bromide staining.

Example 1

Flow Cytometry of Yolk Sac Cells

Figure 1B:
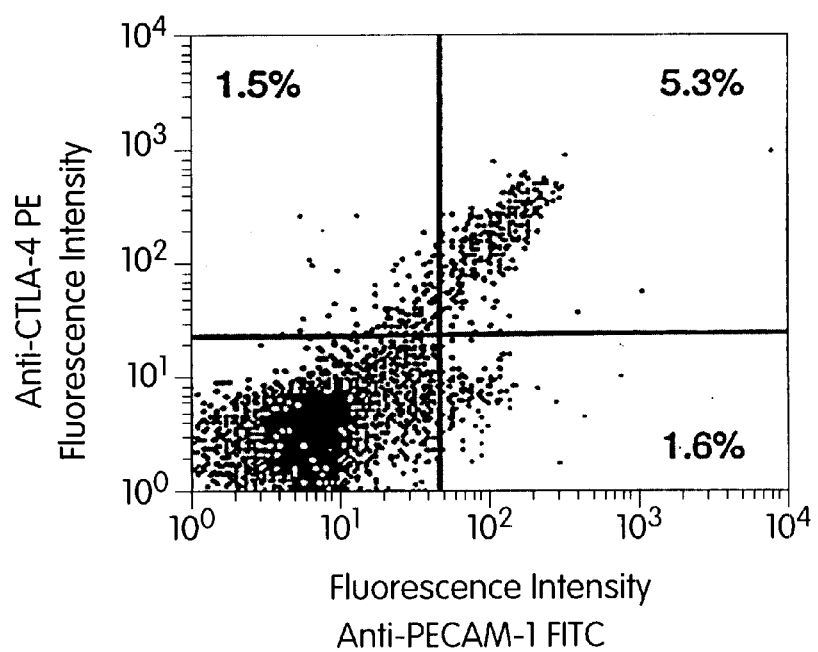

The yolk sac is the initial site of angiogenesis and hematopoiesis as evidenced by the generation of blood islands on days 7.5–8 of development. During the successive two days in development, a yolk sac vascular system is established in which blood islands are joined by capillary networks that eventually connect with the circulatory system of embryo proper (Jollie, 1990, *Teratology* 41. 361–81). To assess whether yolk sac cells displayed the costimulatory receptor CTLA4, mechanically dispersed day 8.5 yolk sac cells were stained with antibodies against CTLA4, and also with antibodies against the vascular endothelial/ hemeangiogenic market PECAM-1 and pan leukocyte marker CD45. In samples stained with both anti-PECAM-1-FITC antibody and anti-CTLA4PE antibody, a distinct subpopulation of double positive CTLA4+, PECAM-1+ yolk sac cells were detected, suggesting CTLA4 to be associated with cells of vascular origin (FIG. 1). In samples stained with anti-CD45 FITC and anti-CTLA4+ PE antibodies, two distinct single positive subpopulations were detected, with negligible numbers of cells bearing a double positive phenotype. The absence of CD45 staining suggests CTLA4 positive cells were not associated with leukocyte derived cells.

Example 2

Whole Mount in Situ Immunohistochemical Analysis of Day 11 Yolk Sac Membranes

Intact day 11 yolk sac membranes examined by whole mount in situ fluorescence immunohistochemistry revealed unambiguous fluorescence staining localized to blood islands and vasculature. No staining was detected on stromal cells outside these regions, indicating the accumulation of CTLA4 was specific to vascular/hematopoietic tissues. Control staining with irrelevant antibody resulted in diffuse low level background fluorescence. These results support the flow cytometric phenotype of CTLA4 positive cells being of hemeangiogenic origin.

Example 3

Binding of Yolk Sac Cells to B7-1 Ig Fusion Protein

Figure 2A:
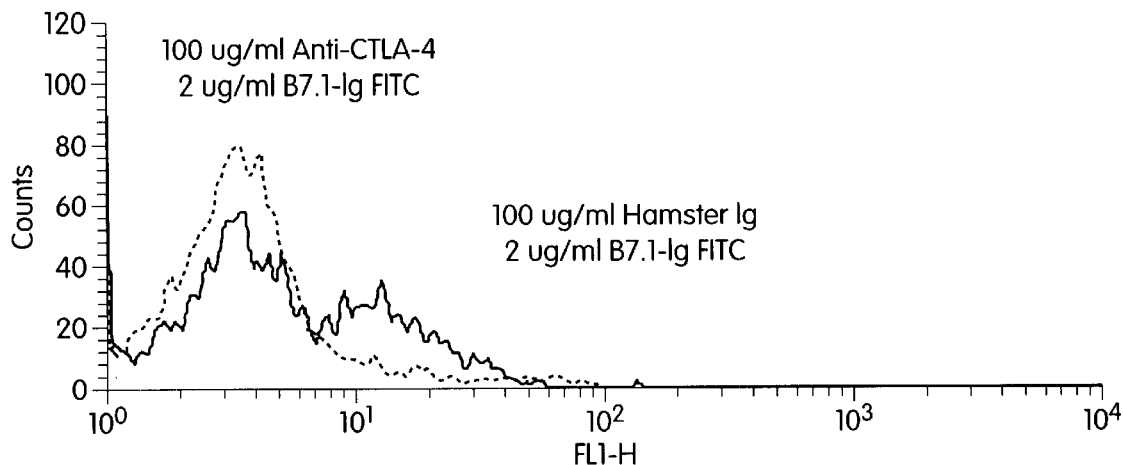
FIG. 2 shows a competition assay of B7.1-Ig fusion protein and anti-CTLA4 antibodies. Cells were preincubated with either control hamster Ig (100 ug/ml, solid lines) or anti-CTLA4 antibodies (100 ug/ml, dashed lines) prior to staining with B7.1-Ig FITC (2 ug/ml). Panel A shows yolk sac cells. Panel B shows CHO mCTLA4 gpi cells.
Figure 2B:
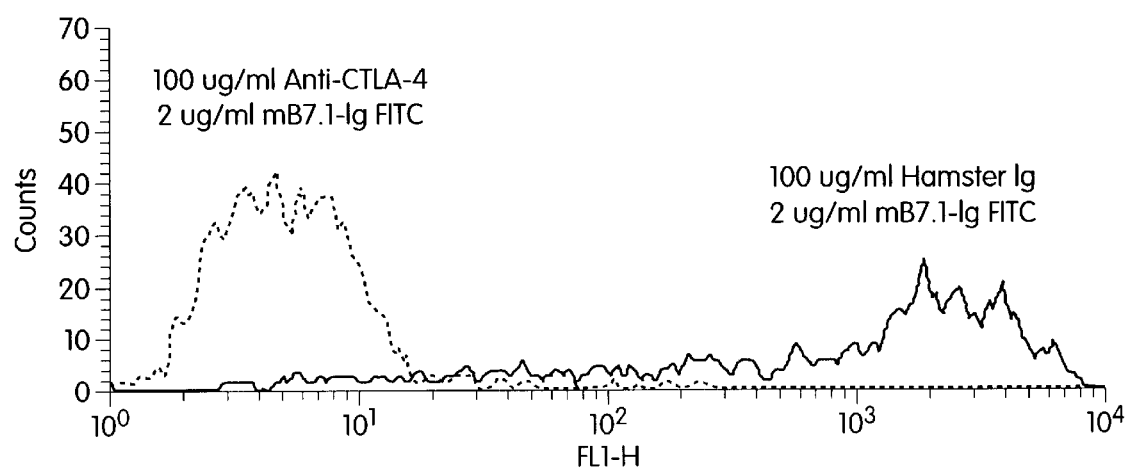

To assess the potential of yolk sac cells in binding its cognate ligand in soluble form, yolk sac cells were stained with directly conjugated B7.1 Ig-FITC. When either yolk sac cells or control CHO mCTLA4-gpi cells were preincubated with 100 ug/ml control hamster Ig followed by staining with 2 ug/ml B7.1Ig-FITC, positive cells were clearly detected in both cell types (FIG. 2). When yolk sac and CHO mCTLA4 gpi cells were preincubated with 100 ug/ml anti-CTLA4 antibody (clone UC-4F10-11) before the addition of 2 ug/ml B7.1Ig-FITC, however, no positive staining was observed for either cell type. These results demonstrate the functional ability of anti-CTLA4 blocking antibodies to compete with B7-1 binding to yolk sac cells, thus demonstrating yolk sac CTLA4 to be structurally functional in binding its cognate ligand in soluble form.

Table 2. Oligonucleotide Primers For Amplification of Sequences Within The Extracellular Region of CTLA4.

Example 4

Reverse Transcriptase-polymerase Chain Reaction Analysis of Yolk Sac RNA

To assess the potential of yolk sac cells to express CTLA4 throughout early embryonic development, RT-PCR analysis was performed on day 8.5, 12.5 and 14.5 yolk sac RNA using oligonucleotide primers within the V region for amplification of sequences within the extracellular region of CTLA4 (Table 2). When primers V1 and V2 were used, bands of approximately 200 bp were amplified and detected in all yolk sac timepoints examined as well as CHO-CTLA4 gpi positive control cell line. The size of this amplification product corresponded to the predicted size of 210 bp based on the murine CTLA4 cDNA sequence.

To address whether CTLA4 transcripts were of maternal or fetal origin, RT-PCR was performed on yolk sac of RAG −/− embryos, where no B or T cell lymphocytes are present, and on yolk sac of CTLA4 +/− heterozygous embryos in which the maternal genotype was CTLA4 −/−. Amplification products of CTLA4 were also detected in day 12.5 yolk sac of embryos. These results suggest that CTLA4 is normally produced by the embryo during yolk sac formation and was not derived from infiltrating maternal leukocytes. Actin primers were used as a positive PCR control.

Example 5

Association of Yolk Sac CTLA4 Protein With the Extracelllular Matrix

In T lymphocytes, most CTLA4 is present intracellulary as reported. Therefore, the detection of a bright population of CTLA4 positive cells associated with the yolk sac was not expected. CLTA-4 or an alternate form of CTLA4 may exist as a secreted protein localized in the extracellular matrix (See, e.g., GenBank Accession No: U90273, GenBank Accession No.: U90271; GenBank Accession No: U90270). To test the nature of the surface display on yolk sac CTLA4 positive cells, the effects of enzymatic removal of extracellular matrix prior to CTLA4 staining was examined. Mechanically dispersed day 12 yolk sacs and chemically dispersed CHO-CTLA4 gpi cells were incubated either in the presence or absence of collagenase, then stained with antibodies. In addition to staining for the presence of CTLA4, antibodies were used to detect CD44 antigen. CD44 is a broadly distributed extracellular matrix binding surface glycoprotein that is also found on embryonic tissues (Campbell et al., 1995, *Hum Reprod* 10, 425–30; Lesley et al., 1993, *Adv. Immnol.* 54, 271–335). CD44 exists in both soluble and intrinsic membrane spanning surface forms (Rokhlin and Cohen, 1996, *Caner Lett* 107, 29–35; Yu and Toole, 1996, *J Biol Chem* 271, 20603–7). By flow cytomeric analysis, non-collagenase treated yolk sac cells revealed a population of $CD44^+$, $CTLA4^+$ double positive cells (FIG. 3, R2) and a smaller population of single positive $CD44^+$,

| Name | Sequence | |
|---|---|---|
| V1 (VL012) | 247-CACAACACTGATGAGGTCCG-266 | (SEQ ID NO:2) |
| V2 (VL021) | 257-TGAGTTCCAC CTTGCAGAGG-438 | (SEQ ID NO:3) |
| Actin1 | 105-GTCGTCGACA ACGGCTCCG GCATGTG-130 | (SEQ ID NO:4) |
| Actin2 | 357-CATTGTAGAAGGTGTGGTGCCAGAT-333 | (SEQ ID NO:5) |

Figure 3A:
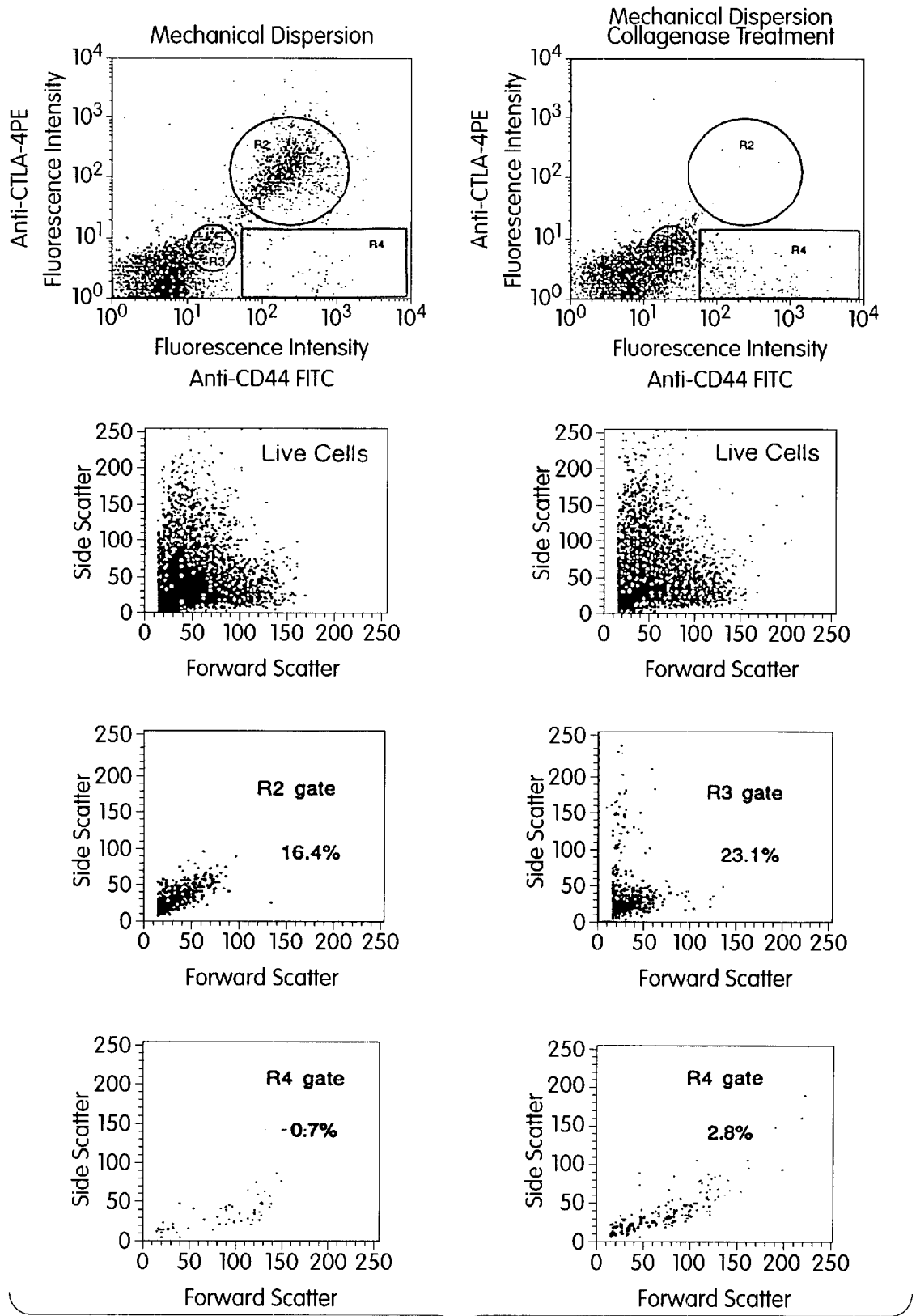
FIG. 3 shows effects of collagenase treatment on CTLA4 surface expression. Cells were incubated in either the presence or absence of collagenase, as indicated, followed by antibody staining. Panel A shows yolk sac cells with anti-CTLA4 PE, anti CD44-FITC antibodies. Panel B shows control CHO-mCTLA4 gpi cells stained with anti-CTLA4 PE.
Figure 3B:
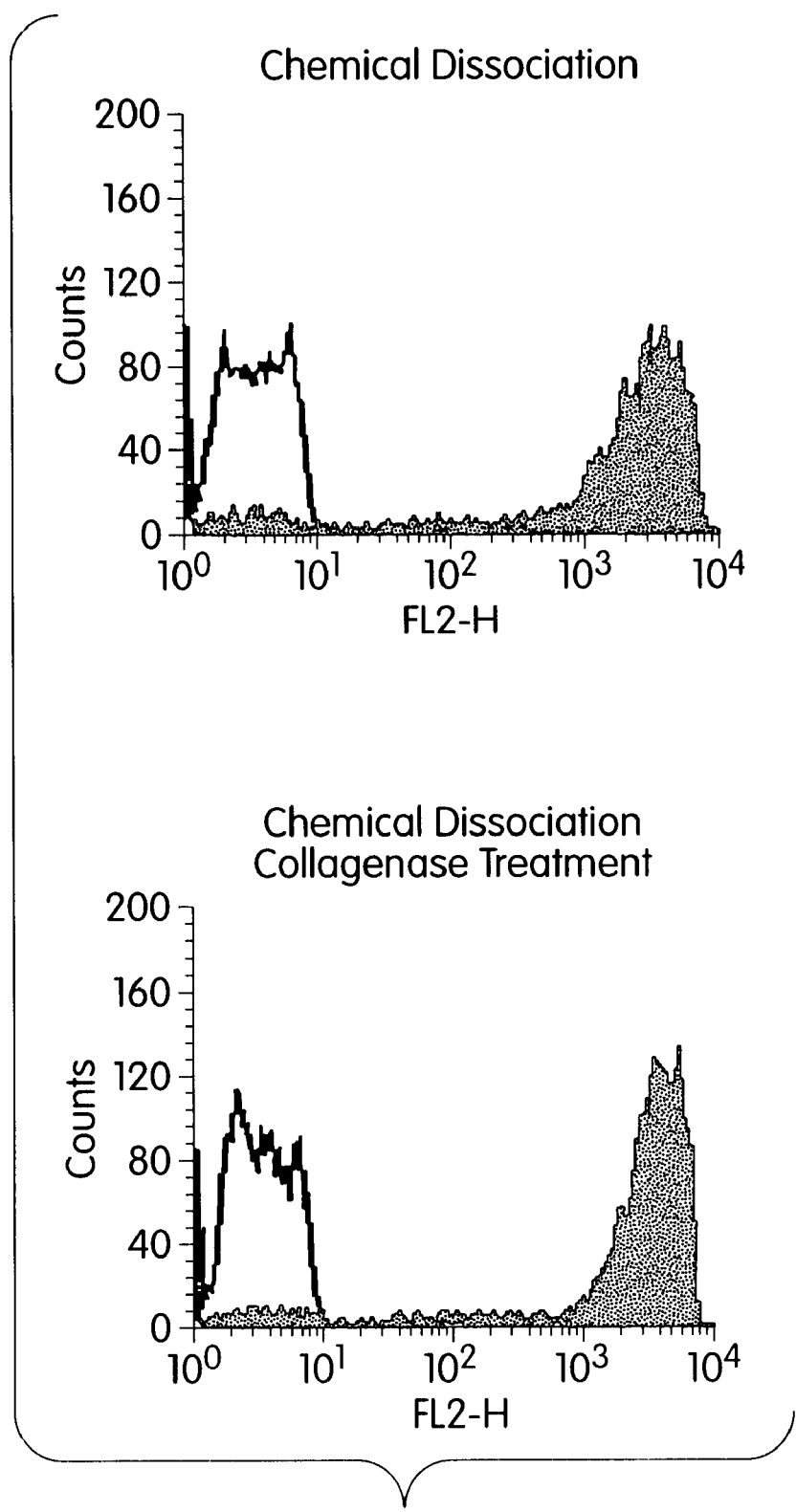

CTLA4⁻ cells (FIG. 3, R4). Staining of samples treated with collagenase prior to FACS resulted in the complete transformation of R2 double positive cells to double negative cells (FIG. 3, R3) while the single positive CD44⁺, CTLA4⁻ population remained unaffected (FIG. 3). The preferential elimination of the double positive R2 population over that of the single positive R4 cell population is consistent with the model of extracellular CD44 and CTLA4 bound to ECM being preferentially removed by collagenase treatment. The presence of collagenase resistant CD44⁺, CTLA4⁻ cell population suggests that those cells display CD44 surface proteins and furthermore indicates the lack of nonspecific protease activity in this assay. In control experiments using CHO-CTLA4 gpi cells, collagenase treatment had no effect on CTLA4 surface staining (FIG. 3), consistent with the absence of the requisite collagenase hydrolysis FALGPA motif in the adult murine CTLA4 extracelluar protein sequence.

Example 6

Animal Model of Soluble CTLA4 Function

Figure 4:
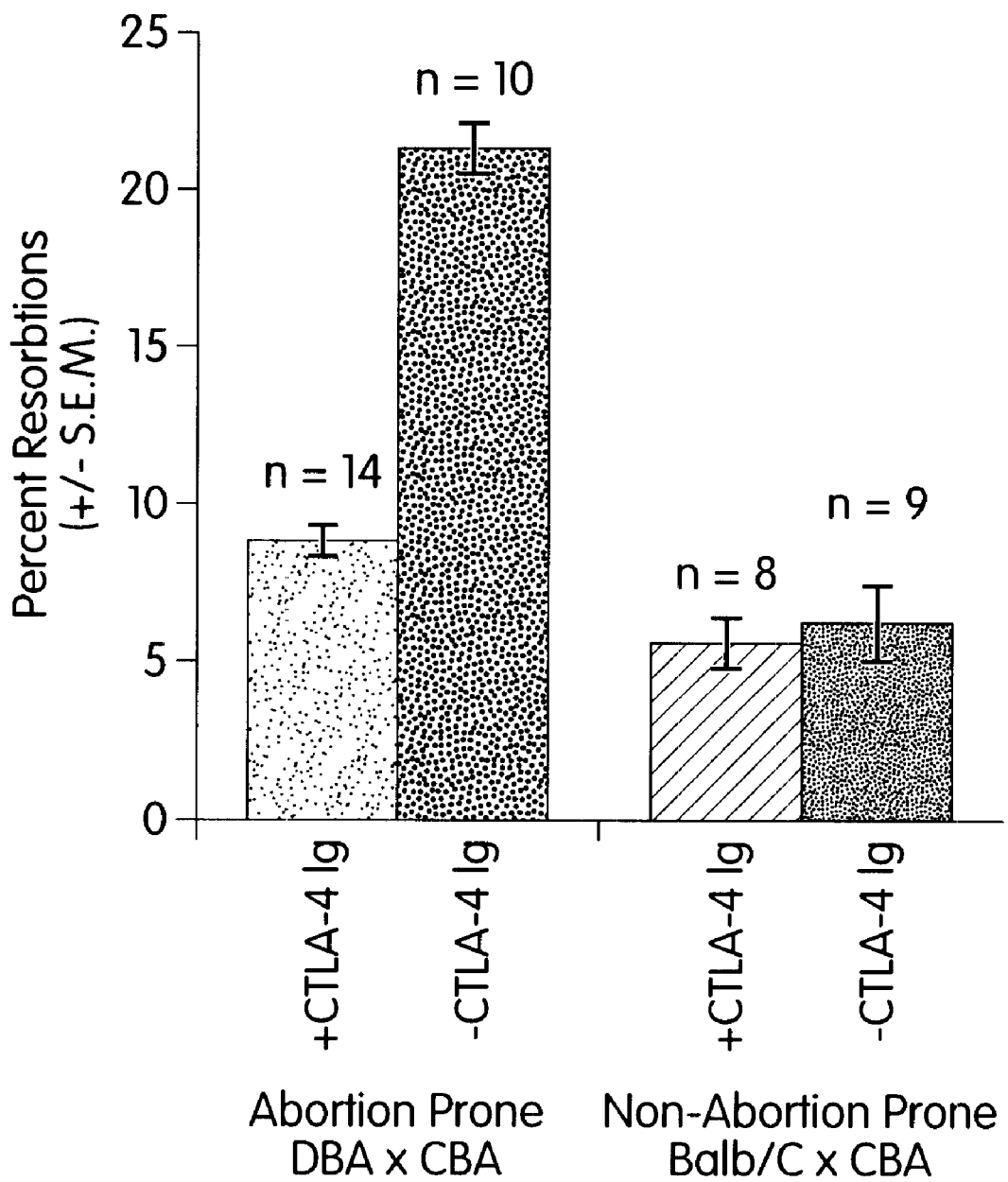
FIG. 4 shows effects of mCTLA4 Ig administration on the spontaneous abortion mouse model. CTLA4 treated pregnant mice from abortion prone matings (DBA×CBA) and non-abortion prone matings (BALC/c×CBA) were sacrificed on day 12 of gestation and percent resorbed embryos were tabulated.

The DBA×CBA abortion prone mouse model is the standard model for the study of immune mediated spontaneous abortion (Toder et al., 1989, *J Reprod Fertil Suppl* 37, 79–84). In pregnant CBA female mice, the resorption rate of DBA:CBA hybrid embryos occur in 21–30% of the embryos compared with 8% resorption in control Balb C: CBA embryos. In this model system, a maternal immunological rejection response towards the embryo initiates at day 6 of gestation, 2 days following implantation (Duclos et al., 1995, *Am J Reprod Immunol* 33, 354–66). To assess the potential of a soluble CTLA4 to suppress maternal rejection of the embryo, two 200 μg doses of CTLA4 Ig were administered to pregnant mice with either high or low rates of spontaneous abortion. Doses were administered at days 4 and 6 of gestation, corresponding to the time of implantation (day 4) and day when immunological reactions to the embryo is first detected (day 6). Quantitation of resorbed embryos was performed on day 12 of gestation. In highly aborting CBA x DBA mated mice (n=14), embryonic resorption rates averaged of 8%, identical with that of control BALB/c×DBA mated mice (n=8), demonstrating the efficacy of CTLA4 Ig treatment to ameliorate spontaneous abortion in this animal model FIG. 4.

Materials and Methods Used in Examples 7–11
The Following Materials and Methods Were Used in Examples 7–11.

Animal Mating and Treatment Groups. Virgin CBA/J female and DBA/2 male ice (6–8 weeks old) were obtained from Jackson Laboratory (Bar Harbor, Me.). Animals were housed in pathogen free microisolater cages at 21° C. and were fed food and water ad libitum. Animals were bred one week following arrival by combining three CBA/J female mice to one DBA/2 male. Daily examination for copulatory plug was performed to assess pregnancy. Presence of copulatory plug was designated at gestation day 0 (gd). On gestational day 4 and 6, 200 μg mCTLA4IgG2am or isotype control immunoglobulin, was injected ip. On gestation day 12, animals were euthanized with $CO_2$, and gross uterine examination and caliper measurements of the feto-placental units along the longitudinal axis of the uterine horn were performed to assess fetal/placental development. Total numbers of feto-placental units along with resorptions were identified by appearance of small 4–5 mm feto-placental unit, characterized by necrotic and hemorrhagic appearance. Resorption rates were presented as percent of resorbing feto-placental units compared to the total number of feto-placental units. Intrauterine growth retardation (IUGR) was designated by a 15% decrease in mean feto-placental size compared to the overall maximal mean of all mice. Nonresorbing and resorbing placental tissue was removed and snap frozen in liquid nitrogen for total RNA extraction.

RNA Extraction and Quantitative PCR. Total RNA was extracted from liquid nitrogen snap-frozen tissues using the Tri-Reagent® according to manufacturer specification (Molecular Research Center, Cincinnati, Ohio). Total RNA was treated with RQI Dnase I (Promega, Madison, Wis.) Rnase inhibitor (Five Prime Three Prime Inc., Boulder, Colo.) for one hour at 37° C. RNA clean was performed using Qiagen Rneasy Minicolumns (Qiagen Inc., Valencia, Calif.) according to manufacturer specification. rtth DNA Polymerase was used to reverse transcribe and amplify 125 ng of total RNA using the Perkin Elmer Taqman EZ RT-PCR kit (Perkin Elmer Applied Biosystems, Foster City, Calif.) with gene-specific forward and reverse primers and flourescently labeled probe at the 5' end with 6-carboxy-flourescein (6-FAM). Primer and probe sequences were generated using Primer Express software (Perkin Elmer) and publically available gene sequences, e.g., AH005387 (VCAM-1); M31585 (ICAM); L06039 (PECAM); M87861 (P-selectin); M87862 (E-selectin); AH001969 (IL-2); M84340 (IL-10); M86672 or M86671 (IL-12); U03421 (IL-11); U68416 (TNFα); M15131 (UL-1β); U65016 or M13177 (TGF); AF065896 (B7.1/CD80); AF065900 (B7.2/CD86); M36850 (CD4); U34882 (CD8); AF252285 (RANTES); M20572 (IL-6); AF199027 (mGL50); AJ250559 (ICOS); U43428 (INOS); and K00083 (IFN-γ).

Duplicate samples were reverse transcribed for 30 minutes at 60° C., followed by 40 cycles of amplification for 15 seconds at 95° C. and one minute at 60° C. using the ABI Prism 7700 sequence detection system as described by the manufacturer (Perkin Elmer). Gene-specific amplification was detected as a fluorescent signal during the amplification cycle. Gene-specific message quantification was evaluated by fluorescence intensity levels of unknown samples compared to fluorescence intensity of known mRNA levels. Amplification of a house keeping gene, murine GAPDH, was performed on all samples to account for RNA level variations. All genes were normalized to GAPDH mRNA levels and levels of gene-specific messages were depicted as normalized Taqman units as determined by standard curve.

In vivo Radiolabeled Adhesion Molecule Expression. Pregnant CBA/J mice were anesthetized at gestation day 12 with an intraperitoneal injection mixture of 100 pl each of ketamine (50 mg/ml) and xylazine (2.75 mg/ml). The left jugular vein and right carotid artery were cannulated with polyethylene tubing (PE-10). Radiolabeled MAb ($^{131}$I-nonbinding and $^{125}$I-VCAM-1) preparation was injected into the mouse via the jugular vein catheter, followed by an additional 0.2 ml of normal saline to aspirate all of the MAb in the syringe and tubing. Syringe was saved in a separate tube for radioactive counts. Antibody was allowed to circulate in vivo for 5 minutes at which time two 0.2 ml samples of blood were collected via the carotid artery catheter. Ten units of heparin (10 ml from a 1000 U/ml) were added to the blood sample and centrifuged at 3000 g for 10 minutes and 50 μl of plasma was collected and placed in a in new tube for radioactive counts. Next, 40 units of heparin (40 μl of 1000 U/ml) were injected into the jugular vein catheter immediately following the second blood draw. Whole body perfusion was performed by simultaneous infusion of bicarbonate buffered saline (BBS) via the jugular vein catheter and blood removal from the carotid artery catheter; perfusion was performed until the effluent was clear (approximately 15–20 mls). Next, mice were backflushed with an infusion of 10–15 mls of BBS via the carotid artery catheter by severing the inferior vena cava at the thoracic level. Finally, designated tissues were dissected, dipped in distilled water, blotted dry, weighed, and placed in scintillation tubes for gamma counter for irradiation counts on dual isotope spectrum. Calculation of specific antibody incorporation was determined by the following equation:

$$\frac{\% \text{ injected activity}}{\text{gram tissue}} = \frac{(^{125}\text{I cpm/gram tissue})}{(^{125}\text{I cpm/injected})} - \frac{(^{131}\text{I cpm/gram tissue})}{(^{131}\text{I cpm/injected})} \times \frac{(^{125}\text{I plasma})}{(^{131}\text{I plasma})} \times 100$$

Example 7

Gross Anatomy of CBA X DBA Mated Female Uterine Horn

Examination of the gross anatomy of a CBA X DBA mated female uterine horn revealed focal areas of necrosis, a hemorrhagic appearance surrounding a diseased fetoplacental unit, and intrauterine growth retardation.

Example 8

Staining of Placental Sections

Hemotoxylin and eosin staining of normal and resorbed placentas revealed that in resorbed diseased placenta, there was cellular infiltration of the maternal decidua basalis, and there was also loss of normal placental structure in the fetal aspects of the placenta.

Example 9

Reduction in Fetal Resorption and Intrauterine Growth Disturbances Through Treatment With mCTLAIgG2am

TABLE 1

Treatment with mCTLA4IgG2am decreases fetal resorption and intrauterine growth disturbances (IUGR) in the CBA X DBA pathologic pregnancy.

| Treatment | % Resorption (SD) | % IUGR (SD) |
|---|---|---|
| No treatment (n = 10) | 21.4 (7.3) | 65.1 (19.4) |
| mCTLA4IgG2am (n = 11) | 9.2 (11.5) | 19.3 (22.8) |
| IgG2am (isotype control) (Fc-formulated) (n = 6) | 27.3 (2.0) | 46.6 (19.8) |

TABLE 2

Treatment with mCTLA4IgG2am does not affect resorption but does decrease intrauterine growth disturbances in the CBA X Balb/c normal pregnancy.

| Treatment | % Resorption (SD) | % IUGR (SD) |
|---|---|---|
| No treatment (n = 9) | 6.2 (9.7) | 37.4 (21.8) |

TABLE 2-continued

Treatment with mCTLA4IgG2am does not affect resorption but does decrease intrauterine growth disturbances in the CBA X Balb/c normal pregnancy.

| Treatment | % Resorption (SD) | % IUGR (SD) |
|---|---|---|
| mCTLA4IgG2am (n = 7) | 2.86 (7.6) | 11.7 (15.1) |
| IgG2am(isotype control) (Fc-formulated) (n = 5) | 0 (0) | 17.86 (12.48) |

Example 10

In vivo Accumulation of $^{125}$I Labeled VCAM-1 MAb

Figure 5A:
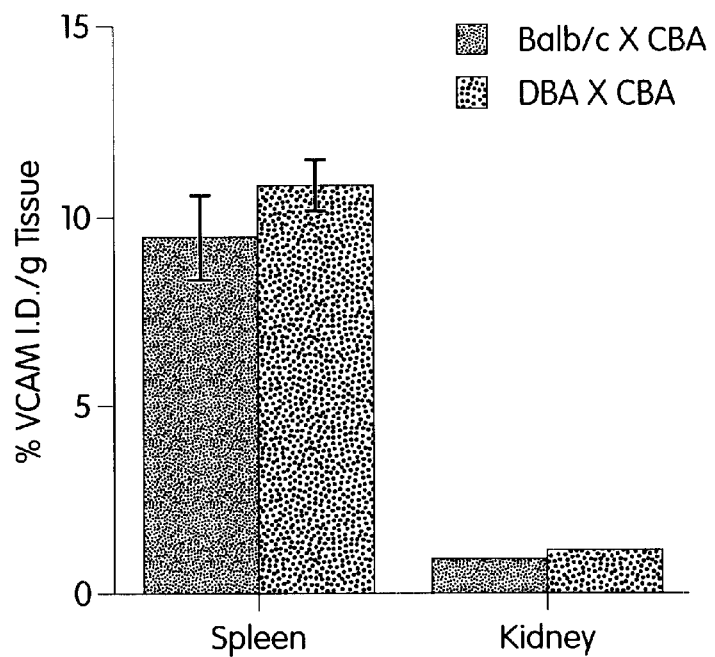
FIG. 5 shows the quantiation of $^{125}$I labeled VCAM-1 monoclonal antibody (MAb) in the two mating crosses. Panel A shows binding to spleen and kidney in the two mating crosses. Panel B shows binding to normal placenta (NPlacenta), resorbing placenta (RPlacenta), and uterus tissue in the two mating crosses.
Figure 5B:
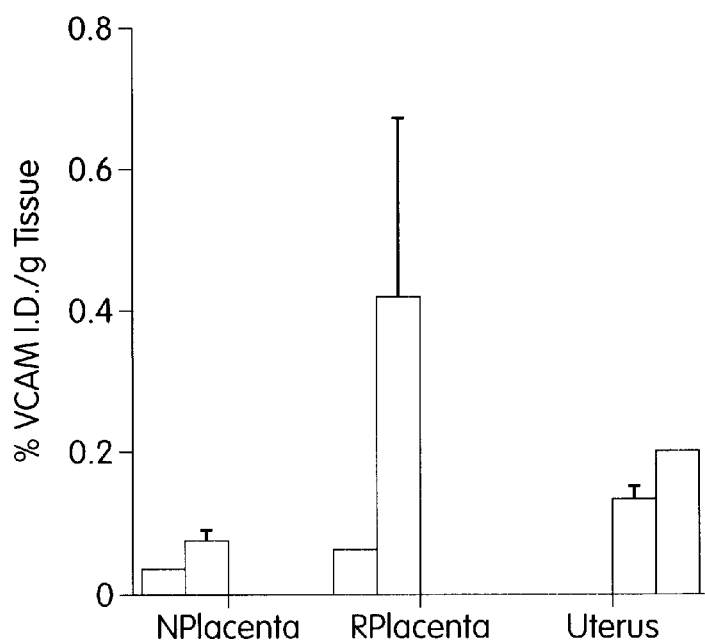

In vivo accumulation of $^{125}$I labeled VCAM-1 monoclonal antibody (MAb) in the two mating crosses did show organ-specific differences between spleen and kidney (FIG. 5A), but did not show significant differences in VCAM-1 binding between the two mating groups. However, VCAM-1 binding was found to be elevated in the placentas of the DBA X CBA cross, when compared to the BALB/c×CBA mating combination (FIG. 5A). Particularly, the highest accumulation was seen in the resorbing placentas of the pathologic mating group.

Example 11

Figure 6A:
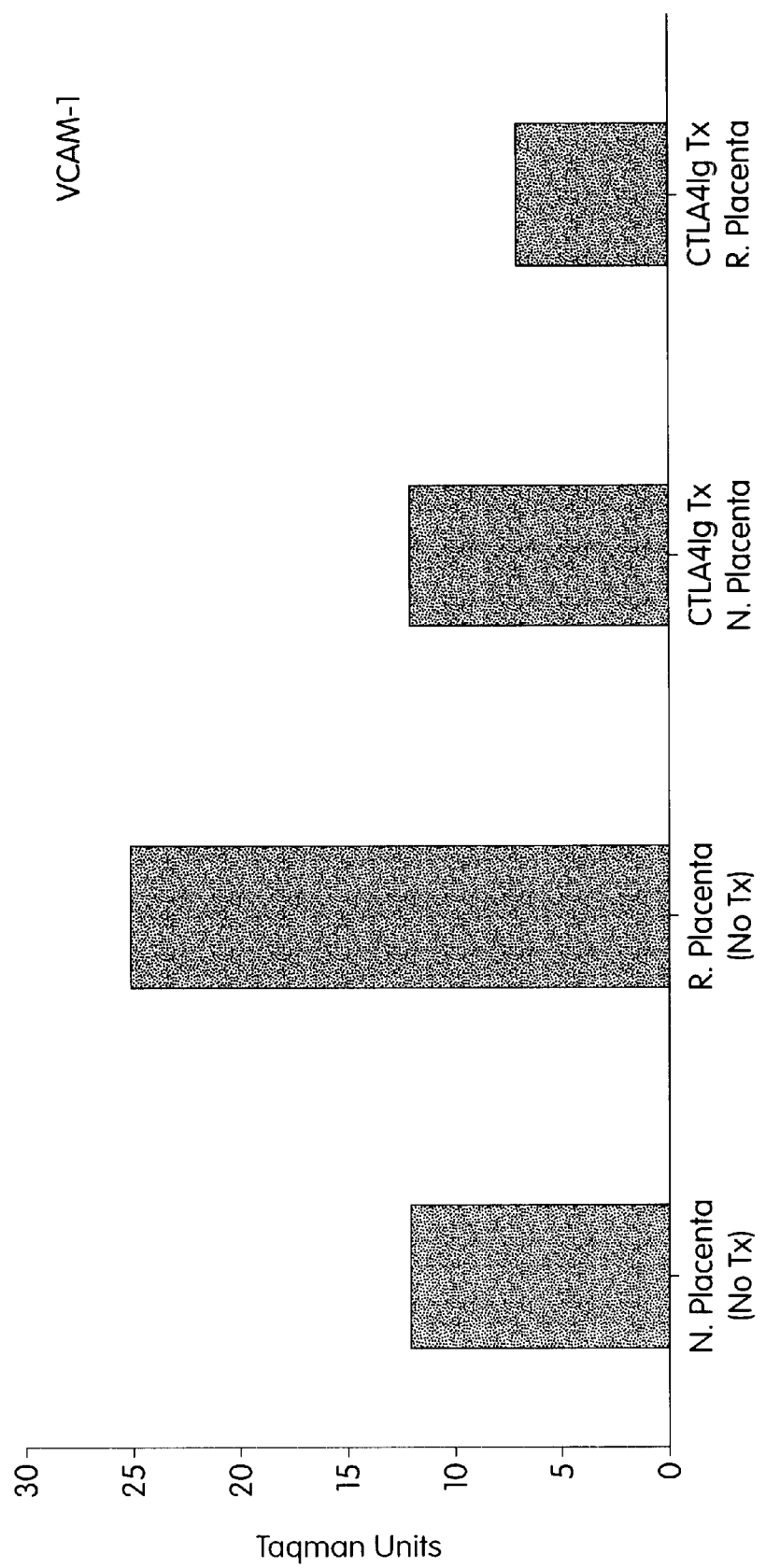
FIG. 6 shows the quantitation mRNA expression of adhesion molecules, cell surface antigens, and cytokines in normal (N. Placenta) and resorbing (R. Placenta) placental tissue either untreated (No Tx) or treated (Tx) with CTLA4-Ig. All genes were normalized to murine GAPDH. The genes analyzed were: (A) VCAM-1; (B) ICAM; (C) PECAM; (D) P-selectin; (E) E-selectin; (F) IL-2; (G) IL-10; (H) IL-12; (I) IL-11; (J) TNF-α; (K) IL-1β; (L) TGF; (M) B7.1 (CD80); (N) B7.2 (CD86); (O) CD4; (P) CD8; (Q) RANTES; (R) IL-6; (S) mGL50; (T) mICOS; (U) INOS; and (V) TFN-γ.
Figure 6B:
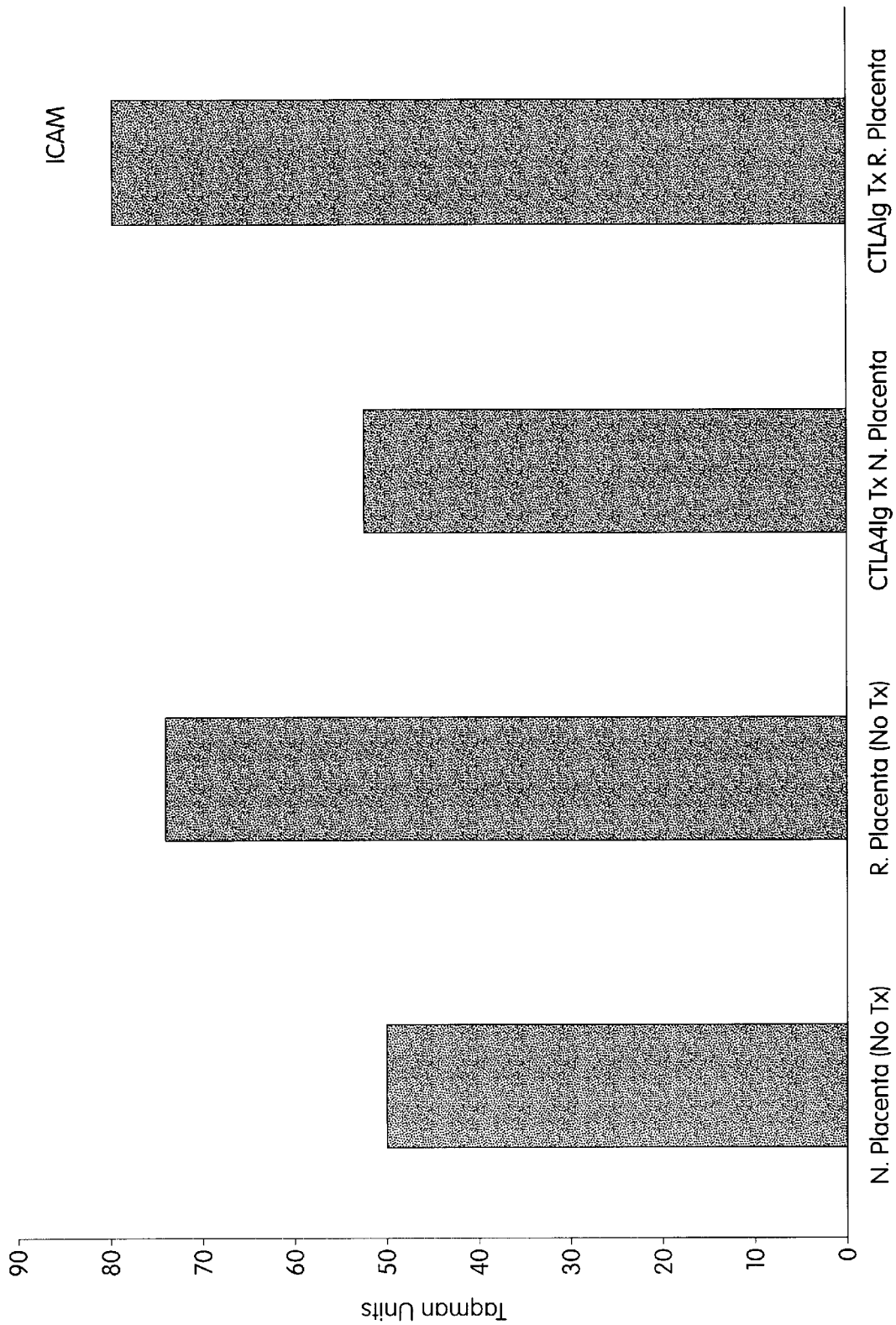
Figure 6C:
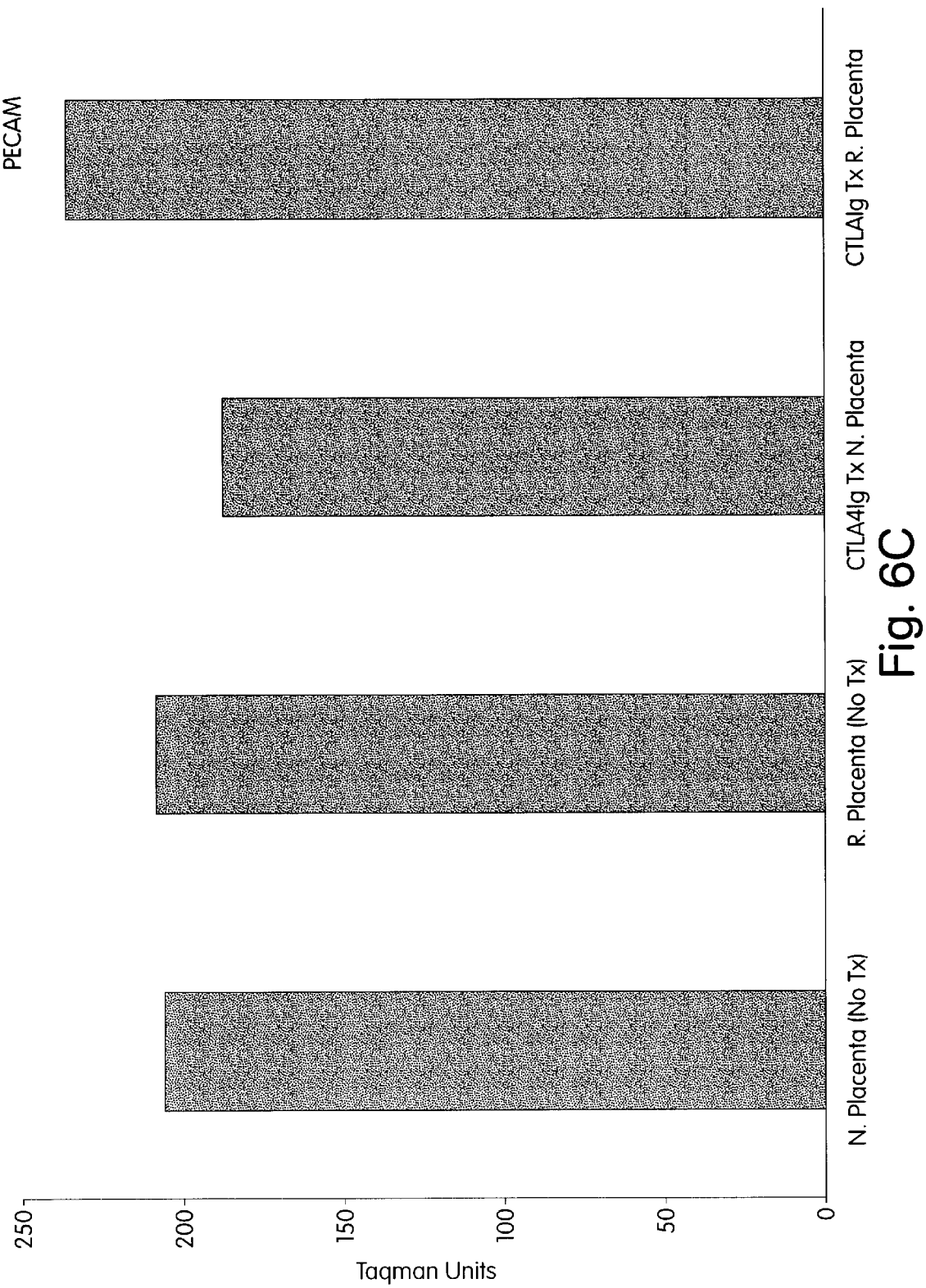
Figure 6D:
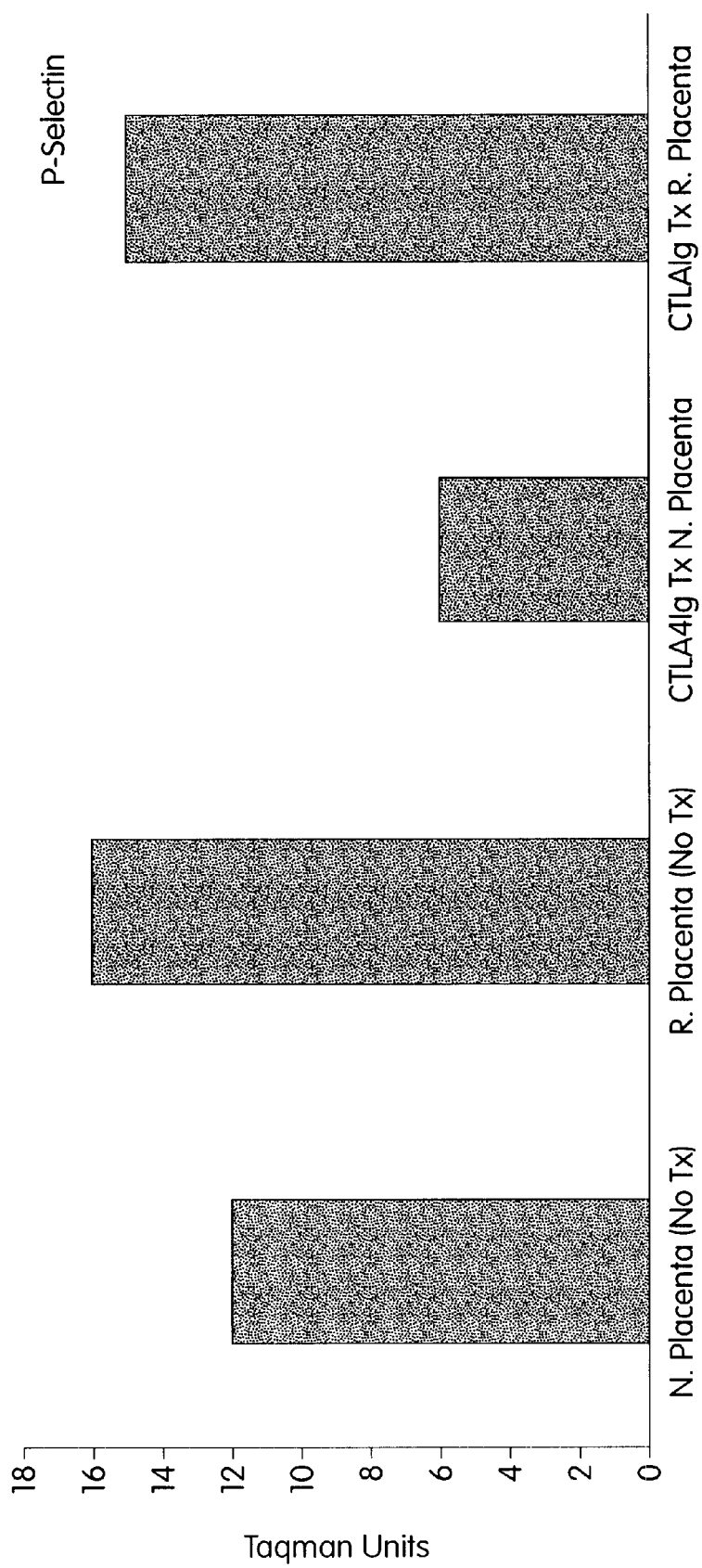
Figure 6E:
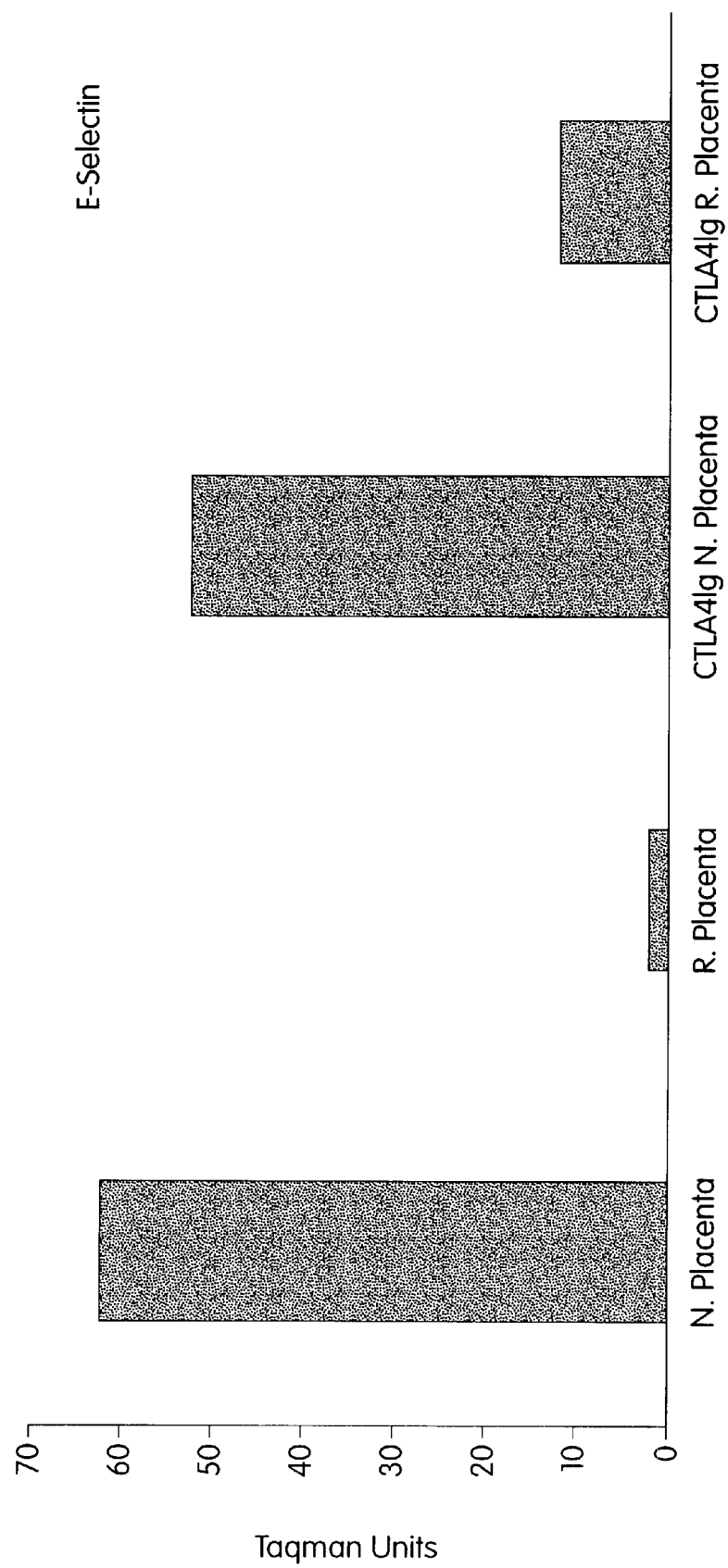
Figure 6F:
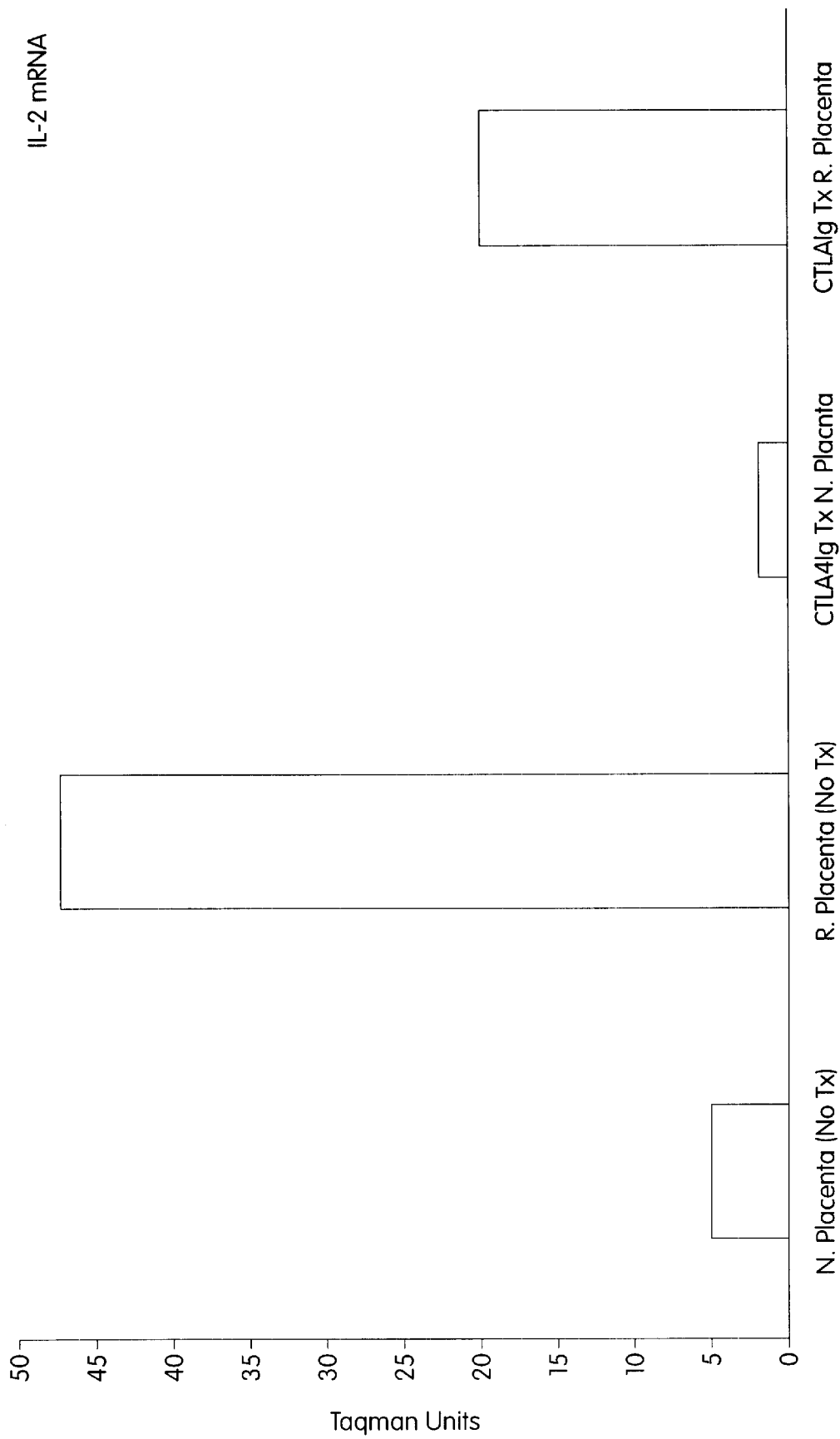
Figure 6G:
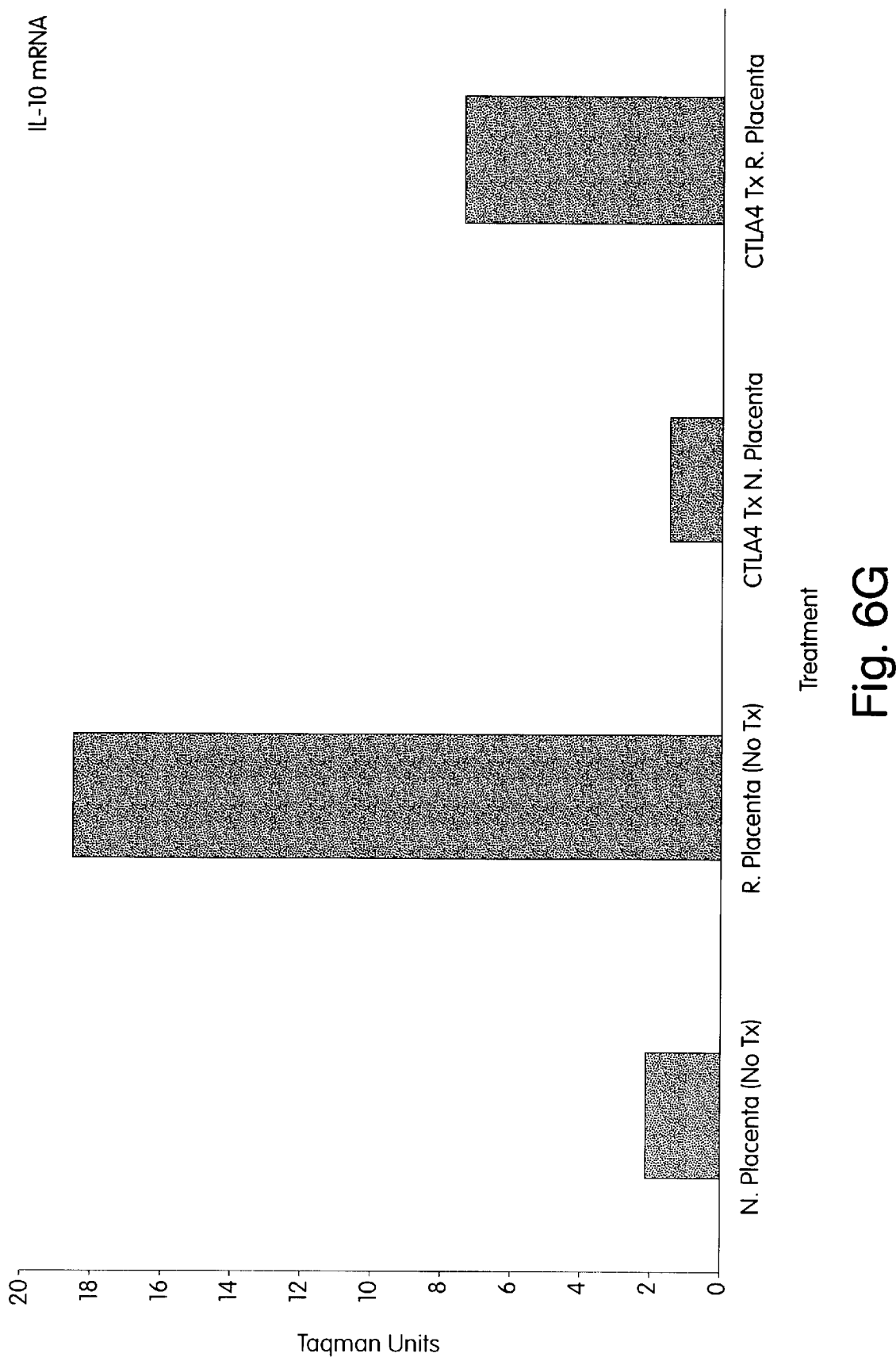
Figure 6H:
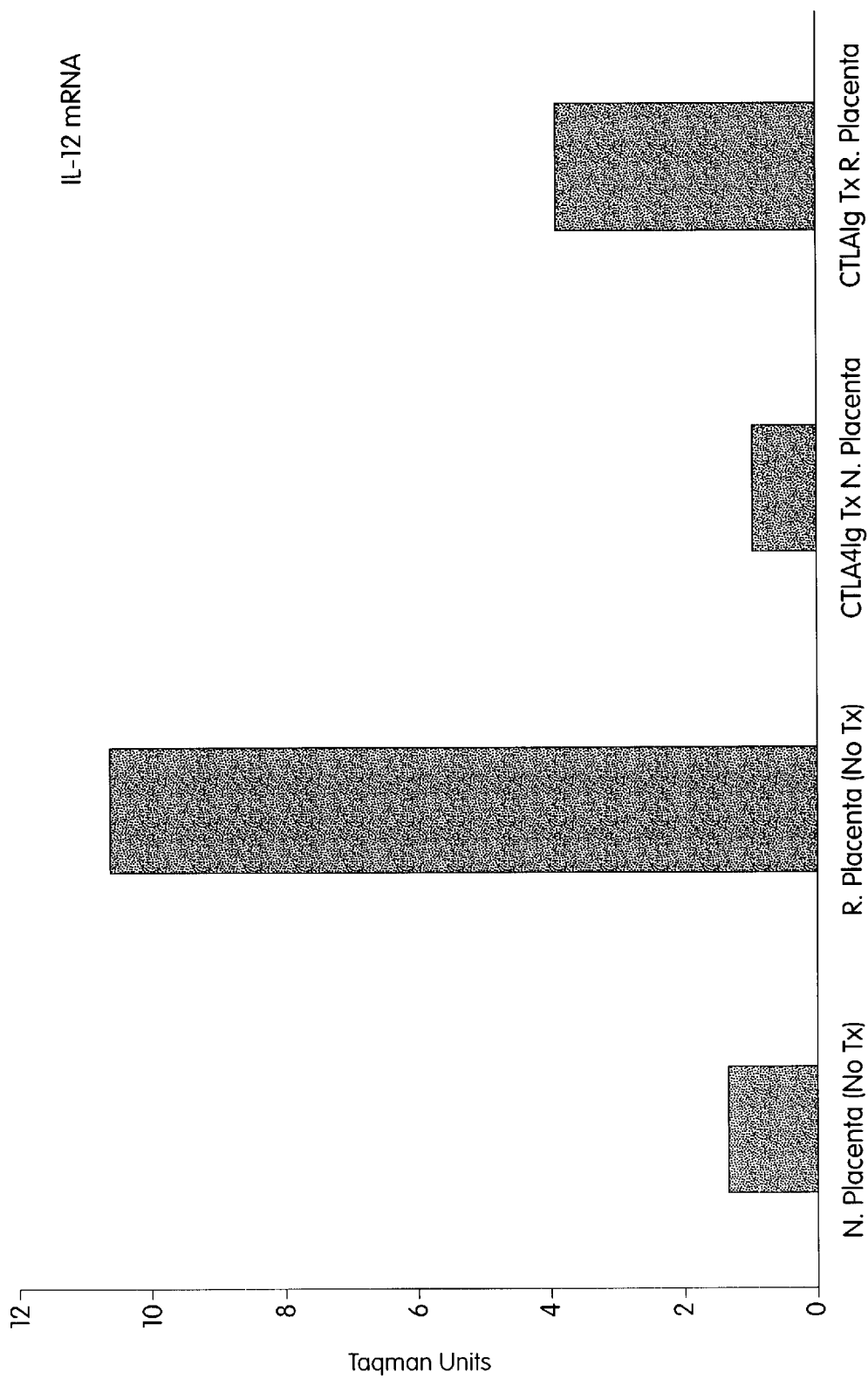
Figure 6I:
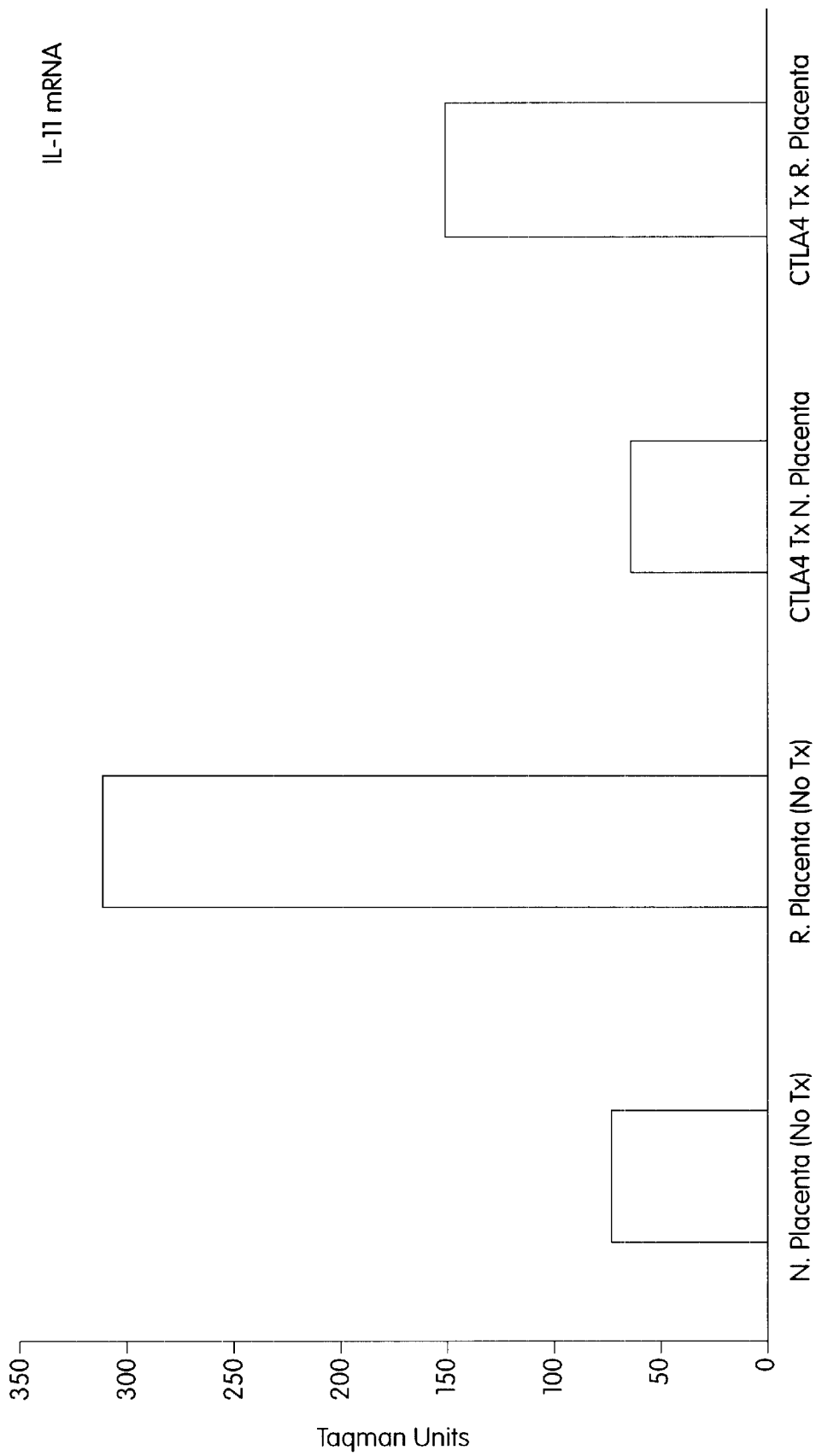
Figure 6J:
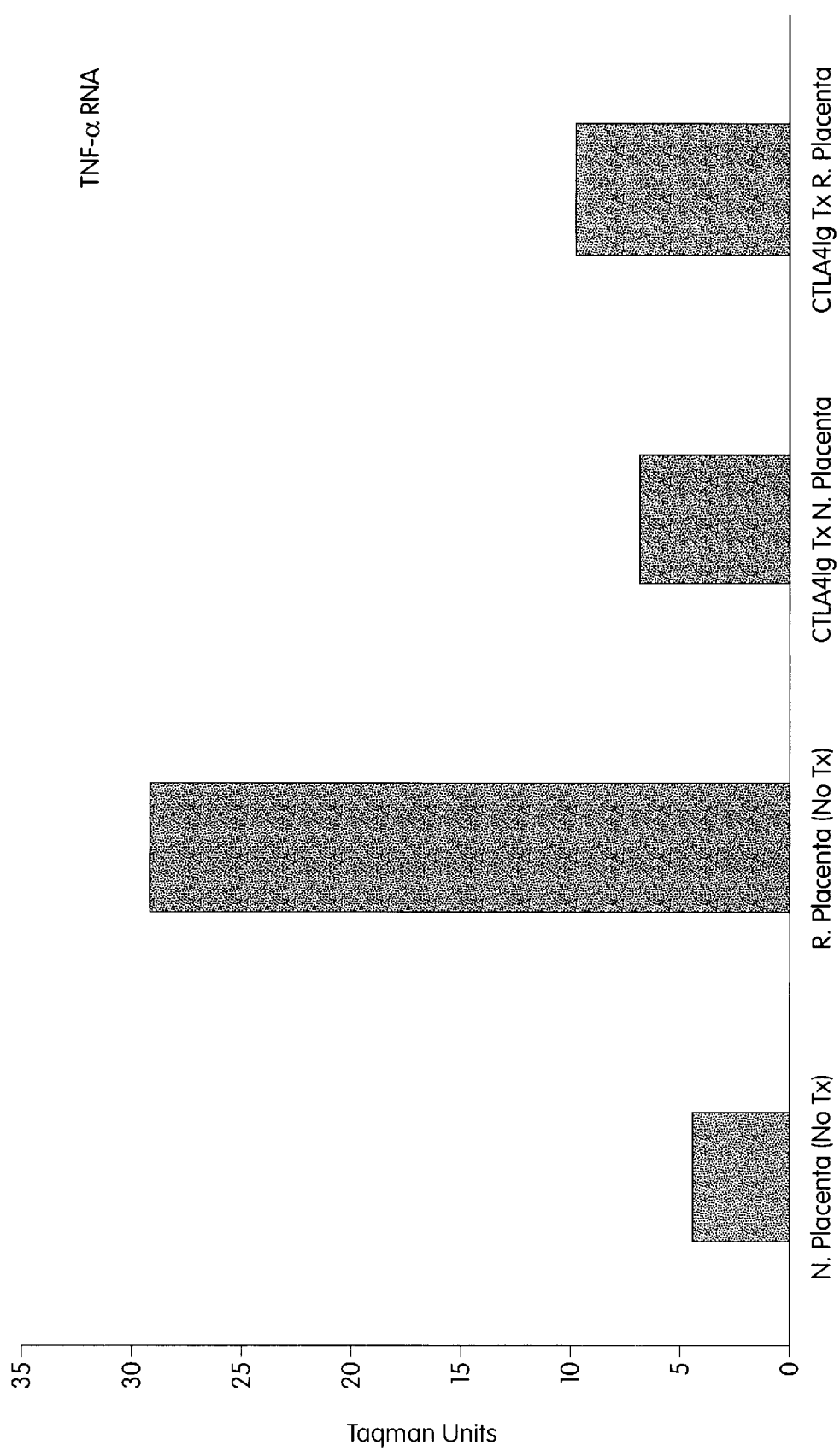
Figure 6K:
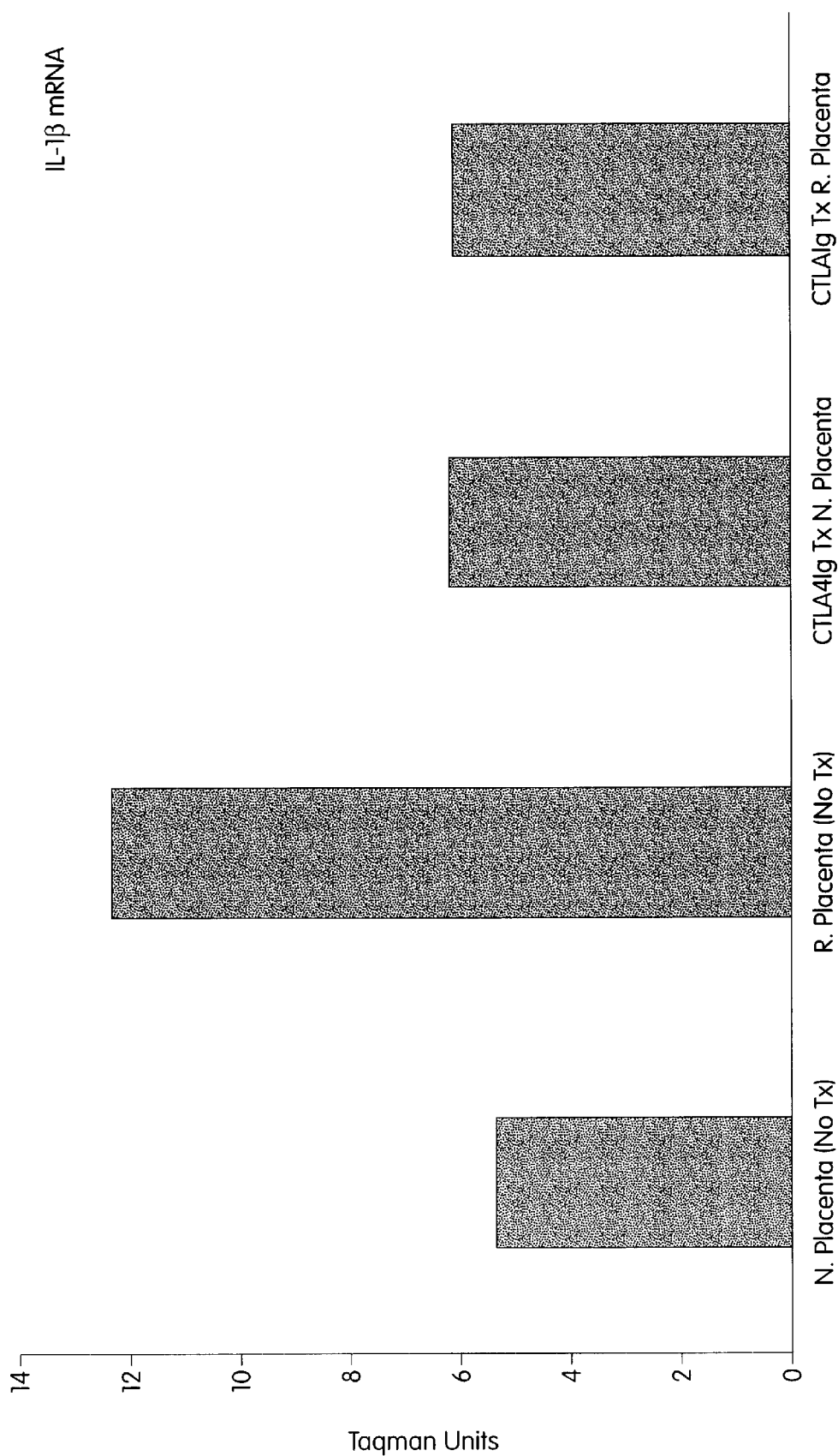
Figure 6L:
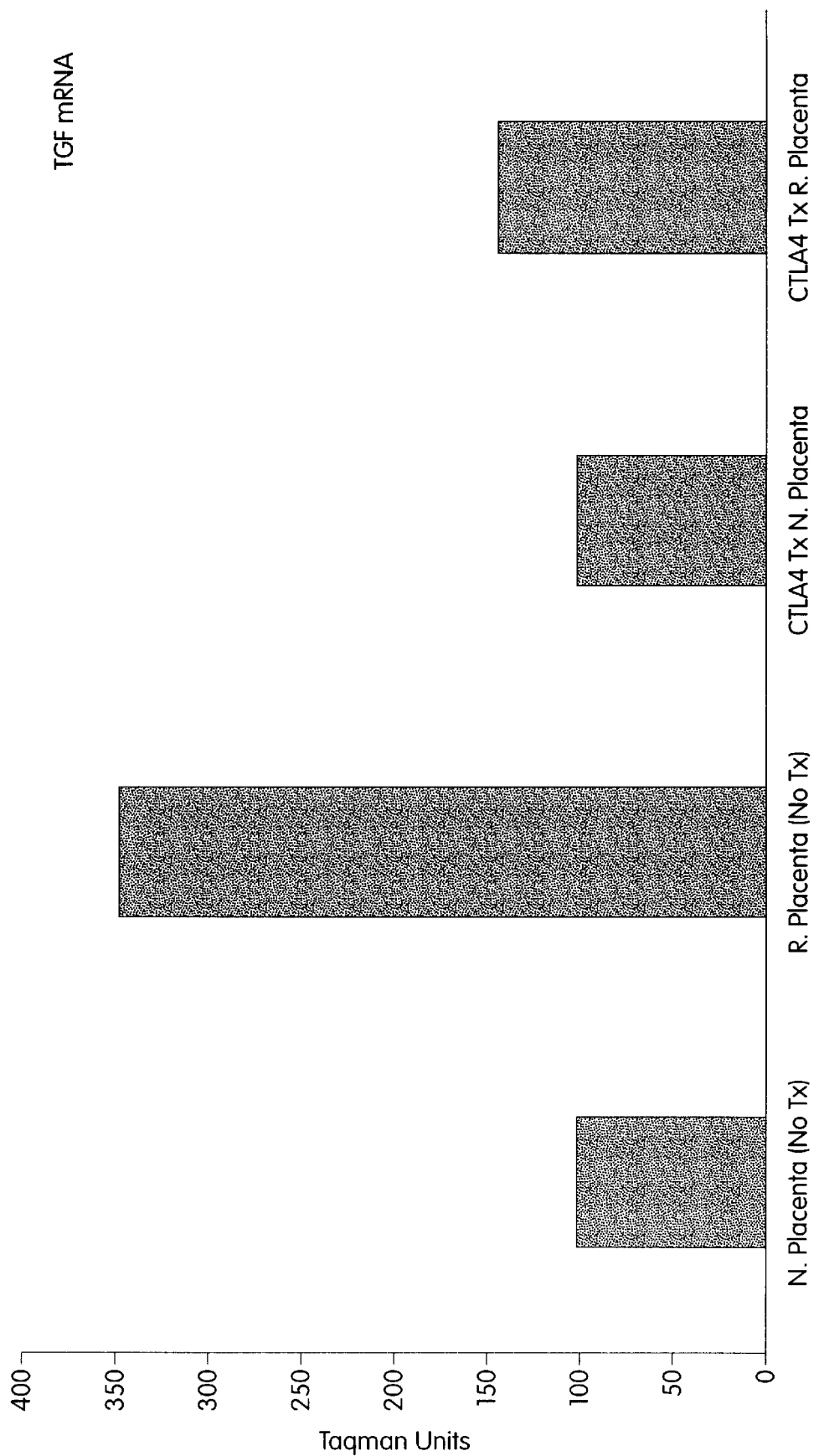
Figure 6M:
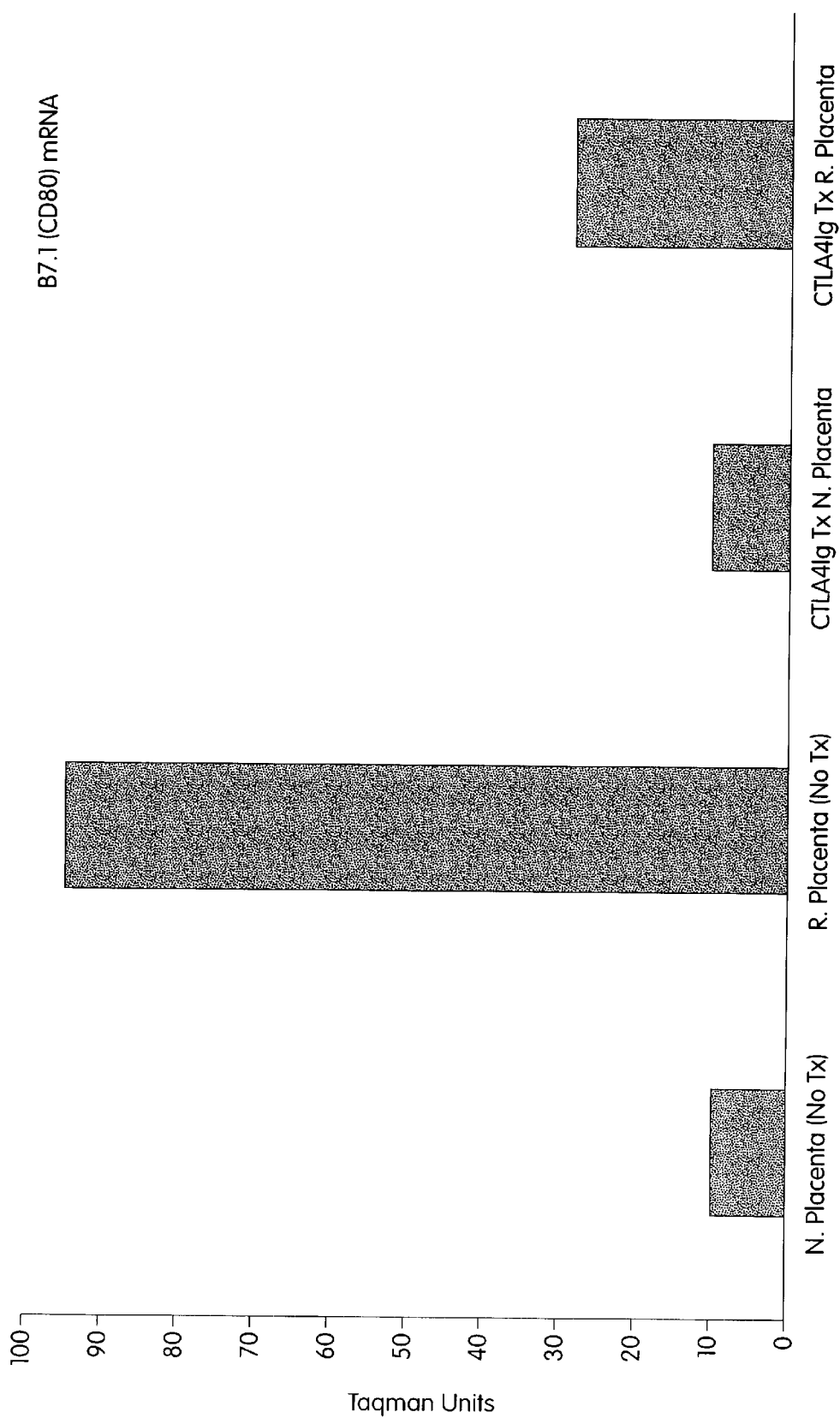
Figure 6N:
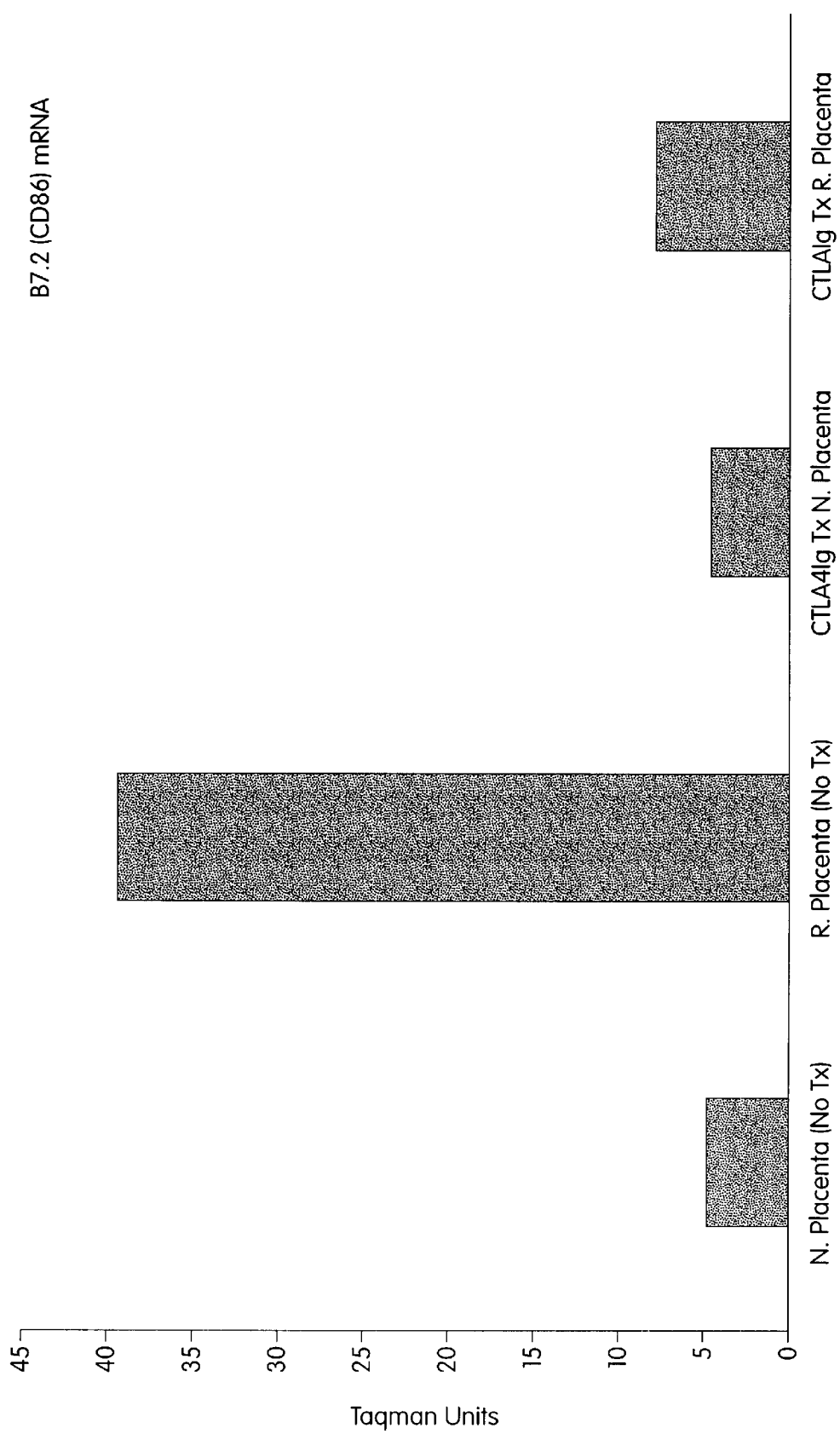
Figure 60:
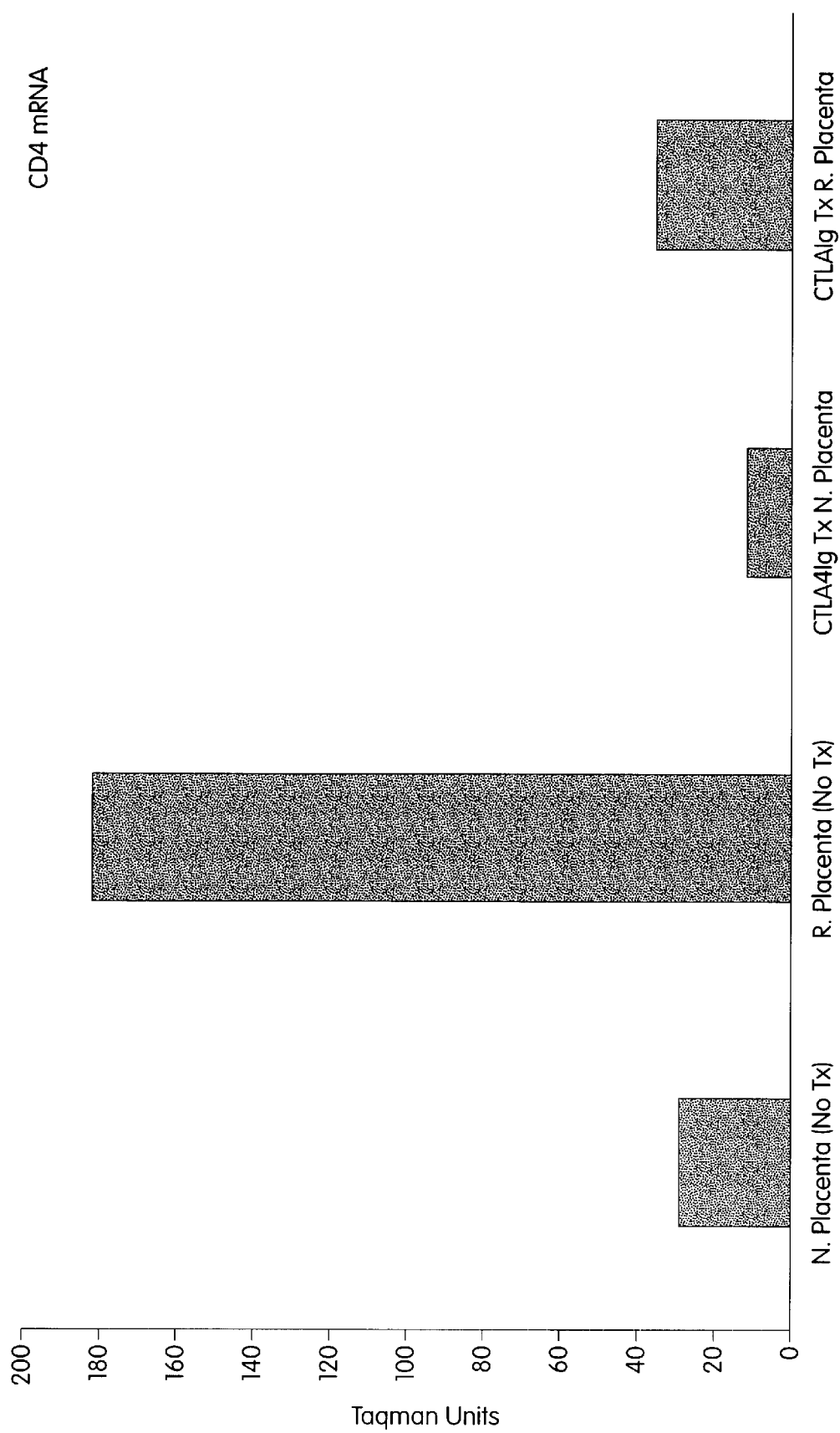
Figure 6P:
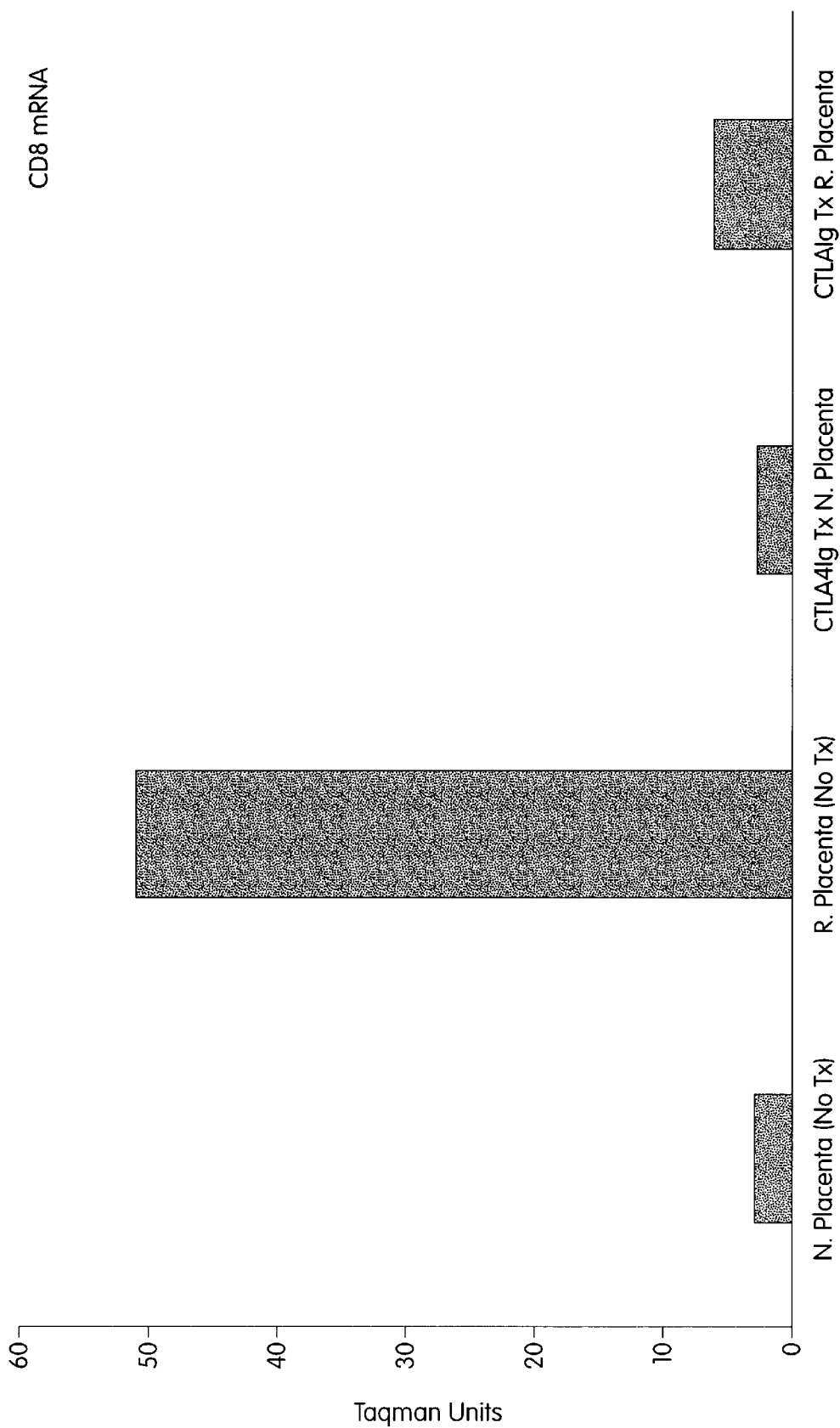
Figure 6Q:
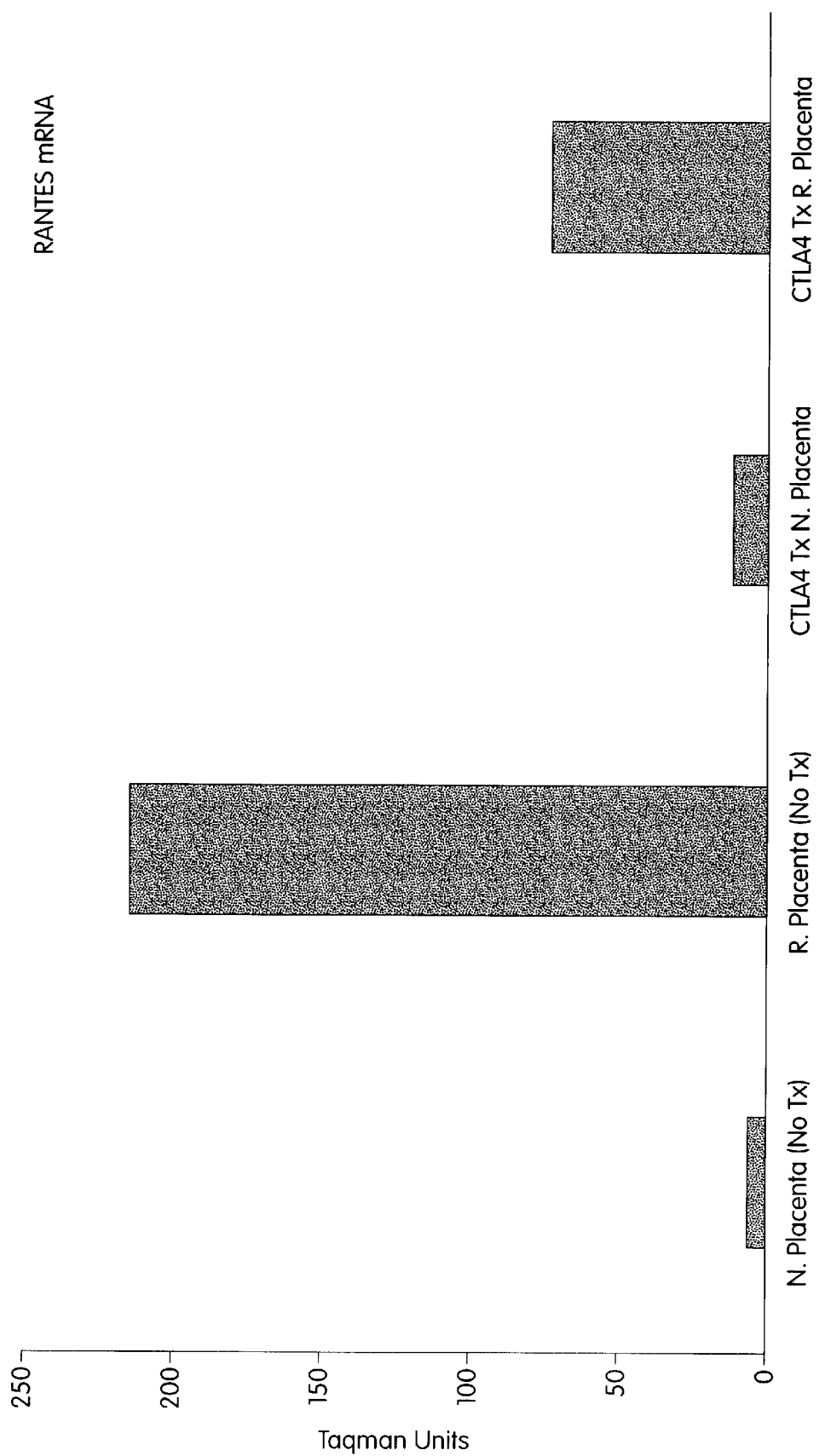
Figure 6R:
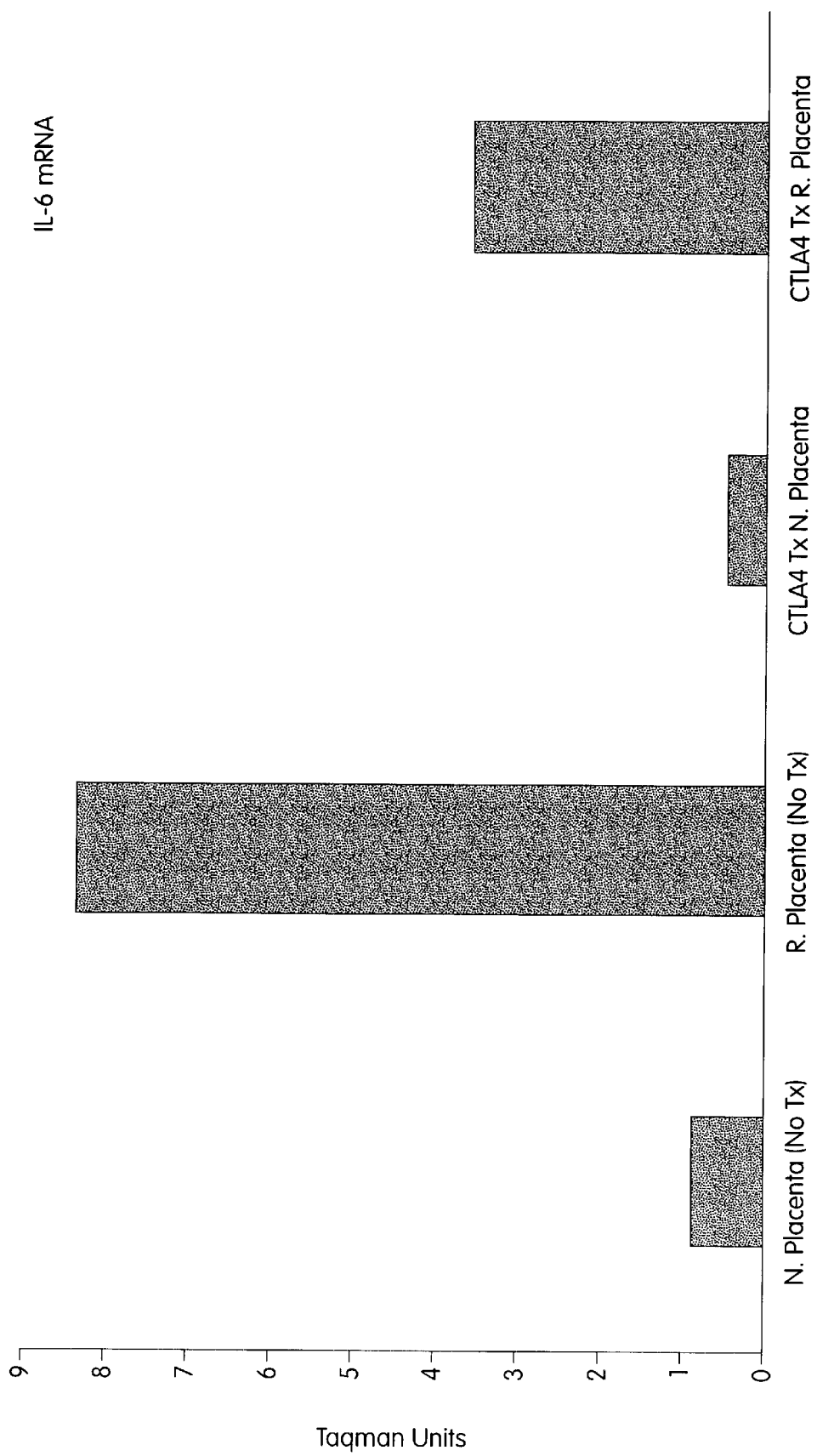
Figure 6S:
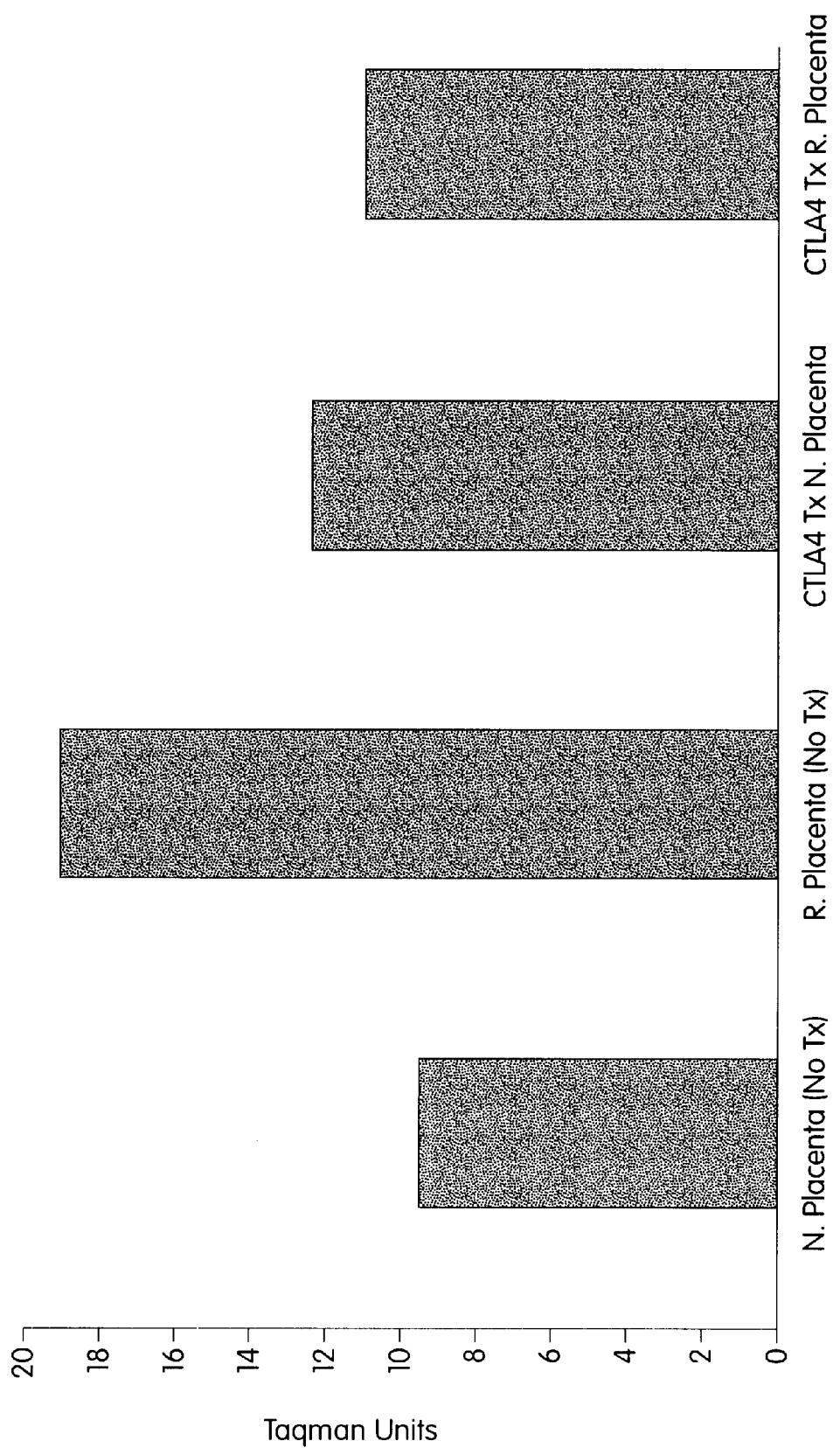

Gene Expression Analysis of Adhesion Molecules, Cell-surface Antigens, and Cytokines Pooled RNA from normal and resorbing placentas in untreated and CLTA4-Ig treated mice was subjected to RT-PCR quantification. All genes were normalized to murine GAPDH. Message levels for VCAM-1 in resorbing placental tissues were found to be elevated, and treatment with CTLA4-Ig reduced VCAM-1 message (FIG. 6A). Message levels for ICAM (FIG. 6B) and PECAM (FIG. 6C) were not affected by treatment. P-selectin message was elevated in resorbing tissue and was not affected by CTLA4-Ig treatment (FIG. 6D). However, E-selectin message was found to be elevated in non-resorbing tissue and expressed at very low levels in resorbing tissue (FIG. 6E).

Figure 6T:
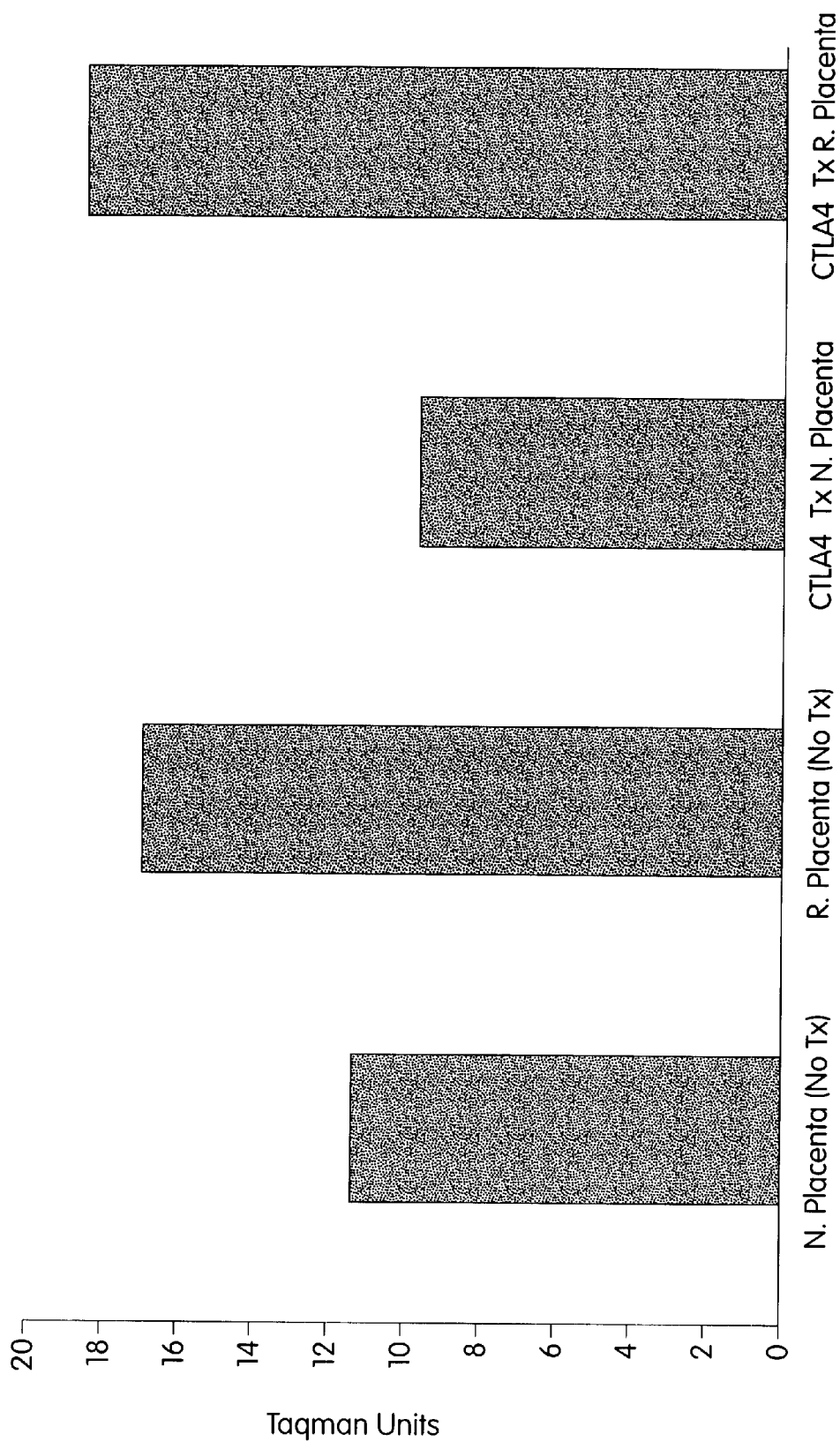
Figure 6U:
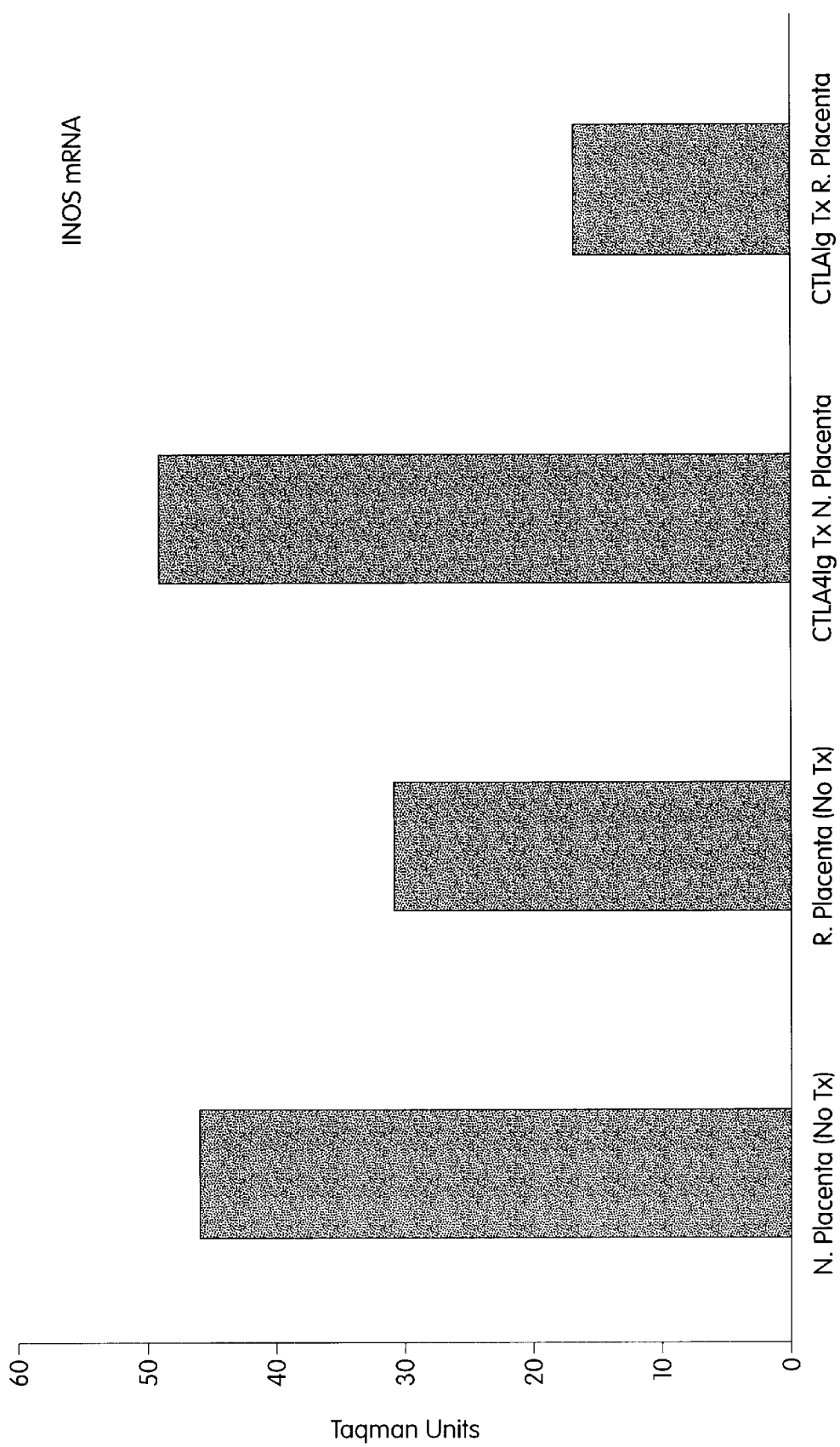
Figure 6V:
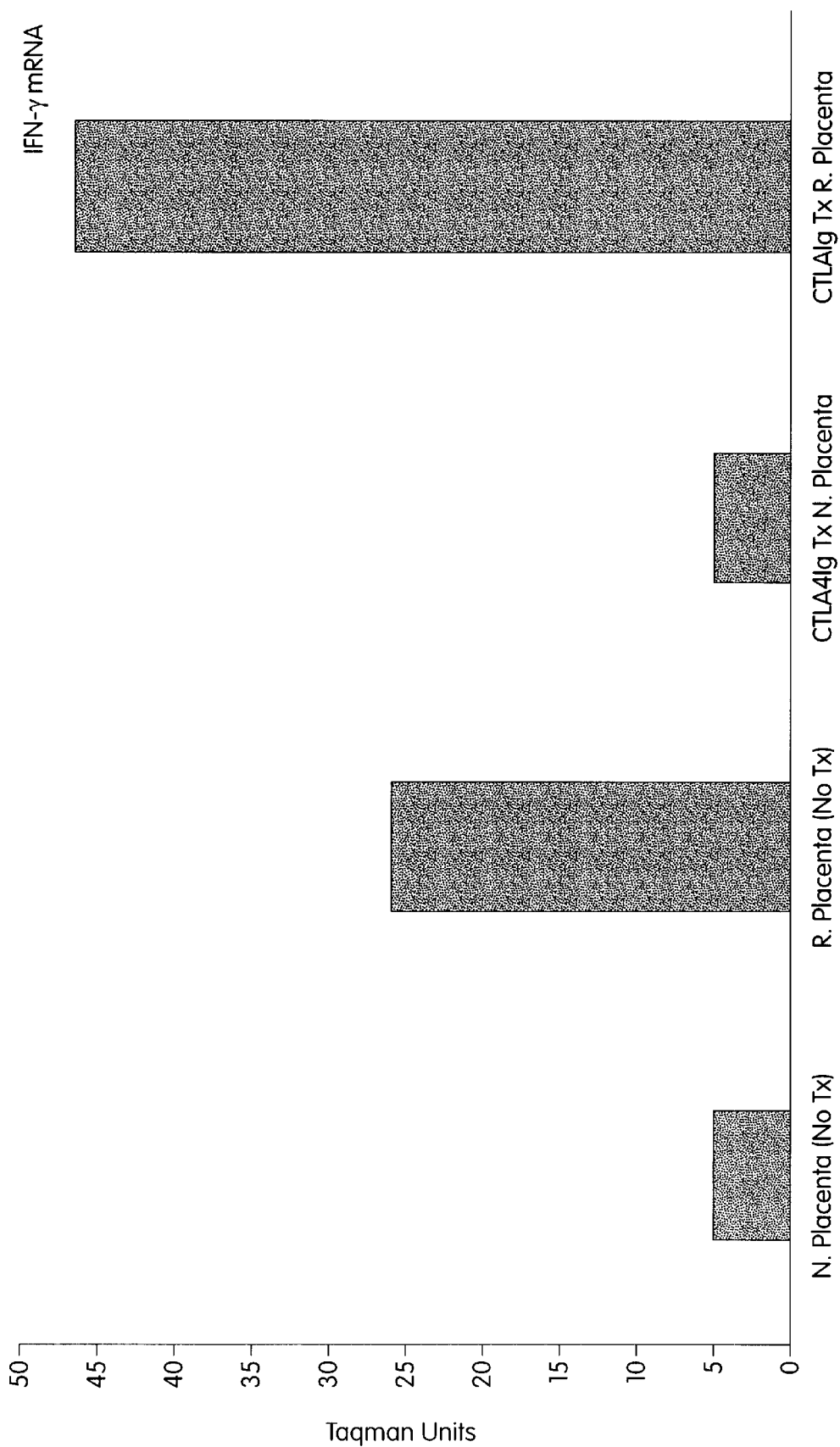

IL-2 message was elevated in resorbing tissue and was reduced by treatment (FIG. 6F), as were EL-10 message (FIG. 6G), IL-12 message (FIG. 6H), IL-11 message (FIG. 6I), TNFα message (FIG. 6J), IL-1β message (FIG. 6K), TGF message (FIG. 6L), B7.1 (CD80) message (FIG. 6M), B7.2 (CD86) message (FIG. 6N), CD4 message (FIG. 6O), CD8 message (FIG. 6P), RANTES message (FIG. 6Q), IL-6 message (FIG. 6R), and mGL50 message (FIG. 6S). mICOS message was elevated in resorbing tissue but was not affected by treatment (FIG. 6T). INOS message was decreased in resorbing tissue and was further decreased by treatment (FIG. 6U). IFN-γ message was elevated in resorbing tissue and was further elevated by treatment (FIG. 6V).

Examples 1–6 indicate that CTLA4 is localized with yolk sac vasculature. A novel form of CTLA4 may be a soluble protein localized in the ECM, based on the sensitivity of the surface expression to collagenase. These observations contrast with the currently held paradigm which asserts that the B7 receptors function solely in APC cell—T cell surface interactions and that lymphocyte markers arise only in the context of thymic development. The viability of CTLA4 deficient mice (Chambers et al., 1997, *Proc Natl Acad Sci USA* 94,9296–301), as well as B7-1/B7-2, CD28, MHC class I and class II deficient mice (Borriello et al., 1997, *Immunity* 6, 303–13; Chitilian and Auchincloss, 1997, *J Heart Lung Transplant* 16, 153–9; Green et al., 1994, *Immunity* 1, 501–8), clearly demonstrate that an adult-type antigen presenting signaling network is not absolutely required for embryo development. CTLA4 deficient neonates show no morphological abnormalities, but disregulated lymphoproliferation occurs within 3–4 weeks leading to massive lymphoadenopathy, splenomegaly and eventual death (Tivol et al., 1995, *Immunity* 3, 541–7). Despite these observations, one cannot eliminate the possibility that functional redundancy exists within the embryonic system, and that developmental influence exerted by costimulatory molecules may only be detected within specific genetic contexts. Indeed, these effects would not be seen in current studies because the routine production of gene deficient mice involves the use of inbred strains in which immunologic incompatibility is precluded.

The yolk sac is an extra-embryonic tissue derived from the embryo consisting of endodermal and mesodermal layers, endothelial cell derived blood islands, and capillary networks. The function of the yolk sac layer is thought to be three-fold: to absorb material nutrients and macromolecules, to provide embryonic circulation that would transmit this material to the developing embryo, and to generate hematopoietic cells (Auerbach et al., 1996, *Stem Cells* 14, 269–80; Exalto, 1995, *Eur J Obstet Gynecol Reprod Biol* 61, 3–6; Seino et al., 1995, *Int Immunol* 7, 1331–7). A recent investigation of adult porcine endothelium (Davis et al., 1996, *Int Immunol* 8, 1099–111) documented the presence of a soluble form of B7.1, suggesting that endothelial cells have the capacity to produce soluble costimulatory molecules. In addition, it has been shown that a growing number of proteins such as cytokines and growth factors are sequestered in the extracellular matrix (Taipale and Keski-Oja, 1997, *Faseb J* 11, 51–9) of vascular endothelial cells, and are thought to provide a potent signaling environment within the endothelial stroma.

Yolk sac hematopoietic cells have been extensively studied, including erythrocytes and monocytes/macrophages, but it is not likely that these cells comprise the CTLA4 positive population. The absence of CD45, and the presence of PECAM-1 on this population combined with immunolocalization to vascular tissue very strongly suggests that these cells are endothelial in origin (Baldwin et al., 1994, *Development* 120, 2539–53; Ling et al., 1997, *Eur J Immunol* 27, 509–14; Riseau and Flamme, 1995, *Ann Rev Cell Dev Biol* 11, 73–91). Hematopoietic stem cells, the precursors to all adult lymphoid cells, have been detected in the AGM region as early as day 10 of embryogenesis, but mature lymphoid cells do not appear until later in development. The detection of CTLA4 gene and surface expression on day 8.5 yolk sac indicates that the embryonic form of CTLA4 arises very early in development, up to 4 days prior to thymic development. The embryonic thymus initiates development from the descent of the thymic lineage at day 12, with immature T cell progenitors appearing only after that point (Shortman and Wu, 1996, *Annu Rev Immunol* 14, 29–47). B1-a and B1-b cells, the dominant forms of embryonic B cells, do not appear until after day 16 of embryonic development. B cell progenitors arise starting from fetal omentum and fetal liver at day 12–14 (Kantor and Herzenberg, 1993, *Annu Rev Immunol* 11, 501–38), but conventional B cells appear in substantial numbers only after birth. Some non-classical immune cells with lymphoid surface phenotype arise in the embryonic environment prior to T cell development as revealed in a series of reports investigating the ontogeny of NK T cells (Makino et al., 1996, *Proc Natl Acad Sci* USA 93, 6516–20). Flow cytometric studies demonstrated the presence of the cells in day 14 fetal liver with Vaphal4 and Vbeta8+, CD3+, CD4- and CD8- surface phenotype, characteristic of NK T cells. More significantly, gene rearrangement corresponding to Valpha 14 and Vbeta 8 were also detected in day 11 yolk sac suggesting a pre-fetal liver origin for this cell type. In a separate study, a spontaneously transformed cell line was derived from yolk sac in vitro culture with the phenotype CD4-, CD8-, and Vbeta8+ (Liu et al., 1993, *Thymus* 21, 221–33). The phenotype of this cell line has been confirmed, but the cells do not stain for CTLA4 (data not shown). Expression of certain other immunological molecules in embryos and yolk sac prior to lymphopoiesis has been observed. One recent study (Marcos et al., 1997, *J Immunol* 158, 2627–37) reported the detection of B-type cell markers by DNA amplification techniques in yolk sac and developing embryo cDNA samples. cDNA amplification products detected in day 8.5 yolk sac include c-kit, CD34, and RAG-1, but most notably, amplification of genomic DNA revealed IgH DJ rearrangements, 4 days prior to gene rearrangement detected in day 12/13 omentum and day 11.5 liver. In another study RAG-1, but not RAG-2, gene expression was detected in pre-implantation embryos, suggesting the mechanism for gene rearrangement to be present as soon as 2/3 days post coitum.

Current models of maternal immunological tolerance of the embryo have centered on two complementary mechanisms: utilization of indirect cytokine and hormonal signaling and the active immunosuppression of maternal lymphocytes. Recently, a number of known immunomodulatory cytokines were described that have been demonstrated to influence maternal tolerance of the embryo. Whereas the ThI cytokines promoting cellular cytotoxicity (e.g., during an intracellular parasitic infection) such as TNF-α, IFN-γ, IL-2, IL-1, IL-6, IL-12, and RANTES have been demonstrated to increase spontaneous abortion rates in abortion prone mice, the presence of Th2 cytokines such as CSF-1, GM-CSF, IL-10, IL-4, IL-11, TGF and IL-3 which promote humoral immunity, have been shown to correlate with reduced abortion rates (Chaouat et al., 1990, *J Reprod Fertil* 89, 447–58; Gafter et al., 1997, *J Clin Immunol* 17, 408–19). Active immunosuppression has also been documented in studies with factors derived from embryonic sources. In the past, some unidentified proteins and anti-paternal blocking antibodies have been reported to confer modest immunosuppression to the embryo (Herrera-Gonzalez and Dresser, 1993, *Dev Comp Immunol* 17, 1–18). Examples 7–11 indicate that expression levels of numerous cytokines, as well as adhesion molecules and cell-surface antigens, are altered in mice during pathologic pregnancy, but that many can be normalized by treatment with CTLA41g. Altered expression levels of these genes, therefore may be used as diagnostic criteria for determining whether a subject is at risk for, or developing or suffering from, an immune-mediated spontaneous abortion.

The results presented in this study also indicate that immune mediated spontaneous abortion in mice can be ameliorated by administration of CTLA4 Ig. An extension of this work to human reproductive failure suggests that CTLA4 Ig will be a useful therapeutic in cases of recurrent immune mediated spontaneous abortion in abortion-prone women where the downregulation of cellular immune responses at the fetal/maternal interface may be beneficial to the survival of the fetus. A further use of CTLA4 Ig may be to improve the success rate of embryo transfer techniques in humans. It is currently estimated that artificial reproductive techniques utilizing embryo transfers in humans is low, with a success rate of approximately 15 percent (Karlstrom et al., 1997, *Hum Reprod* 12, 1263–6; Registry, 1996, *Fertil Steril* 66, 697–705). Although the exact cause of the high failure rate associated with this procedure is not understood, it is known that embryo manipulation technique and cryopreservation often results in tissue damage which in turn, has been shown to potentiate T activation in vitro (Ewoldsen et al., 1987, *J Immunol* 138, 2764–70; Lee et al., 1997, *J Assist Reprod Genet* 14,170–3). If T cell activation occurs analogously in cases where embryos are transferred in adult reproductive systems, it is likely that CTLA4 Ig may enhance the survival rate of the transferred embryos. In summary, the detection of an extracellularly localized CTLA4 in mouse yolk sac suggests that the embryonic CTLA4 protein functions as an immunoregulator of the maternal immune system.

Equivalents

Those skilled in the art will recognize, or be able to ascertain using no more than routine experimentation, numerous equivalents to the specific compositions and methods described herein. Such equivalents are considered to be within the scope of this invention and are covered by the following claims.

What is claimed is:

1. A method of inhibiting spontaneous abortion in a non-human, mammalian subject comprising administering to the subject a soluble CTLA4-Ig fusion protein such that spontaneous abortion in the subject is inhibited.

2. The method of claim 1, wherein the soluble CTLA4-Ig fusion protein comprises an imunoglobulin concostant region domain that has been modified to reduce at least one effector-mediated function.

3. The method of claim 1, wherein the subject is a domesticated animal.

4. The method of claim 1, wherein the subject is an endangered species.

5. The method of claim 1, wherein the subject is an animal being used to carry cloned, non-human animals.

6. A method of downregulating an immune response by a subject to an embryo comprising: administering to the subject a therapeutically effective amount of a soluble CTLA4-Ig fusion protein such that the immune response to the embryo is downregulate.

7. The method of claim 6, wherein the subject is a human.

8. The method of claim 7, wherein the subject has had a previous spontaneous abortion.

9. The method of claim 6, wherein the soluble CTLA4-Ig fusion protein is administered to the subject prior to implantation of the embryo.

10. The method of claim 9, which further comprises administering to the subject soluble CTLA4-Ig fusion protein after implantation of the embryo.

11. The method of claims 6, wherein the soluble CTLA4-Ig fusion protein comprises an immunoglobulin constant region domain that has been modified to reduce at least one effector-mediated function.

12. A method of enhancing the ability of a subject to carry at least one embryo to term comprising administering to the subject a soluble CTLA4-Ig fusion protein to reduce an immune response by the subject to the embryo.

13. A method of inhibiting spontaneous abortion in a mammnalian subject comprising administering to the subject a soluble CTLA4-Ig fusion protein such that spontaneous abortion in the subject is inhibited.

14. The method of claim 13, wherein the subject is a human.

15. A method of inhibiting spontaneous abortion in a non-human, mammnalian subject comprising administering to the subject an antibody that binds to B17-1 and an antibody that binds B7-2 such that spontaneous abortion in the subject is inhabited.

16. The method of claim 15, wherein the subject is a domesticated animal.

17. The method of claim 15, wherein the subject is an endangered species.

18. The method of claim 15, wherein the subject is an animal being used to carry cloned, non-human animals.

19. A method of downregulating an immune response by a subject to an embryo comprising administering to the subject a therapeutically effective amount of an antibody that binds to B7-1 and an antibody that binds to B7-2 such that the immune response to the embryo is downregulate.

20. The method of claim 19, wherein the subject is a human.

21. The method of claim 20, wherein the subject has had a previous spontaneous abortion.

22. The method of claim 19, wherein the antibodies are administered to the subject prior to implantation of the embryo.

23. The method of claim 22, which further comprises administering to the subject an antibody that binds to 87-1 and an antibody that binds to B7-2 after implantation of the embryo.

24. A method of enhancing the ability of a subject to carry at least one embryo to term comprising administering to the subject an antibody that binds to B7-1 4and an antibody that binds to B7-2 to reduce an immune response by the subject to the embryo.

25. A method of inhibiting spontaneous abortion in a mammnalian subject comprising administering to The subject an antibody to B7-1 and an antibody to B7-2 such that spontaneous abortion in the subject is inhibited.

26. The method of claim 25, wherein the subject is a human.

* * * * *

UNITED STATES PATENT AND TRADEMARK OFFICE
CERTIFICATE OF CORRECTION

| | | |
|---|---|---|
| PATENT NO. | : 6,613,327 B1 | |
| APPLICATION NO. | : 09/628129 | |
| DATED | : September 2, 2003 | |
| INVENTOR(S) | : Ling et al. | |

It is certified that error appears in the above-identified patent and that said Letters Patent is hereby corrected as shown below:

On Title page 1 of the issued Patent, Item (75) Inventors:

"James C. Keith, Andover, MA (US);" should read --James C. Keith, Jr., Andover, MA (US);--

Col 43 line 21-22
Claim 2. "...fusion protein comprises an imunoglobulin concostant region domain..."

should read

--...fusion protein comprises an immunoglobulin constant region domain...--

Col 43 line 31-32
Claim 6. "...comprising: administering to the subject a therapeutically effective amount of a soluble CTLA4-lg fusion protein such that the immune response to the embryo is downregulate."

should read

--...comprising administering to the subject a therapeutically effective amount of a soluble CTLA4-lg fusion protein such that the immune response to the embryo is downregulated.--

Col 43 line 45
Claim 11. "The method of claims 6,..."

should read

--The method of claim 6,...--

UNITED STATES PATENT AND TRADEMARK OFFICE
CERTIFICATE OF CORRECTION

PATENT NO. : 6,613,327 B1
APPLICATION NO. : 09/628129
DATED : September 2, 2003
INVENTOR(S) : Ling et al.

It is certified that error appears in the above-identified patent and that said Letters Patent is hereby corrected as shown below:

Col 43 line 53-54
Claim 13. "...spontaneous abortion in a mammnalian subject..."

should read

--...spontaneous abortion in a mammalian subject...--

Col 44 line 17-21
Claim 15. "A method of inhibiting spontaneous abortion in a non-human, mammnalian subject comprising administering to the subject an antibody that binds to B17-1 and an antibody that binds B7-2 such that spontaneous abortion in the subject is inhabited."

should read

--A method of inhibiting spontaneous abortion in a non-human, mammalian subject comprising administering to the subject an antibody that binds to B7-1 and an antibody that binds B7-2 such that spontaneous abortion In the subject is inhibited.--

Col 44 lines 32-33
Claim 19. "...such that the immune response to the embryo is downregulate."

should read

--...such that the immune response to the embryo is downregulated.--

Col 44 line 41
Claim 23. "...an antibody that binds to 87-1 and an antibody that binds to..."

should read

--...an antibody that binds to B7-1 and an antibody that binds to...--

UNITED STATES PATENT AND TRADEMARK OFFICE
CERTIFICATE OF CORRECTION

PATENT NO. : 6,613,327 B1
APPLICATION NO. : 09/628129
DATED : September 2, 2003
INVENTOR(S) : Ling et al.

It is certified that error appears in the above-identified patent and that said Letters Patent is hereby corrected as shown below:

Col 44 line 46
Claim 24.   "...an antibody that binds to B7-1 4and an antibody..."

should read

"...an antibody that binds to B7-1 and an antibody...--

Col. 44 line 50-51
Claim 25.   "...in a mammnalian subject comprising administering to The subject an antibody..."

should read

--...in a mammalian subject comprising administering to the subject an antibody...--

Signed and Sealed this

Twenty-fourth Day of October, 2006

JON W. DUDAS
*Director of the United States Patent and Trademark Office*

SEQUENCE LISTING

```
<160> NUMBER OF SEQ ID NOS: 5

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:proline-rich
      sequence critical for binding of CD28 to B7-1 and B7-2

<400> SEQUENCE: 1

Met Tyr Pro Pro Pro Tyr
  1               5

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 2
cacaacactg atgaggtccg                                                    20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 3
tgagttccac cttgcagagg                                                    20

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 4
gtcgtcgaca acggctccgg catgtg                                             26
```

```
<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 5
cattgtagaa ggtgtggtgc cagat                                              25
```